(12) United States Patent
Samsoondar

(10) Patent No.: US 10,272,430 B2
(45) Date of Patent: *Apr. 30, 2019

(54) DISPOSABLE CARTRIDGE WITH HINGED CAP

(71) Applicant: INVIDX CORP., Markham (CA)

(72) Inventor: James Samsoondar, Markham (CA)

(73) Assignee: INVIDX CORP. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/995,895

(22) Filed: Jun. 1, 2018

(65) Prior Publication Data

US 2018/0272342 A1 Sep. 27, 2018

Related U.S. Application Data

(63) Continuation of application No. 15/680,736, filed on Aug. 18, 2017, now Pat. No. 9,999,884, which is a
(Continued)

(51) Int. Cl.
*B01L 3/00* (2006.01)
*G01N 33/86* (2006.01)

(52) U.S. Cl.
CPC ..... *B01L 3/50273* (2013.01); *B01L 3/502715* (2013.01); *B01L 3/502723* (2013.01); *B01L 3/502784* (2013.01); *B01L 2200/025* (2013.01); *B01L 2200/0605* (2013.01); *B01L 2200/0684* (2013.01); *B01L 2300/042* (2013.01);
(Continued)

(58) Field of Classification Search
CPC ........... B01L 3/50273; B01L 3/502784; B01L 3/502715; B01L 3/502723; B01L 2200/025; B01L 2400/0487; B01L 2300/043; B01L 2300/0867; B01L 2200/0684; B01L 2300/046; B01L 2300/042; B01L 2400/0688; B01L 2200/0605; B01L 2300/0816; G01N 33/86

See application file for complete search history.

(56) References Cited

U.S. PATENT DOCUMENTS 4,514,091 A 4/1985 Kaspar et al.
4,722,714 A 2/1988 Marbourg, Jr.
(Continued)

FOREIGN PATENT DOCUMENTS

CA 2911318 A1 11/2015
WO 2016/049545 A1 3/2016

OTHER PUBLICATIONS

International Search Report and Written Opinion in International Application No. PCT/CA2017/050584, dated Jan. 15, 2018.

*Primary Examiner* — Sally A Merkling
(74) *Attorney, Agent, or Firm* — J.A. Lindeman & CO., PLLC

(57) ABSTRACT

A disposable cartridge and method for measuring one or more properties of a blood sample are provided. The disposable cartridge can receive a sample when it is in an unsealed configuration. After adjusting the cartridge from the unsealed configuration to a sealed configuration, facilitated by a hingedly attached cap, pressurized air from an air bladder may be used to force the blood from a sample storage well into a detection chamber in a regulated manner, so that the one or more properties of the blood sample may then be measured.

20 Claims, 25 Drawing Sheets

Related U.S. Application Data continuation of application No. PCT/CA2017/050584, filed on May 16, 2017, which is a continuation-in-part of application No. 15/356,630, filed on Nov. 20, 2016, now Pat. No. 9,821,307.

(60) Provisional application No. 62/258,520, filed on Nov. 22, 2015.

(52) U.S. Cl.
CPC ... *B01L 2300/043* (2013.01); *B01L 2300/046* (2013.01); *B01L 2300/0816* (2013.01); *B01L 2300/0867* (2013.01); *B01L 2400/0487* (2013.01); *B01L 2400/0688* (2013.01); *G01N 33/86* (2013.01)

(56) References Cited

U.S. PATENT DOCUMENTS

| | | | |
|---|---|---|---|
| 6,750,053 B1 | 6/2004 | Opalsky et al. | |
| 7,682,833 B2* | 3/2010 | Miller | B01L 3/502707 422/537 |
| 9,470,673 B2 | 10/2016 | Samsoondar | |
| 2010/0196908 A1* | 8/2010 | Opalsky | B01L 7/52 435/6.1 |

* cited by examiner

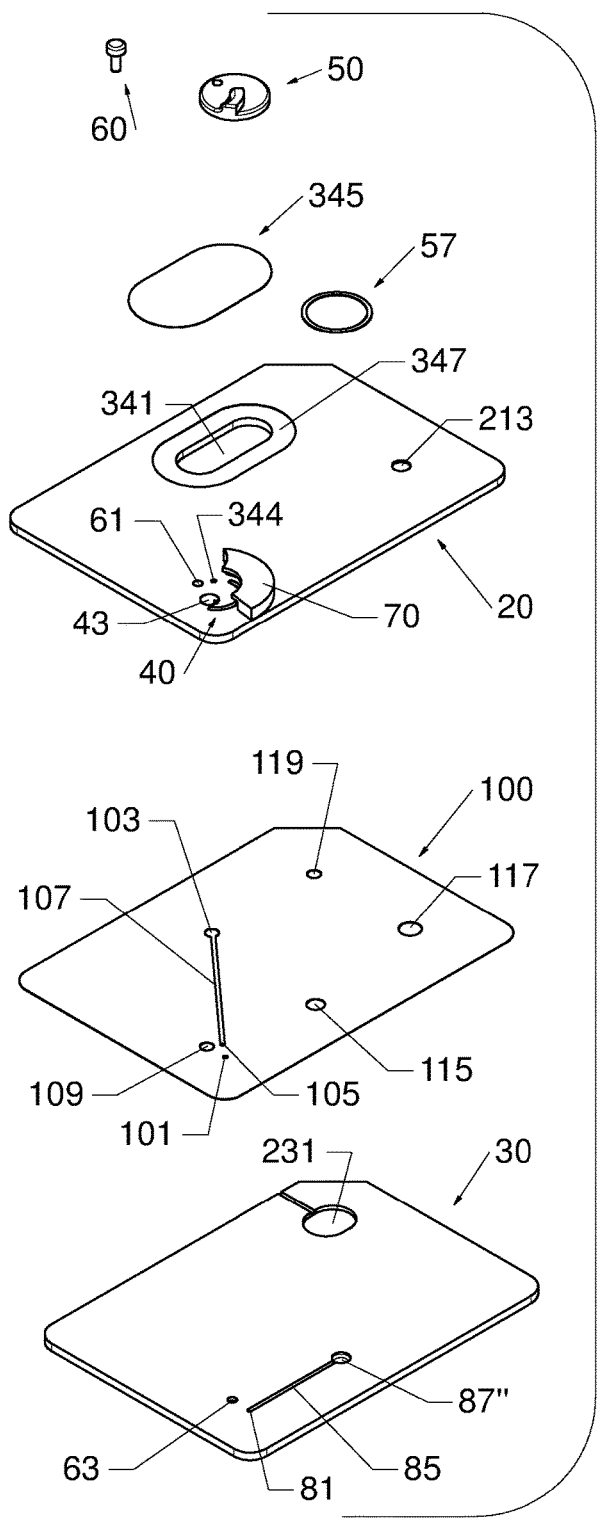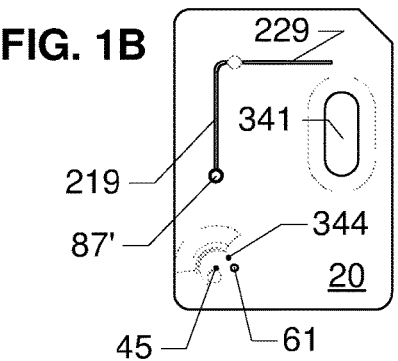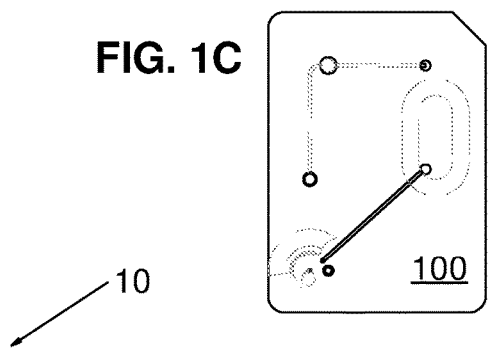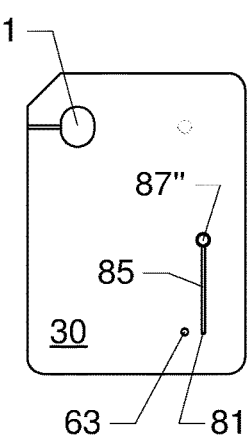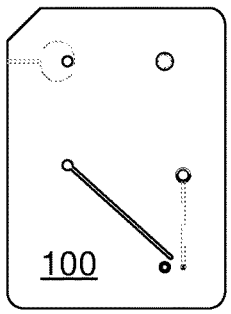

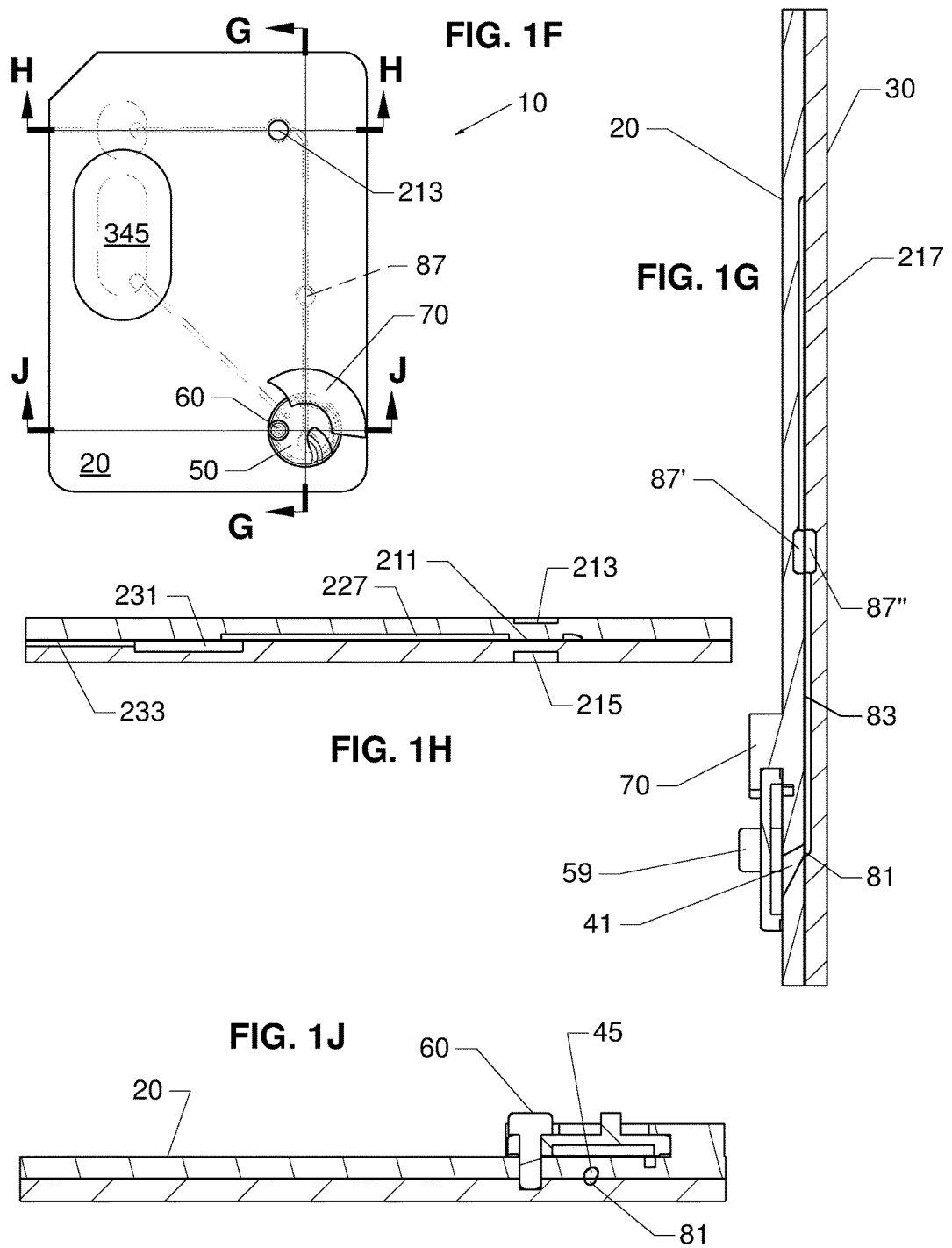

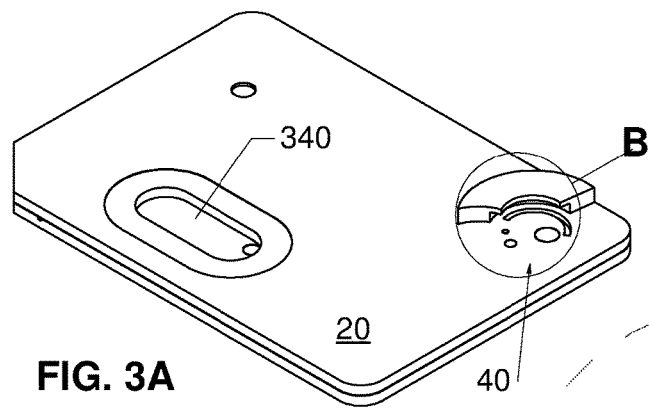
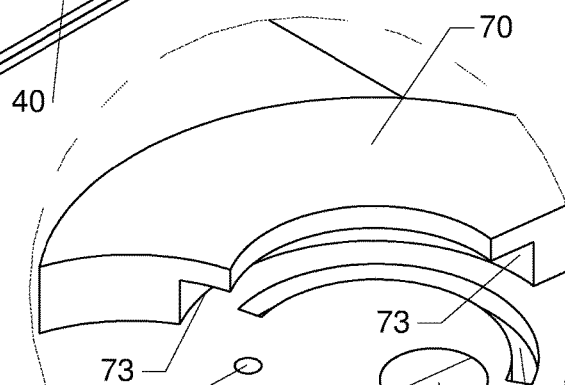
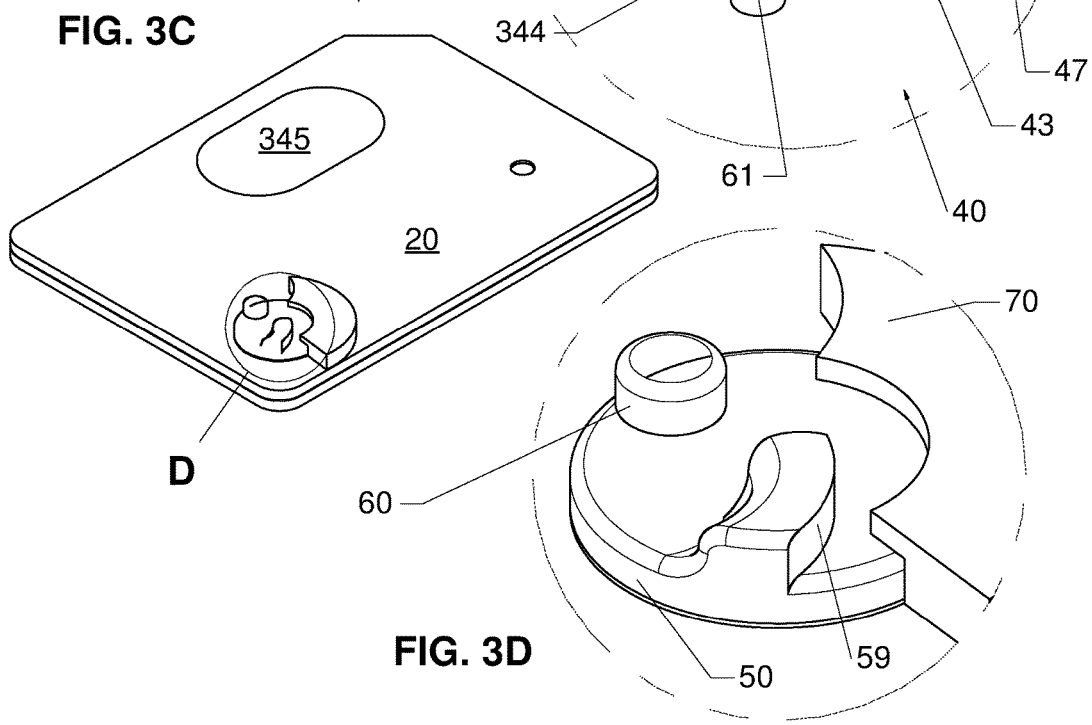

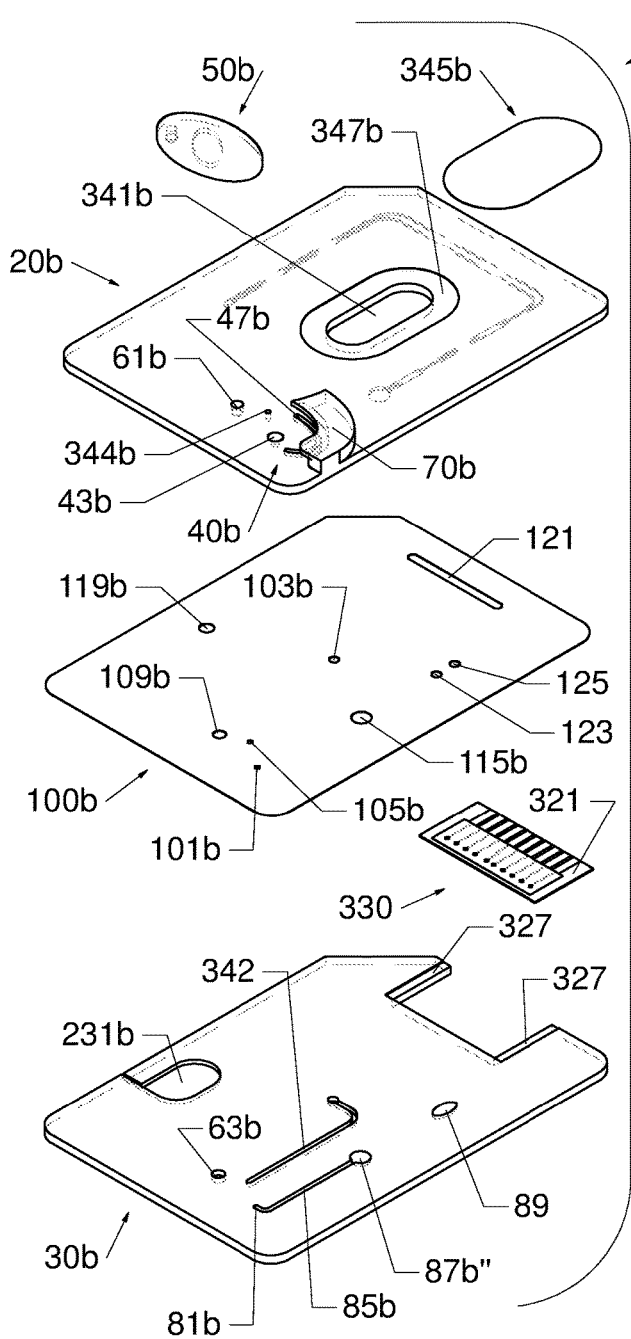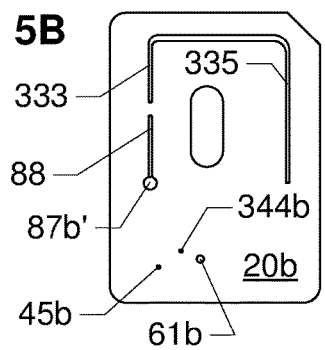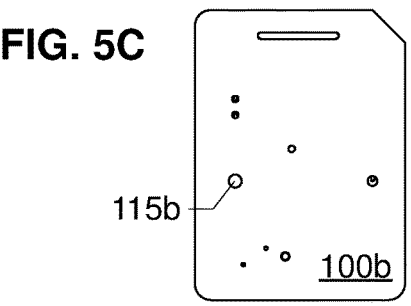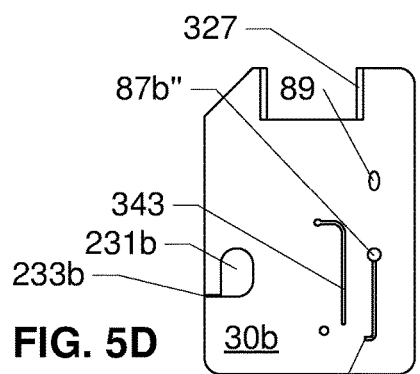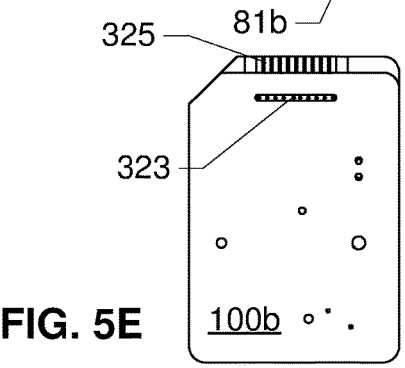

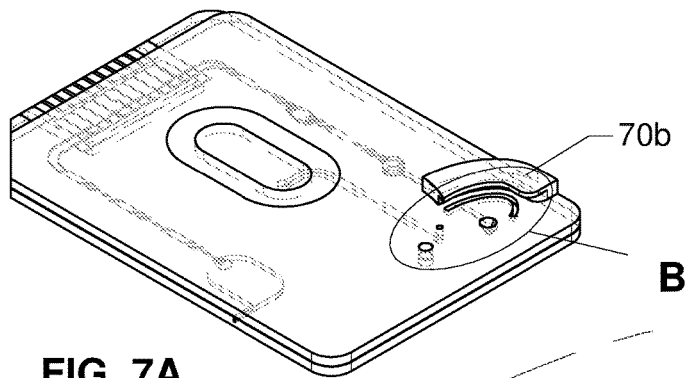
FIG. 7A
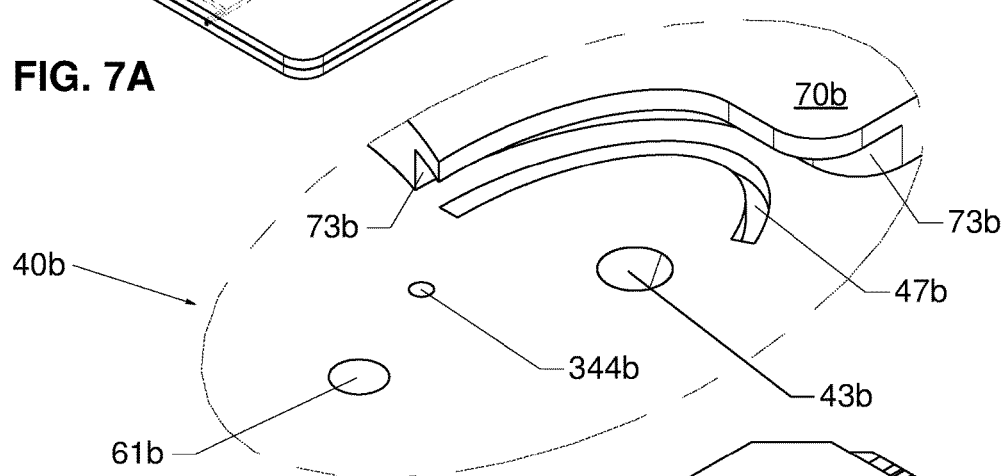
FIG. 7B
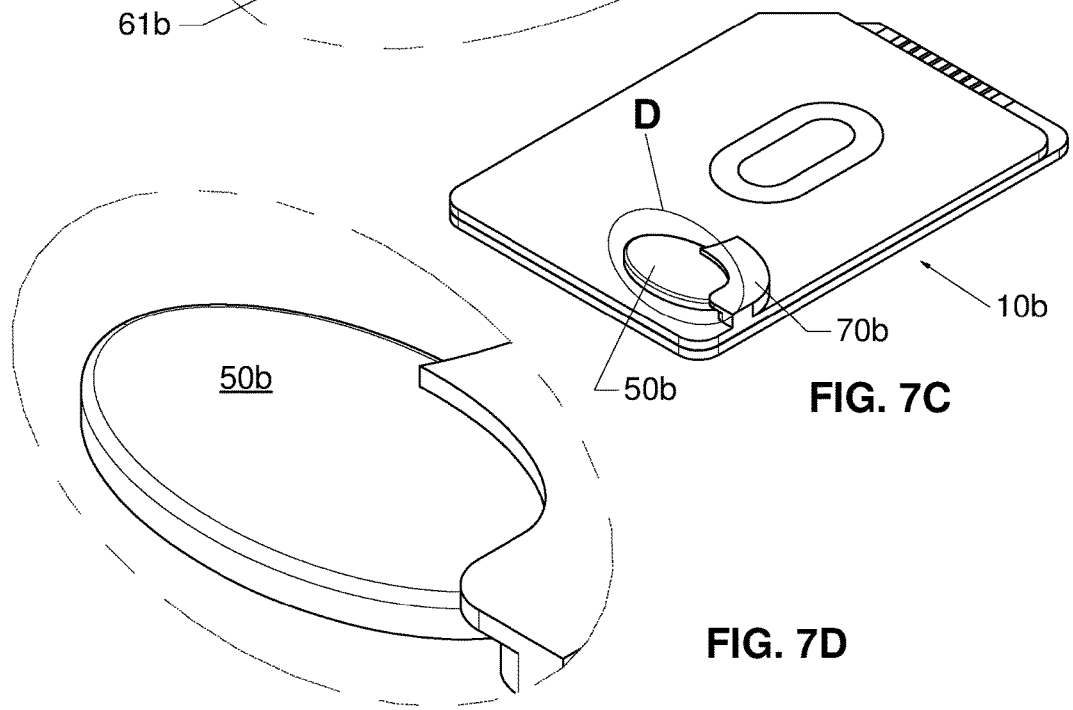
FIG. 7C
FIG. 7D

FIG. 8A
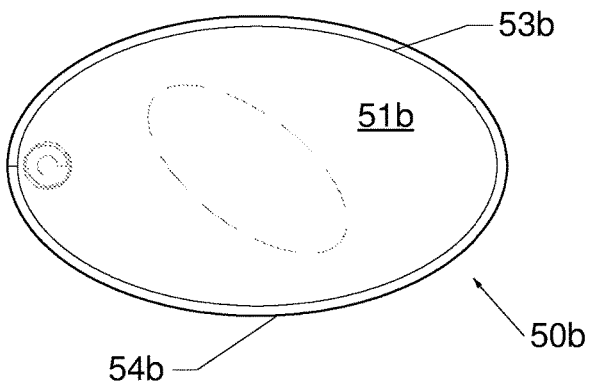
FIG. 8B
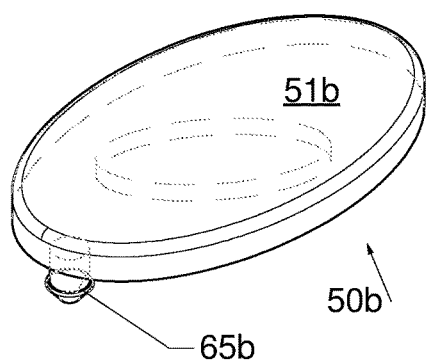
FIG. 8C
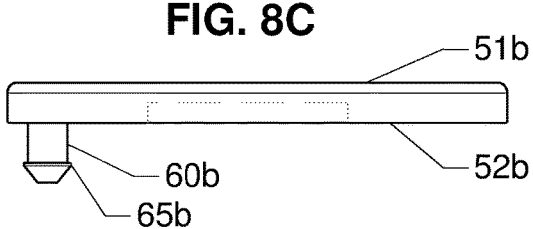
FIG. 8D
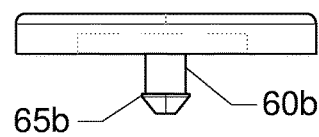
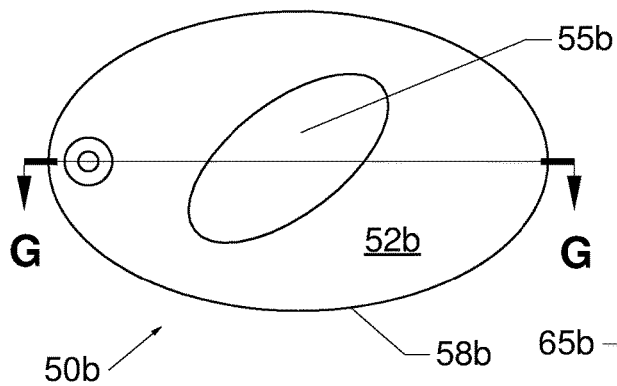
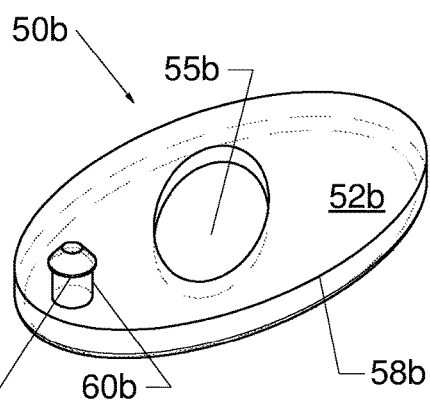
FIG. 8E
FIG. 8F
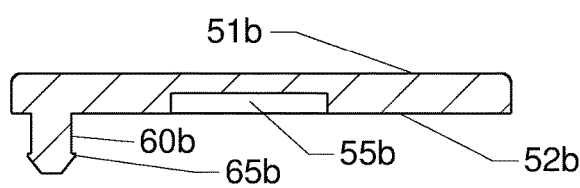
FIG. 8G

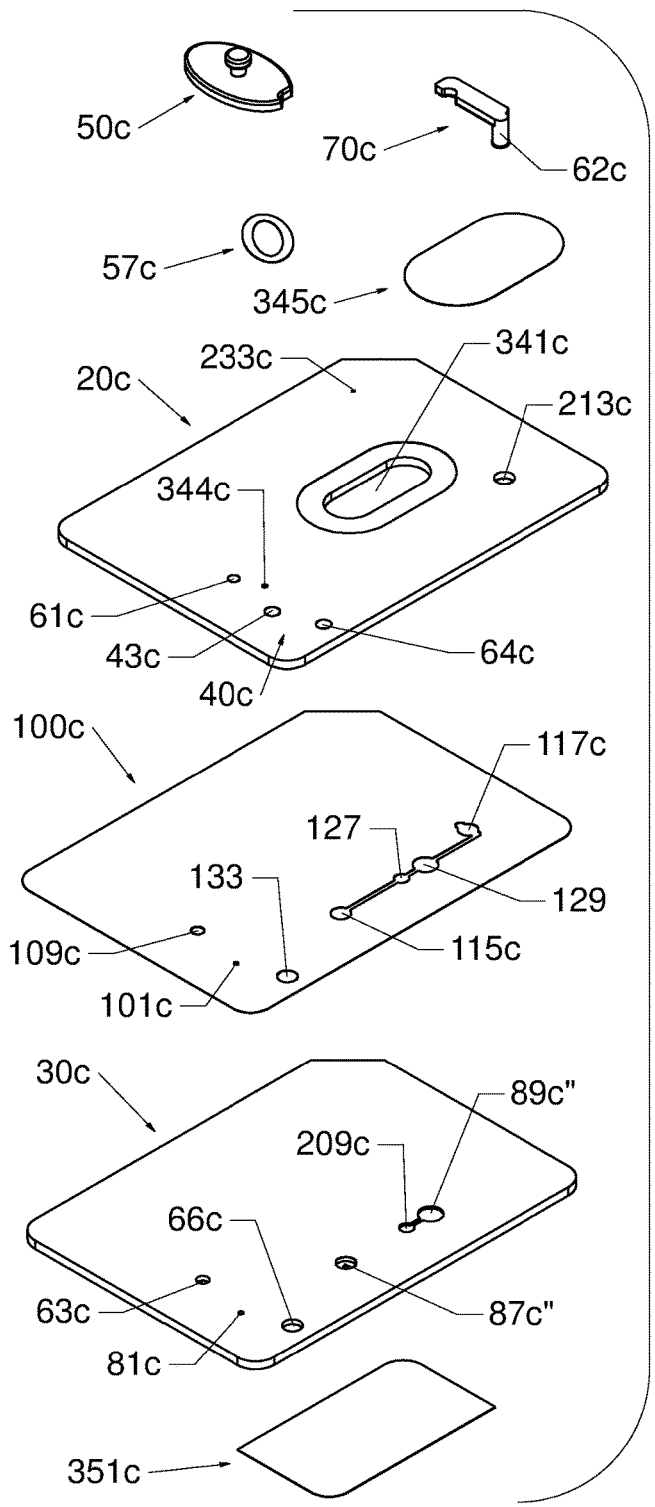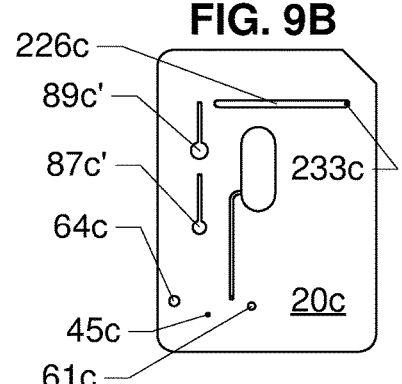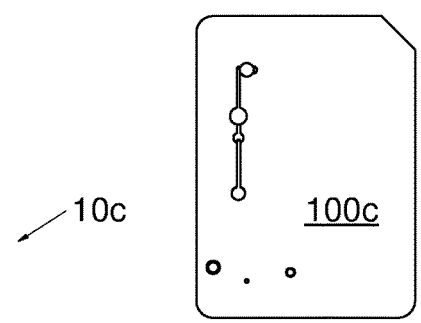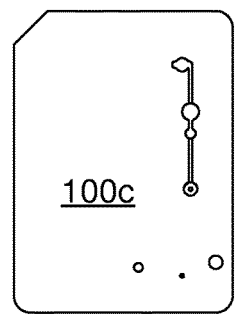

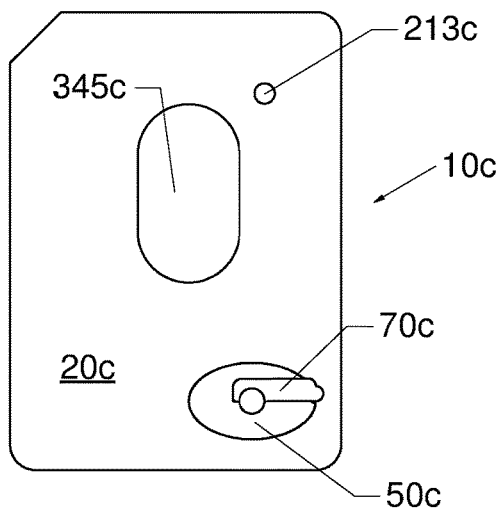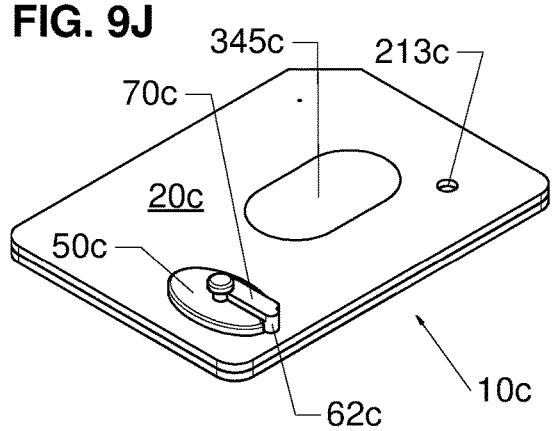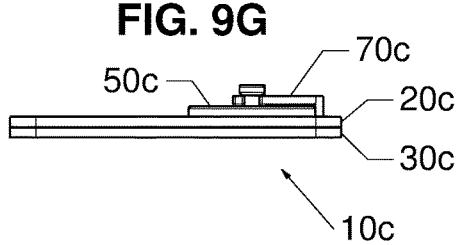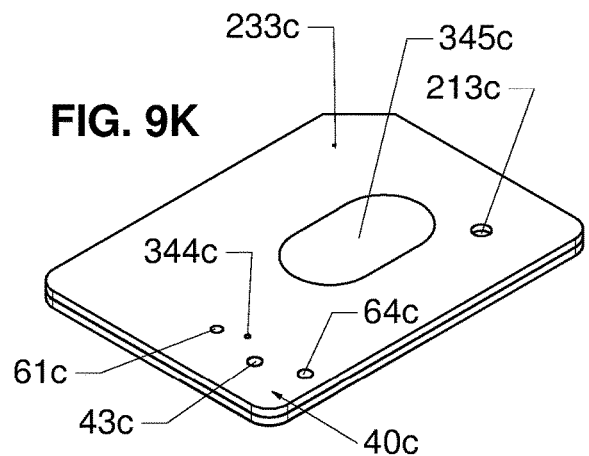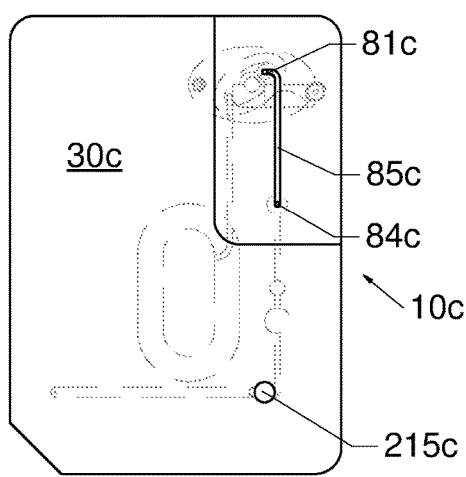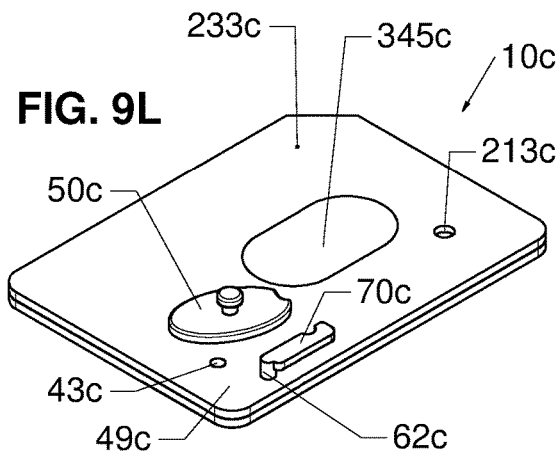

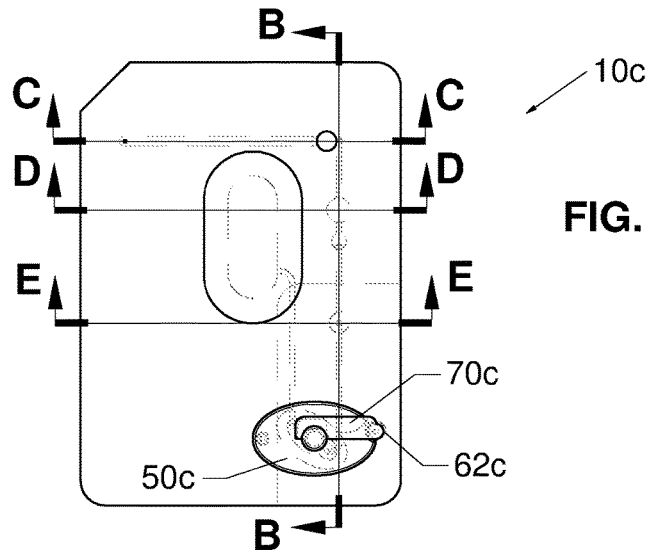
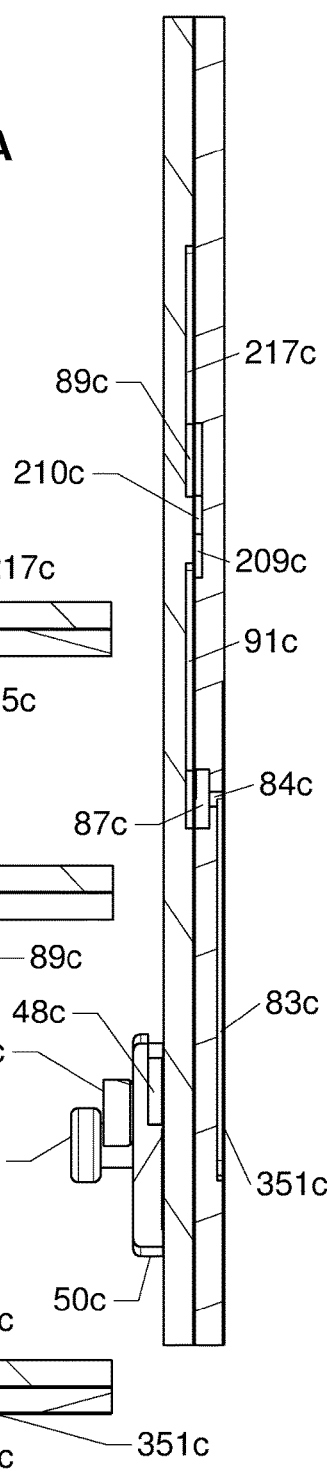
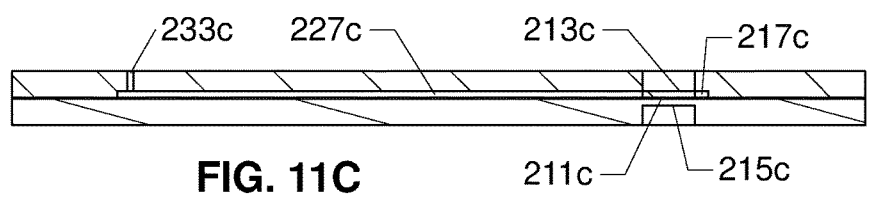
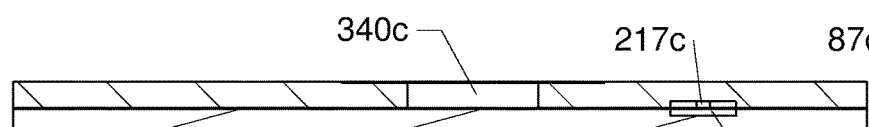
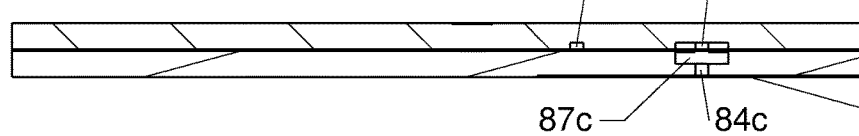

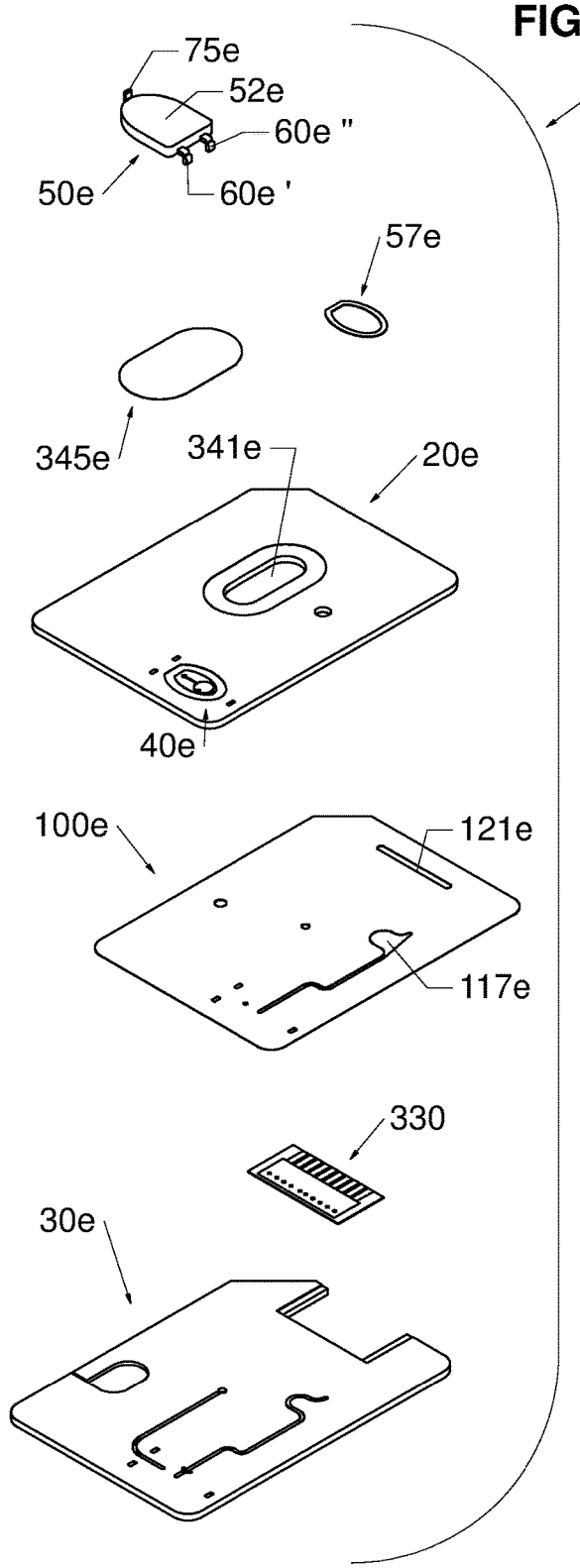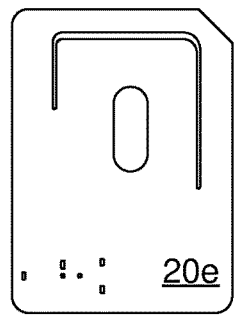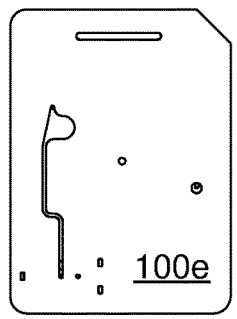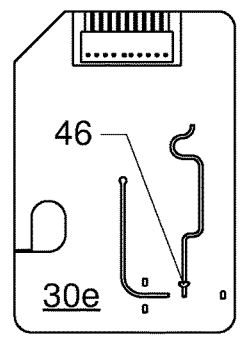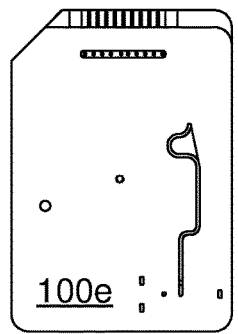

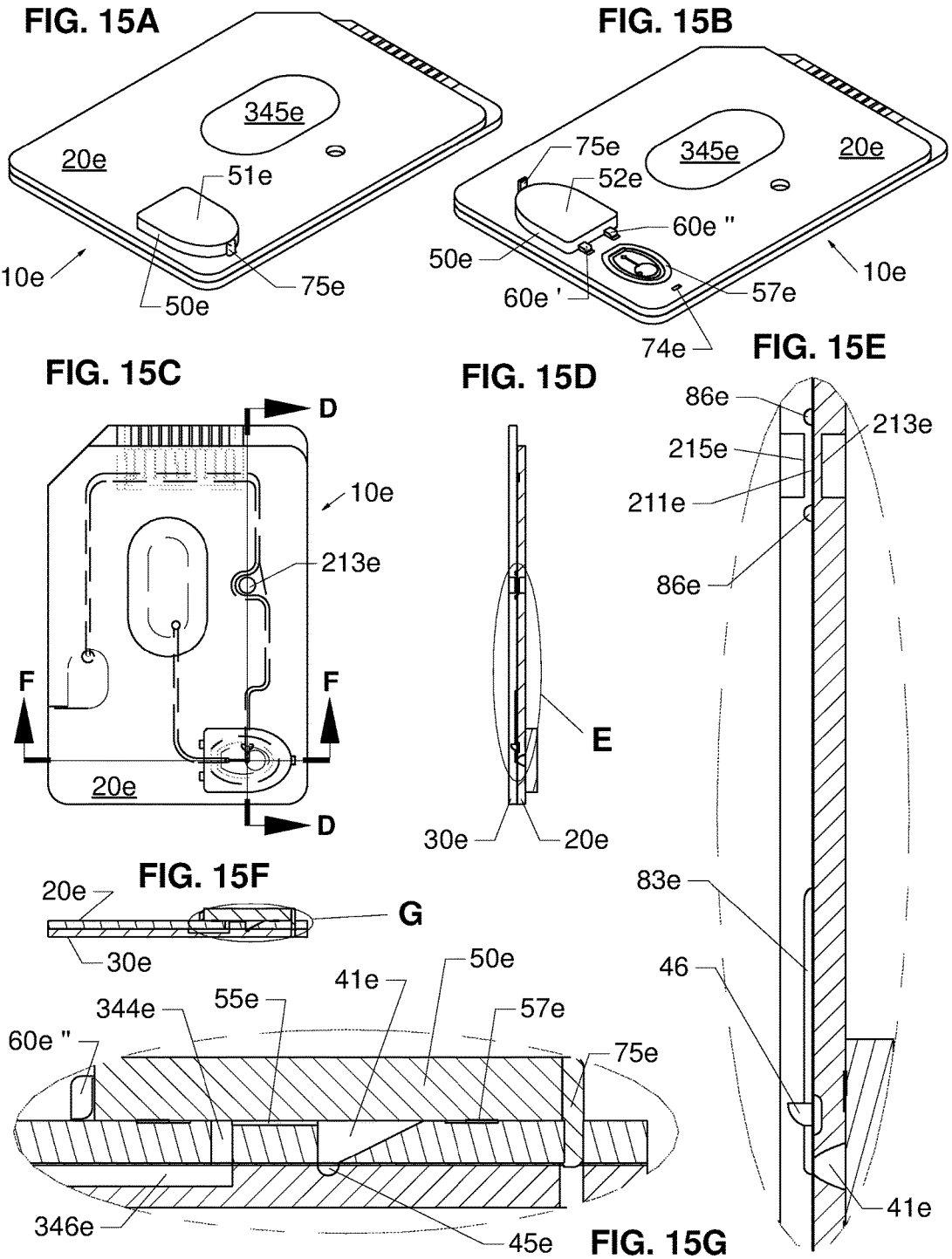

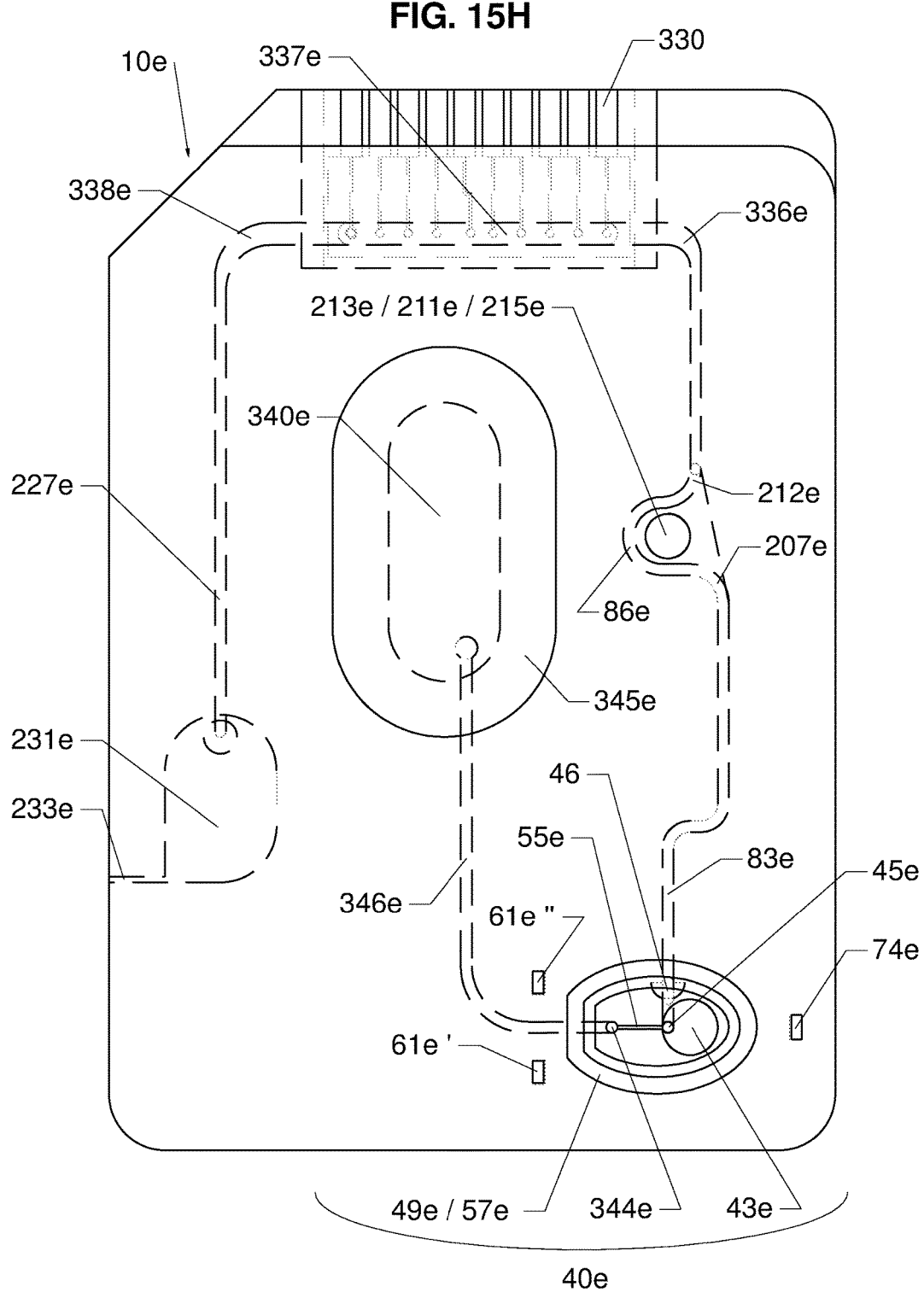

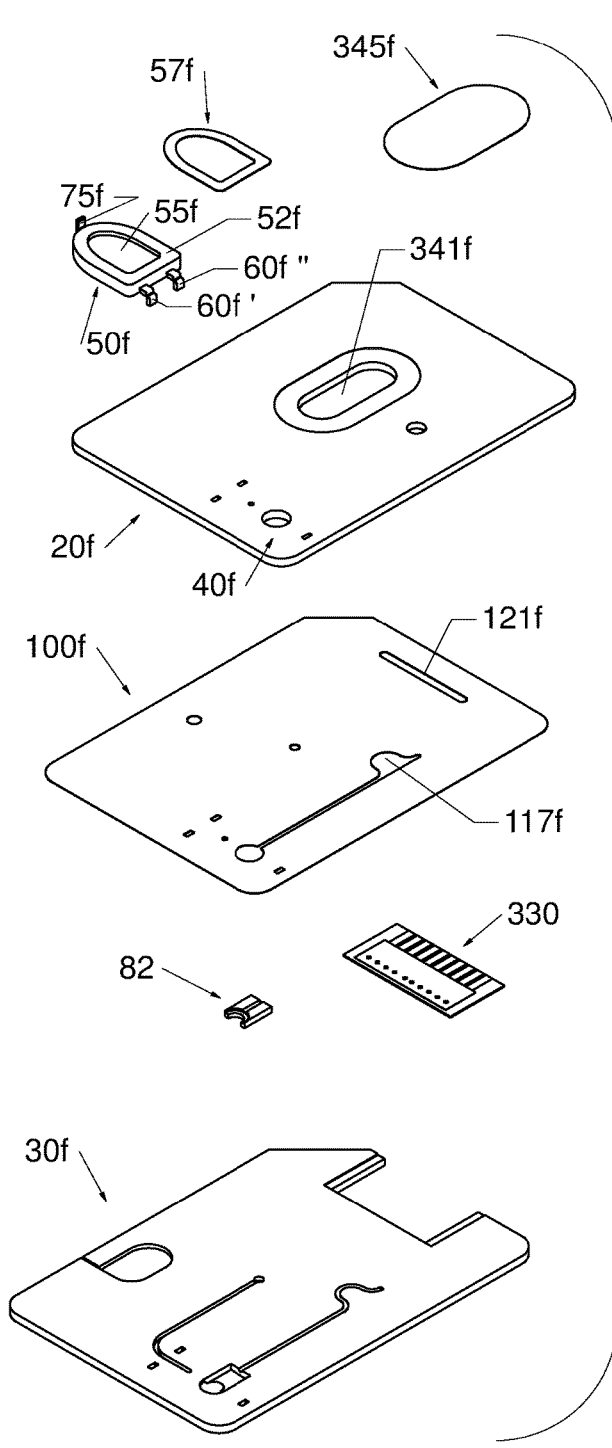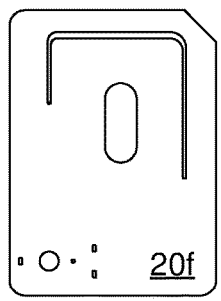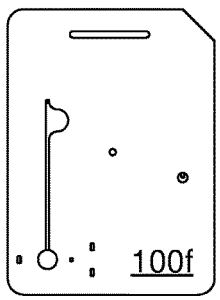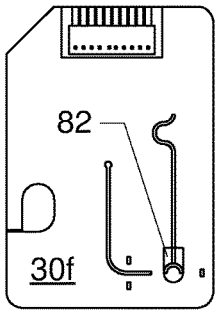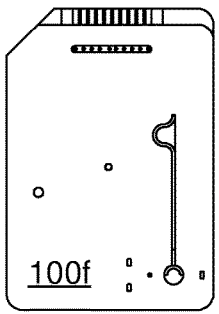
FIG. 16A
FIG. 16B
FIG. 16C
FIG. 16D
FIG. 16E

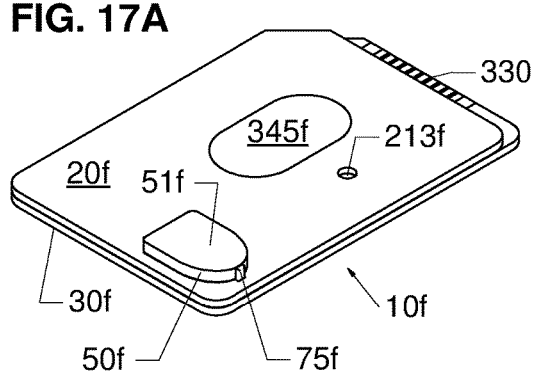
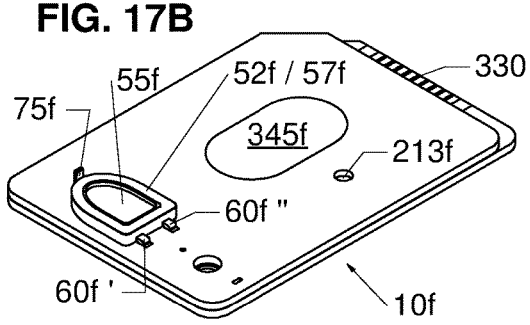
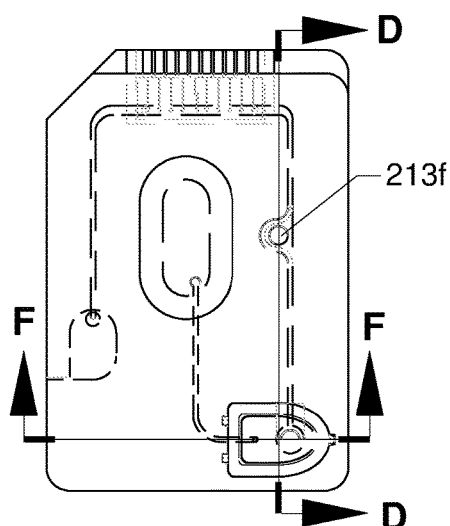
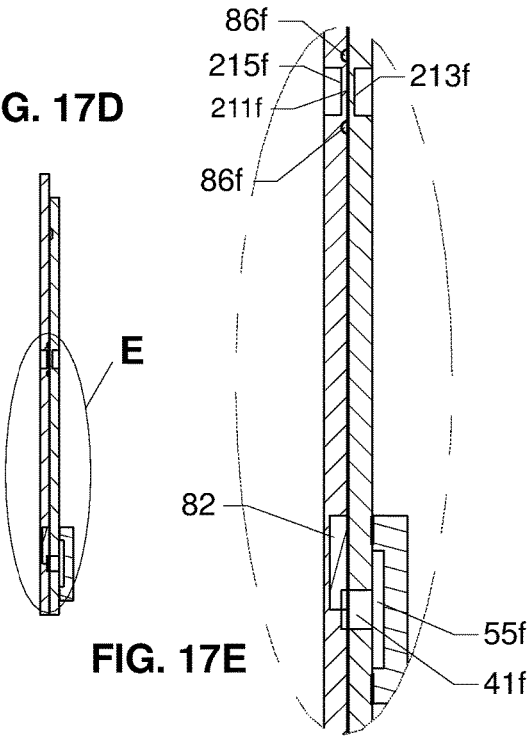
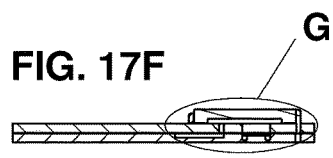
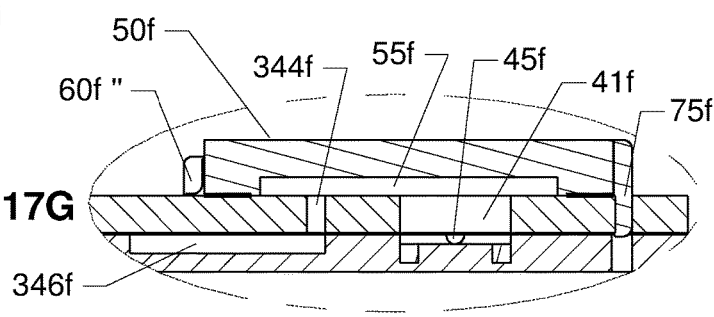

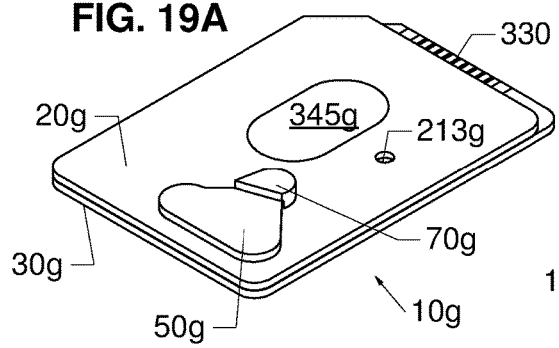
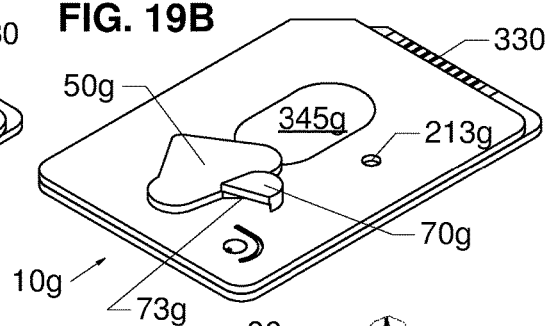
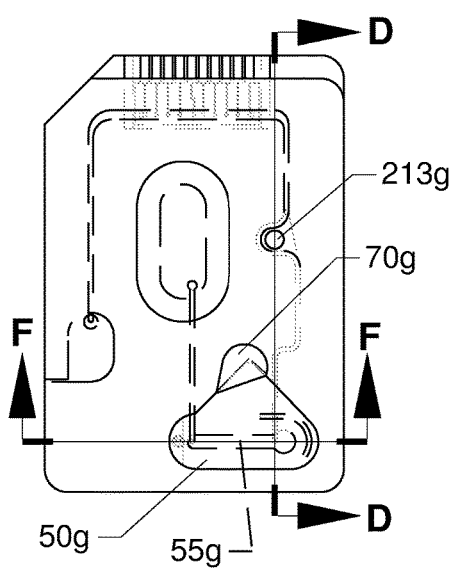
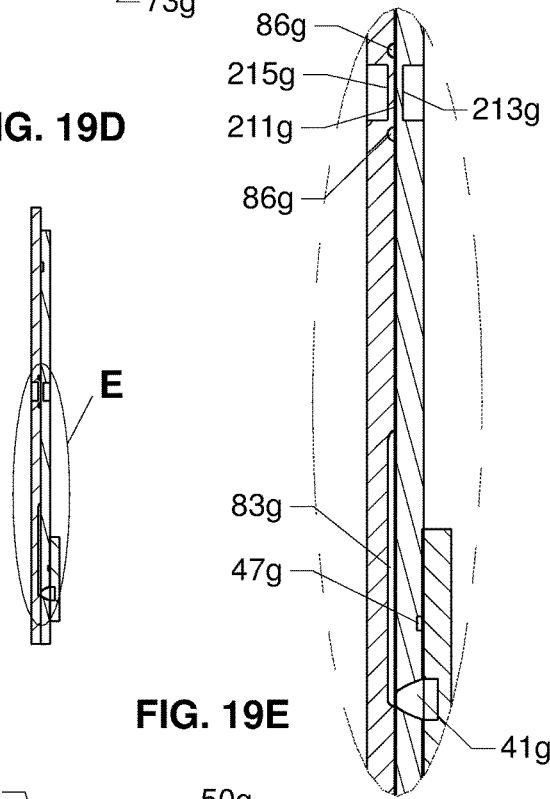
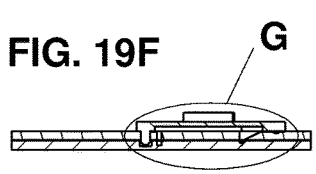
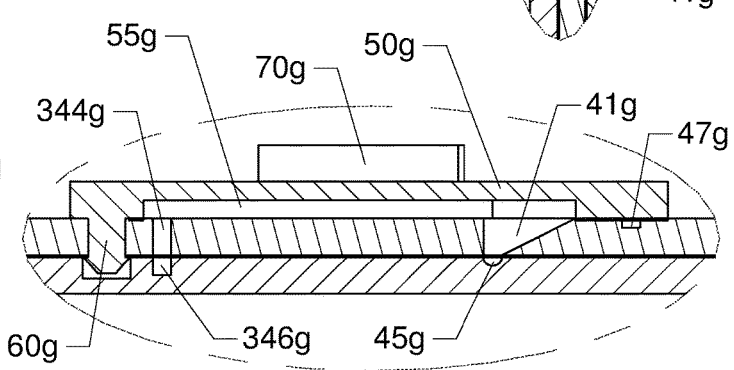

DISPOSABLE CARTRIDGE WITH HINGED CAP

CROSS-REFERENCE TO RELATED APPLICATIONS

This application is a continuation-in-part of U.S. application Ser. No. 15/680,736, filed Aug. 18, 2017, now U.S. Pat. No. 9,999,884; which is a continuation of International Application No. PCT/CA2017/050584, filed May 16, 2017; and is a continuation-in-part of U.S. application Ser. No. 15/356,630, filed Nov. 20, 2016, now U.S. Pat. No. 9,821,307; which claims the benefit of U.S. Provisional Application No. 62/258,520, filed Nov. 22, 2015; the entire contents of each of which are incorporated herein by reference.

FIELD OF THE INVENTION

The invention relates to a disposable cartridge used for measuring a property of a sample. The disposable cartridge is useful for point-of-care testing (POCT).

BACKGROUND OF THE INVENTION

The result of reaction between a liquid sample and one or more reagent, preferably dry, depends on the quantity of the one or more reagent and the volume of liquid sample. Although any type of liquid sample is implied, serum, plasma and blood (also referred to as whole blood) are samples of particular interest. When blood is allowed to clot and the sample is centrifuged, the yellow liquid that sits on top of the blood clot is called serum. If the blood is collected in a tube containing an anticoagulant, for example heparin, and the sample is centrifuged, the yellow liquid that sits on top of the packed red blood cells is called plasma. The packed red cell volume (PCV) or hematocrit determines the percentage of red blood cells (RBCs) in whole blood. Since only the RBCs contain hemoglobin, total hemoglobin is highly correlated with hematocrit, except in cases of for example, macrocytic anemia where the mean red cell hemoglobin concentration is lower than that of a normal red cell. Some analyzers measure hematocrit by electrical conductivity and convert the hematocrit measurement to a total hemoglobin concentration, and some analyzers measure total hemoglobin concentration by spectroscopy, and convert the total hemoglobin concentration to a hematocrit value. Spectroscopic calibration algorithms can be developed to measure both hematocrit and total hemoglobin concentration.

Point-of-care Testing (POCT) is defined as medical diagnostic testing performed outside the clinical laboratory in close proximity to where the patient is receiving care. POCT is typically performed by non-laboratory personnel and the results are used for clinical decision making. For the sake of convenience and rapid turnaround time, blood is the sample of choice. Due to the complexity of blood, certain tests can only be performed on serum or plasma.

POCT has a range of complexity and procedures that vary from manual procedures to automated procedures conducted by portable analyzers. POCT is most efficient when the sample of interest can be applied to or loaded onto a test cartridge, the sample inlet capped, and the remaining steps are performed automatically after the loaded and capped test cartridge is inserted into a slot or receptor of an analyzer. Some blood tests, for example coagulation assays and immunoassays require a fixed volume of sample, for example, to ensure that when mixed with a reagent the ratio of the volume of sample to the volume of the reagent is held constant. Other tests, for example that determine electrolytes, do not require a fixed volume of sample. In the case of electrolytes, sample volume may not be an issue if the electrolyte concentration is estimated by measuring electrical activity in the sample, but other issues regarding sample volume must be considered. Electrolytes are examples of tests that are usually measured using electrochemical sensors, also referred to as biosensors. There are other tests that do not require a fixed volume of sample, and cannot be measured using biosensors, for example CO-oximetry. CO-oximetry is a spectroscopic or optical technique that is used to measure different Hemoglobin (Hb) species present in a blood sample, for example, Oxy-Hb, Deoxy-Hb, Met-Hb, Carboxy-Hb and Total-Hb. As for electrolytes, other issues regarding sample volume must be considered, and are discussed in the next.

Electrolytes and CO-oximetry measurements do not usually require fixed volumes of blood, but a process is required to regulate the distance the blood is allowed to travel along microfluidic channels inside the cartridge. This distance is controlled by regulating the volume of blood dispensed from the sample storage well. The term metered blood means blood supplied in a measured or regulated amount.

Applying an unmetered sample volume to test strips is well known; some test strips contain absorbing sections that can accommodate a known volume of plasma, after the red cells are retained in another section of the test strip near the blood application site. In some cases, the hematocrit affects the plasma flow in test strips, and therefore correction for hematocrit may improve accuracy of the analyte measurement. In some systems, a pipette is used that is designed to aspirate a predetermined sample volume.

U.S. Pat. No. 6,750,053 to Opalsky et al and U.S. Pat. No. 7,682,833 to Miller et al disclose devices for rapidly metering samples. U.S. Pat. No. 6,750,053 describes a snap-shut seal and states (column 11 lines 16-19) that the "volume of the metered fluid sample is the volume of the holding chamber 20 between the orifice (48 in FIG. 5) in the wall of the holding chamber and the capillary stop 22." U.S. Pat. No. 7,682,833 discloses (column 23 lines 39-43) that the "location at which air enters the sample chamber (gasket hole 27) from the bladder, and the capillary stop 25, together define a predetermined volume of the sample chamber. An amount of the sample corresponding to this volume is displaced into the first conduit when paddle 6 is depressed." In the cases of U.S. Pat. No. 6,750,053 and U.S. Pat. No. 7,682,833, while the fluid sample is metered, the sample in the sample collection well (illustrated in U.S. Pat. No. 6,750,053 as element 12 in FIG. 3) is wasted.

Sample size is a major consideration for POCT systems, especially when it is desirable to use a small drop of blood obtained by puncturing the skin of a body part; the sample is referred to as a pin-prick sample. With some patients, it is difficult to obtain a small drop of blood, therefore there is a need to avoid any blood wastage. This is particularly true for neonatal blood testing.

Prothrombin Time (PT) is an example of a coagulation test, which requires a fixed sample volume. PT is usually reported as PT-INR (PT-International Normalized Ratio). The result for a prothrombin time performed on a normal individual will vary according to variations between different types and batches of thromboplastins used. The INR was devised to standardize the results using an ISI (International Sensitivity Index) value. Each manufacturer assigns an ISI value for any thromboplastin they manufacture. Another factor which affects PT-INR when using whole blood, as is the case of POCT, is the hematocrit. Only plasma contains coagulation factors, but a whole blood sample has a variable number of red cells mixed in, depending on the patient's hematocrit. These red cells take up space in the test cartridge. The coagulation factors that are being tested, are all in the liquid part of blood, i.e., the plasma. Because patients have different hematocrits, each patient sample adds a different amount of liquid plasma to the cartridge, but the amount of thromboplastin in the test cartridge is fixed. In a patient with low hematocrit, the excess plasma volume dilutes the reagent i.e., thromboplastin, and slows clot formation, resulting in a falsely increased PT-INR. PT-INR measured in the laboratory usually uses plasma, and plasma measurement of PT-INR is considered the gold standard. Therefore, whole blood PT-INR measurement will differ from the laboratory PT-INR measurement, which uses plasma. For POCT of PT-INR, correction can be made for an average hematocrit value, but errors in the PT-INR will increase as the hematocrit value moves away from the average hematocrit value. POCT of PT-INR usually use biosensors (also referred to as electrochemical detectors) that in many cases do not provide hematocrit measurement because the blood clots within seconds, after the blood is mixed with the thromboplastin.

U.S. Pat. No. 9,470,673 to Samsoondar, and application PCT/CA2017/050379, by Samsoondar, teach disposable cartridges for operation with a joint spectroscopic and biosensor blood analyzer. These publications teach a male-configured cartridge inlet, with the dual purposes of engaging a female-configured cap for sealing the inlet, and engaging a capillary adaptor for drawing blood into the cartridge by capillary action. The described combination of cap, capillary adaptor and inlet provides for dispensing blood from a syringe into the cartridge, as well as drawing capillary blood from a pin prick drop of blood on a patient's skin into the cartridge, for testing. U.S. Pat. No. 9,470,673 and PCT/CA2017/050379 do not teach how the inlet can engage a cap that is hingedly attached to the cartridge, to provide a sealed configuration having a closed air passage for connecting an air bladder to the blood storage conduit, in order to push blood from the sample well into the optical chamber, or into both the optical chamber and the biosensor chamber, using pressurized air from the air bladder. These documents also do not teach how the capillary adaptor as described, can be used when a cap is hingedly attached the body of the cartridge.

U.S. Pat. No. 7,108,833 to Samsoondar teaches a sample tab comprising a sample well having an inlet for receiving a blood sample, and a hinged cap for engaging with the inlet, wherein when the cap is engaged with the inlet after the sample is deposited in the sample well, the capped sample well becomes an optical chamber. U.S. Pat. No. 7,108,833 does not teach a blood flow channel.

U.S. Pat. No. 5,096,669 to Lauks teaches a disposable cartridge having a housing, a sample inlet, a hinged snap-on cap for sealing the inlet after drawing the sample into the cartridge by capillary action, and an air bladder. U.S. Pat. No. 5,096,669 does not teach an optical chamber.

A disposable cartridge for measuring a property of a sample is useful for point-of-care testing (POCT), and a disposable cartridge having a cap hingedly attached to a cartridge is safe and easy to operate, particularly when the POCT process is automated.

SUMMARY OF THE INVENTION

The invention relates to a disposable cartridge used for measuring a property of a sample. The disposable cartridge is useful for point-of-care testing (POCT).

As described herein there is provided a disposable cartridge comprising:
a cartridge body comprising an upper surface and a lower surface;
a sample inlet portion located on the upper surface, the sample inlet portion comprising:
 a sample storage well for storing a first portion of a sample, the sample storage well comprising a top portion for receiving a blood sample and a bottom portion for releasing at least some the blood sample into a sample storage conduit, wherein the top area is substantially larger than the bottom area;
 an air bladder exit port located on the upper surface,
 a flat surface of the cartridge body located on the upper surface, the flat surface of the cartridge body surrounding the top opening and the air bladder exit port;
 the sample storage conduit for transferring at least some of the blood from the sample storage well to an optical chamber;
 the optical chamber for generating signals during sample interrogation, the signals used to calculate the one or more properties of the blood sample;
 an air bladder for providing pressurized air, the air bladder operatively connected with the air bladder exit port;
 a vent in operative communication with the optical chamber, the vent for relieving pressure in the optical chamber;
 a cap hingedly connected to the cartridge body via a hinge, the cap having a top side and an underside, wherein at least a portion of the underside comprises a cap flat surface;
wherein, the cartridge is adjustable between an unsealed configuration and a sealed configuration by rotating the cap about the hinge, in the unsealed configuration the sample storage well is configured to receive the blood sample, and in the sealed configuration a portion of the flat surface of the cartridge body mates with a portion of the cap flat surface to form a closed air passage operatively connecting the air bladder exit port to the sample storage well so that pressurized air from the air bladder exit port is transferable to the sample storage well, and when the air bladder is squeezed blood is urged from the sample storage well towards the optical chamber, and wherein the closed air passage is facilitated by a groove set into the upper surface of the cartridge body, a recess set into the underside of the cap, or a combination thereof.

A disposable cartridge as describe above is also provided, wherein the top area is in a range of about 10 square millimeters to about 150 square millimeters, and the bottom area is in a range of about 0.01 square millimeters to about 10 square millimeters, or the top area is in a range of about 15 square millimeters to about 100 square millimeters, and the bottom area is in a range of about 0.05 square millimeters to about 5 square millimeters.

The disposable cartridge may further comprise means for mitigating blood flow out of the sample storage well, except when the air bladder is squeezed.

The disposable cartridge described above may further comprise a biosensor chamber disposed between an exit of the optical chamber and the vent, the biosensor chamber comprising one or more biosensors for generating signals used to calculate the one or more properties of the blood sample.

Additionally, the disposable cartridge may comprise a reagent chamber disposed in the sample storage conduit, with the reagent chamber containing at least one reagent, for example, the at least one reagent may be selected from dry thromboplastin, celite, and kaolin. The disposable cartridge may also comprise a mixing chamber disposed in the sample storage conduit. The sample inlet portion of the disposable cartridge may also comprise a sample overflow well for receiving excess sample.

The flat surface of the disposable cartridge may comprise a gasket that surrounds the top opening and the air bladder exit port. Alternatively, the cap flat surface may comprise a gasket. Furthermore, the cap may rotate about the hinge in a plane perpendicular to a plane defined by the upper surface, or the cap may rotate about the hinge in a plane parallel to a plane defined by the upper surface. The cap may comprise a sweeping edge for skimming off any excess of the sample from the sample inlet portion when the cartridge is adjusted from the unsealed configuration to the sealed configuration. Additionally, the cap may comprise a groove disposed at the underside of the cap, in front of the sweeping edge of the cap, for holding excess sample. The cap may comprise a means for securing the cap when the cartridge is in the sealed configuration.

Also described herein is a method (A) for measuring one or more properties of a blood sample in a disposable cartridge, wherein the cartridge is adjustable between an unsealed configuration and a sealed configuration, the method comprising:
  i) depositing the blood sample into a sample storage well of the disposable cartridge in the unsealed configuration, the disposable cartridge comprising:
    a cartridge body having an upper surface and a lower surface;
    a sample inlet portion located on the upper surface, the sample inlet portion comprising:
      a sample storage well for storing a first portion of a sample, the sample storage well comprising a top portion for receiving a blood sample and a bottom portion for releasing at least some the blood sample into a sample storage conduit, wherein the top area is substantially larger than the bottom area;
      an air bladder exit port located on the upper surface,
      a flat surface of the cartridge body located on the upper surface, the body flat surface surrounding the top opening and the air bladder exit port;
    an air bladder for providing pressurized air and operatively connected with the air bladder exit port;
    a cap hingedly connected to the cartridge body via a hinge, the cap having a top side and an underside, wherein at least a portion of the underside comprises a cap flat surface, the cartridge adjustable between the unsealed configuration and the sealed configuration by rotating the cap about the hinge;
    a detection chamber disposed downstream from the bottom opening, the detection chamber for generating signals from the blood sample;
    a detection chamber exit operatively connected to the detection chamber; and
    a vent in fluid communication with the detection chamber exit, the vent for relieving pressure in the detection chamber;
  ii) adjusting the cartridge from the unsealed configuration to the sealed configuration by rotating the cap about the hinge, wherein in the sealed configuration, a portion of the flat surface of the cartridge body and a portion of the cap flat surface mate to provide a closed air passage operatively connecting the air bladder exit port to the sample storage well, wherein the closed air passage is facilitated by a groove set into the flat surface of the cartridge body, a recess set into the underside of the cap, or a combination thereof;
  iii) providing an analyzer comprising:
    a receptor for receiving the cartridge;
    one or more than one processor for controlling the analyzer;
    means for squeezing the air bladder;
    a source of electromagnetic radiation for interrogating the blood in the optical chamber; and
    one or more detectors for receiving the signals generated from the blood in detection chamber;
  iv) inserting the disposable cartridge in the sealed configuration, into the receptor of the analyzer;
  v) squeezing the air bladder to provide pressurized air to the closed air passage, for urging blood out of the sample storage well and stopping a leading edge of the blood at a position between the detection chamber exit and the vent; and
  vi) sending the signals generated from the blood in the detection chamber to the one or more than one processor for transforming the signals into the one or more properties of the blood sample.

A method (B) for measuring a plurality of properties of a blood sample in a disposable cartridge, wherein the disposable cartridge is adjustable between an unsealed configuration and a sealed configuration is also provided herein. The method comprising:
  i) depositing the blood sample into a sample storage well of the disposable cartridge in the unsealed configuration, the disposable cartridge comprising:
    a cartridge body having an upper surface and a lower surface;
    a sample inlet portion located on the upper surface, the sample inlet portion comprising:
      a sample storage well for storing a first portion of a sample, the sample storage well comprising a top portion for receiving a blood sample and a bottom portion for releasing at least some the blood sample into a sample storage conduit, wherein the top area is substantially larger than the bottom area;
      an air bladder exit port located on the upper surface,
      a flat surface of the cartridge body located on the upper surface, the flat surface of the cartridge body surrounding the top opening and the air bladder exit port;
    an air bladder for providing pressurized air and operatively connected with the air bladder exit port;
    a cap hingedly connected to the cartridge body via a hinge, the cap having a top side and an underside, wherein at least a portion of the underside comprises a cap flat surface;
    an optical chamber disposed downstream from the bottom opening, the optical chamber for generating a first set of signals from the blood sample;
    an optical chamber exit operatively connected to the optical chamber;
    a biosensor chamber for generating a second set of signals, the biosensor chamber disposed between the optical chamber exit and a vent;
    a biosensor chamber entrance operatively connected to the biosensor chamber;
    a biosensor chamber exit, operatively connected to the biosensor chamber; and
    the vent in operative communication with the biosensor chamber; the vent for relieving pressure in the biosensor chamber;
    wherein
  ii) adjusting the cartridge from the unsealed configuration to the sealed configuration by rotating the cap about the hinge, wherein in the sealed configuration a portion of the flat surface of the cartridge body and a portion of the cap flat surface mate to provide a closed air passage operatively connecting the air bladder exit port to the sample storage well, wherein the closed passage is facilitated by a groove set into the flat surface of the cartridge body, a recess set into the underside of the cap, or a combination thereof;

iii) providing an analyzer comprising:
a receptor for receiving the cartridge;
one or more than one processor for controlling the analyzer;
means for squeezing the air bladder;
a source of electromagnetic radiation for interrogating the blood in the optical chamber; and
a plurality of detectors for receiving the first set; the second set, or both the first and second set, of signals generated from the blood in the optical chamber and the blood in the biosensor chamber;

iv) inserting the disposable cartridge in the sealed configuration, into the receptor of the analyzer; and
if biosensor calibration is required;
v-1a) squeezing the air bladder to provide pressurized air to the closed air passage, for urging the blood out of the sample storage well into the optical chamber, and stopping a leading edge of the blood at a position between the optical chamber exit and the biosensor chamber entrance;
v-1b) calibrating the one or more biosensors prior to urging the blood into the biosensor chamber, and stopping the leading edge of the blood between the biosensor chamber exit and the cartridge vent; and
v-1c) stopping the leading edge of the blood at a position between the biosensor chamber exit and the cartridge vent;
or
if biosensor calibration is not required,
v-2) urging the blood into the optical chamber and the biosensor chamber and stopping a leading edge of the blood at a position between the biosensor chamber exit and the cartridge vent;

vi) sending the first set, the second set, or both the first and the second set of signals generated from the blood in the optical chamber and the blood in the biosensor chamber to the one or more than one processor for transforming the first set, the second set, or both the first and the second set of signals into the plurality of properties of the blood sample.

Other aspects and features of the present invention will become apparent, to those having ordinary skill in the art, upon review of the following description of specific embodiments of the invention, which are provided as examples.

BRIEF DESCRIPTION OF THE DRAWINGS

A better understanding of the novel features and advantages of the present invention will be made by reading the detailed description of the preferred embodiments provided later, in conjunction with the accompanying drawings, in which:

FIG. 1A is an exploded top perspective view of disposable cartridge 10 for measuring a property of a sample, the cartridge having a rapid sample metering system, according to a first embodiment of the cartridge;

FIG. 1B is a bottom view of the first housing member 20 of the cartridge shown in FIG. 1A;

FIG. 1C is the bottom view of the first housing member 20 of the cartridge shown in FIG. 1B, overlaid by and in alignment with the gasket 100 shown in FIG. 1A;

FIG. 1D is a top view of the second housing member 30 of the cartridge shown in FIG. 1A;

FIG. 1E is the top view of the second housing member 30 shown in FIG. 1D, overlaid by and in alignment with the gasket 100 shown in FIG. 1A;

FIG. 1F is a top view of the cartridge 10 shown in FIG. 1A, with the cap 50 in a fully closed position;

FIG. 1G is a first enlarged cross-sectional view through the cartridge shown in FIG. 1F along line G-G;

FIG. 1H is a second enlarged cross-sectional view through the cartridge shown in FIG. 1F along line H-H;

FIG. 1J is a third enlarged cross-sectional view through the cartridge shown in FIG. 1F along line J-J;

FIG. 3A is a perspective view of the cartridge 10 shown in FIG. 2A, with air bladder 340 open;

FIG. 3B is a detailed view of detail B of the cartridge shown in FIG. 3A, showing details of the sample inlet portion 40;

FIG. 3C is a perspective top view of the cartridge 10 shown in FIG. 2D;

FIG. 3D is a detailed view of detail D of the cartridge shown in FIG. 3C;

FIG. 5A is an exploded top perspective view of the disposable cartridge 10b for measuring a property of a sample, the cartridge having a rapid sample metering system, according to a second embodiment of the cartridge;

FIG. 5B is a bottom view of the first housing member 20b of the cartridge shown in FIG. 5A;

FIG. 5C is the bottom view of the first housing member 20b shown in FIG. 5B, overlaid by and in alignment with the gasket 100b shown in FIG. 5A;

FIG. 5D is a top view of the second housing member 30b of the cartridge shown in FIG. 5A;

FIG. 5E is the top view of the second housing member 30b shown in FIG. 5D, overlaid by and in alignment with the gasket 100b shown in FIG. 5A;

FIG. 7A is a perspective top view of the cartridge 10b (with the cap 50b removed shown in FIG. 6A;

FIG. 7B is a detailed view of detail B of the cartridge shown in FIG. 7A, showing details of the sample inlet portion 40b;

FIG. 7C is a perspective top view of the cartridge 10b shown in FIG. 6D;

FIG. 7D is a detailed view of detail D of the cartridge shown in FIG. 70;

FIG. 8A is a top view of the cap 50b shown in FIG. 7C;

FIG. 8B is a perspective top view of the cap 50b shown in FIG. 8A;

FIG. 8C is a front view of the cap 50b shown in FIG. 8A;

FIG. 8D is a right side view of the cap 50b shown in FIG. 8A;

FIG. 8E is a bottom view of the cap 50b shown in FIG. 8A;

FIG. 8F is a perspective bottom view of the cap 50b shown in FIG. 8E;

FIG. 8G is a cross-sectional view through the cap 50b shown in FIG. 8E along line G-G;

FIG. 9A is an exploded top view of the disposable cartridge 10c for measuring a property of a sample, the cartridge having a rapid sample metering system, according to a third embodiment of the cartridge;

FIG. 9B is a bottom view of the first housing member 20c of the cartridge shown in FIG. 9A;

FIG. 9C is the bottom view of the first housing member 20c shown in FIG. 9B, overlaid by and in alignment with the gasket 100c shown in FIG. 9A;

FIG. 9D is a top view of the second housing member 30c of the cartridge shown in FIG. 9A;

FIG. 9E is the top view of the second housing member 30c shown in FIG. 9D, overlaid by and in alignment with the gasket 100c shown in FIG. 9A;

FIG. 9F is a top view of the cartridge 10c shown in FIG. 9A, with the cap 50c in a fully closed and latched position;

FIG. 9G is a front view of the cartridge 10c shown in FIG. 9F;

FIG. 9H is a bottom view of the cartridge 10c shown in FIG. 9F, with bottom cover 351c removed to expose the sample storage conduit groove 85c;

FIG. 9J is a perspective top view of the cartridge 10c shown in FIG. 9F;

FIG. 9K is the perspective top view of the cartridge 10c shown in FIG. 9J. with the cap 50c and latch 70c removed;

FIG. 9L is a top view of the cartridge 10c shown in FIG. 9A, with the cap 50c in a fully open position;

FIG. 11A is a top view of the cartridge 10c (similar to the view shown in FIG. 9F) with the cap 50c in a fully closed position, for illustrating the internal structure;

FIG. 11B is a first enlarged cross-sectional view through the cartridge 10c shown in FIG. 11A along line B-B;

FIG. 11C is a second enlarged cross-sectional view through the cartridge 10c shown in FIG. 11A along line C-C;

FIG. 11D is a third enlarged cross-sectional view through the cartridge 10c shown in FIG. 11A along line D-D;

FIG. 11E is a fourth enlarged cross-sectional view through the cartridge 10c shown in FIG. 11A along line E-E;

FIG. 14A is an exploded top view of the disposable cartridge 10e in an open configuration, for measuring a property of a sample, according to a fifth embodiment of the cartridge;

FIG. 14B is a bottom view of the first housing member 20e of the cartridge shown in FIG. 14A;

FIG. 14C is the bottom view of the first housing member 20e of the cartridge shown in FIG. 14B, overlaid by and in alignment with the gasket 100e shown in FIG. 14A;

FIG. 14D is a top view of the second housing member 30e of the cartridge shown in FIG. 14A;

FIG. 14E is the top view of the second housing member 30e shown in FIG. 14D, overlaid by and in alignment with the gasket 100e shown in FIG. 14A;

FIG. 15A is a perspective top view of the cartridge 10e in a closed configuration;

FIG. 15B is a perspective top view of the cartridge 10e in an open configuration;

FIG. 15C is a top view of the cartridge 10e in a closed configuration;

FIG. 15D is a first cross-sectional view through the cartridge 10e shown in FIG. 15C along line D-D;

FIG. 15E is a detailed view of detail E of the cartridge shown in FIG. 15D;

FIG. 15F is a second cross-sectional view through the cartridge 10e shown in FIG. 15C along line F-F;

FIG. 15G is a detailed view of detail G of the cartridge shown in FIG. 15F;

FIG. 15H is a top view of the cartridge 10*e*, with the cap hidden;

FIG. 16A is an exploded top view of the disposable cartridge 10*f* in an open configuration, for measuring a property of a sample, according to a sixth embodiment of the cartridge;

FIG. 16B is a bottom view of the first housing member 20*f* of the cartridge shown in FIG. 16A;

FIG. 16C is the bottom view of the first housing member 20*f* of the cartridge shown in FIG. 16*6*, overlaid by and in alignment with the gasket 100*f* shown in FIG. 16A;

FIG. 16D is a top view of the second housing member 30*f* of the cartridge shown in FIG. 16A;

FIG. 16E is the top view of the second housing member 30*f* shown in FIG. 16D, overlaid by and in alignment with the gasket 100*f* shown in FIG. 16A;

FIG. 17A is a perspective top view of the cartridge 10*f* in a closed configuration;

FIG. 17B is a perspective top view of the cartridge 10*f* in an open configuration;

FIG. 17C is a top view of the cartridge 10*f* in a closed configuration;

FIG. 17D is a first cross-sectional view through the cartridge 10*f* shown in FIG. 17C along line D-D;

FIG. 17E is a detailed view of detail E of the cartridge shown in FIG. 17D;

FIG. 17F is a second cross-sectional view through the cartridge 10*e* shown in FIG. 17C along line F-F;

FIG. 17G is a detailed view of detail G of the cartridge shown in FIG. 17F;

FIG. 19A is a perspective top view of the cartridge 10*g* in a closed configuration;

FIG. 19B is a perspective top view of the cartridge 10*g* in an open configuration;

FIG. 19C is a top view of the cartridge 10*g* in a closed configuration;

FIG. 19D is a first cross-sectional view through the cartridge 10*g* shown in FIG. 19C along line D-D;

FIG. 19E is a detailed view of detail E of the cartridge shown in FIG. 19D:

FIG. 19F is a second cross-sectional view through the cartridge 10*g* shown in FIG. 19C along line F-F;

FIG. 19G is a detailed view of detail G of the cartridge shown in FIG. 19F; and

Figure 2A:
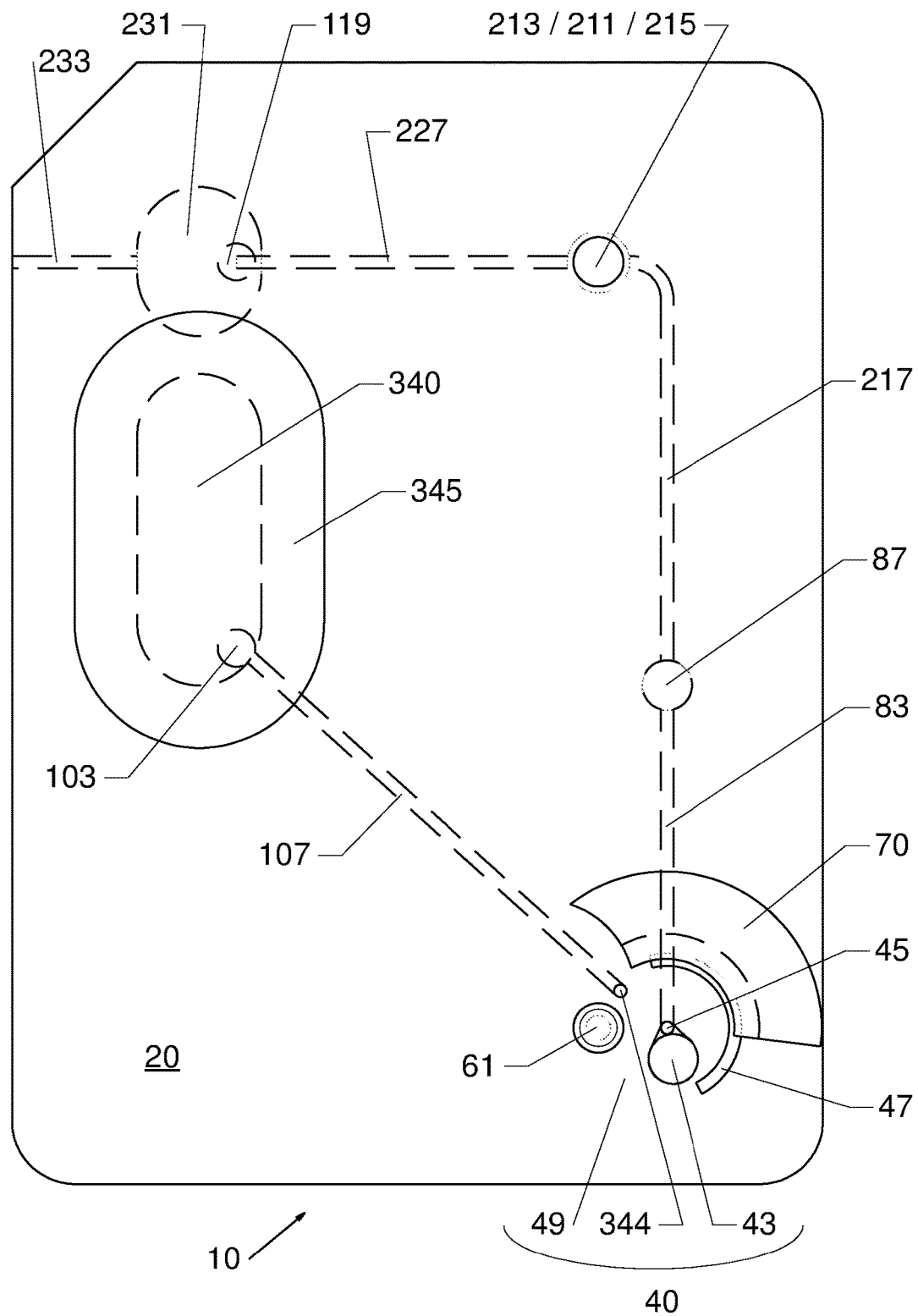
FIG. 2A is a top view of the cartridge 10 shown collectively in FIGS. 1A-1J, with the cap 50 and pin 60 removed.

For a better understanding of the present invention; and to show more clearly how it may be carried into effect, reference will now be made, by way of example, to the accompanying drawings, and which are described in the following detailed description of preferred aspects of the invention.

DETAILED DESCRIPTION OF PREFERRED ASPECTS OF THE INVENTION

A disposable cartridge for measuring a property of a sample is described. The disposable cartridge is useful for point-of-care testing (POCT). The disposable cartridge provides for automatic sample volume metering so that after applying an unknown sample volume to the cartridge, a specific volume of the sample is used for measuring the property of the sample.

For example, and as described in detail below, the disposable cartridge may comprise a cartridge body having an upper surface and a lower surface, a cap hingedly (or pivotally) connected to the cartridge body by a pin or hinge so that the cap is positioned on the upper surface of the cartridge body. The cap comprises a top side and an underside, with the underside comprising a cap recess surrounded by a flat surface (also referred to as a cap flat surface). The disposable cartridge further comprises a sample inlet portion located on the upper surface of the cartridge body. The sample inlet portion including:

a sample storage well for storing a first portion of a sample, the sample storage well comprising a top surface that defines a top opening (also termed a top portion), for receiving the sample and a bottom portion (a bottom opening defined by the cartridge body) for releasing a second portion of the sample to a sample storage conduit;

an air bladder exit port;

and a flat surface (also referred to as a body flat surface) surrounding the sample storage well and the air bladder exit port, the body flat surface for engaging the flat surface of the underside of the cap. Regarding the fifth, sixth and seventh embodiments of a cartridge, and depending on the wettability of the sample storage well and the sample storage conduit, all the sample may be stored in the sample storage well In embodiments one to four and seven described below, the cap includes a sweeping edge that may be used to skim off any excess of the sample when received by the sample storage well, the sample inlet portion or both, when the cap is pivotally rotated from an open position where the cartridge is in an unsealed configuration, to a closed positioned where the cartridge is in a sealed configuration. The sample storage conduit is in fluid communication between the bottom opening of the sample well and a capillary break, and is used to receive the second portion of the sample. The total volume of the sample in the cartridge, when in the sealed configuration, is equivalent to the volume measured from the top opening of the sample storage well to the capillary break. The cartridge body further comprises a detection chamber in fluid communication with the capillary break and the sample storage conduit (via a detection chamber inlet conduit). The detection chamber is for receiving a portion of the total volume of the sample from the sample storage conduit and for generating a signal during sample interrogation, the signal used to calculate a property of the sample. The cartridge body also comprises a vent in fluid communication with the detection chamber, the vent for relieving pressure in the detection chamber, and an air bladder in fluid communication with the air bladder exit port. When the disposable cartridge is in the unsealed configuration, the sample storage well is open and available to receive the sample. When in the sealed configuration and the cap is in a closed position, the cap recess facilitates provision of a closed air passage connecting the air bladder exit port and the sample storage well for communicating pressurized air from the air bladder to the sample storage well via the air bladder exit port, so that when the air bladder is pressed or squeezed, the volume of the sample, or a portion thereof, is urged from the sample storage conduit into the detection chamber.

In embodiments five and six as described below (see FIGS. 14 to 17), the cap is hingedly attached so that the cap rotates vertically with reference to a plane orthogonal to the plane defined by the body flat surface surrounding the sample storage well and the air bladder exit port of the cartridge, as opposed to the horizontal motion with reference with reference to a plane defined by the body flat surface surrounding the sample storage well and the air bladder exit port as described with reference to embodiments one to four and seven (see FIGS. 1 to 13, 18 and 19). In embodiments five and six, an air bladder is used to regulate the volume of the blood released from the sample storage well. In embodiments one to four and seven, the air bladder is used to regulate the distance from the vent that the front end of the blood is allowed to flow.

Also described herein is a method for measuring a property of a blood sample. The method comprises depositing a blood sample into the sample storage well of the disposable cartridge as defined herein, the disposable cartridge in the unsealed configuration. In some cartridges, the cartridge cap is rotated horizontally (with reference to a plane defined by the flat surface surrounding the sample storage well and the air bladder exit port of the cartridge) about the pin which skims off excess blood and places the disposable cartridge in the sealed configuration to produce a sealed cartridge that comprises the volume of the sample. In other cartridges, the cartridge cap rotates vertically with reference to a plane defined by the flat surface surrounding the sample storage well and the air bladder exit port of the cartridge. In cartridges comprising a vertically rotating cap, the surface of the blood sample deposited in the sample storage well is not skimmed off, and the volume of the deposited sample used is regulated by controlling the extent to which the air bladder is squeezed. The sealed cartridge is inserted into a receptor of an analyzer, the analyzer comprising the receptor for receiving the disposable cartridge, one or more than one processor for controlling the analyzer; means for activating the air bladder; and a detector for receiving the signal from the detection chamber and sending the signal to the one or more than one processor for transforming the signal into the property of the sample. Once inserted into the receptor, the air bladder is activated and provides the pressurized air so that some of the sample moves through one of the detection chamber inlet conduit. The cartridge may contain at least one reagent, and a reagent chamber, containing the at least one reagent. If the cartridge contains at least one reagent, then the at least one reagent is dissolved in the blood to produce a mixture of the blood and the at least one reagent. The blood, or the mixture of blood, and the at least one reagent, is urged into the detection chamber and the property of the blood sample is measured in the detection chamber using the analyzer.

As used herein, the terms "comprising," "having," "including" and "containing," and grammatical variations thereof, are inclusive or open-ended and do not exclude additional, un-recited elements and/or method steps. The term "consisting essentially of" when used herein in connection with a use or method, denotes that additional elements and/or method steps may be present, but that these additions do not materially affect the manner in which the recited method or use functions. The term "consisting of" when used herein in connection with a use or method, excludes the presence of additional elements and/or method steps. A use or method described herein as comprising certain elements and/or steps may also, in certain embodiments consist essentially of those elements and/or steps, and in other embodiments consist of those elements and/or steps, whether or not these embodiments are specifically referred to. In addition, the use of the singular includes the plural, and "or" means "and/or" unless otherwise stated. The term "plurality" as used herein means more than one, for example, two or more, three or more, four or more, and the like. Unless otherwise defined herein, all technical and scientific terms used herein have the same meaning as commonly understood by one of ordinary skill in the art. As used herein, the term "about" refers to an approximately +/−25% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

The terms "operatively connected" or "in operative communication" and the like, describe elements of the disposable cartridge, for example, channels, conduits, tunnels, passageways, that permit either fluid flow, gas flow, or both fluid and gas flow between the various compartments or elements within the disposable cartridge that are connected by the channels, conduits, tunnels, passageways and the like.
Disposable Cartridges with a Rapid Sample Metering System Detailed description of novel features of examples of the invention is discussed now, and is best understood with reference to the accompanying drawings. These examples are to be considered non-limiting, and a person of ordinary skill in the art will understand that variations are within the scope of the invention, even though they are not explicitly illustrated. The same reference numerals are used for similar elements in different examples; in some cases, letters are appended to the end of the reference numerals to denote the embodiment of the invention illustrated. For example, the letters "b" (FIGS. 5-8), "c" (FIGS. 9-11), "d" (FIGS. 12-13), "e" (FIGS. 14-15), "f" (FIGS. 16-17), and "g" (FIGS. 18-19) are used to refer to the $2^{nd}$, $3^{rd}$, $4^{th}$, $5^{th}$, $6^{th}$ and $7^{th}$ embodiments or examples of the invention, respectively. It should be noted that absence of a letter after a reference numeral does not imply that the element belongs to the first example of the invention. For easy reference, Table 1 provides a list of the reference numerals used, and a brief description of the corresponding structural features.

TABLE 1

Description of Structural Features.

| Reference Numerals | Description of Structural Features |
|---|---|
| 10 | A first embodiment of a cartridge |
| 10b | A second embodiment of a cartridge |
| 10c | A third embodiment of a cartridge |
| 10d | A fourth embodiment of a cartridge |
| 10e | A fifth embodiment of a cartridge |
| 10f | A sixth embodiment of a cartridge |
| 10g | A seventh embodiment of a cartridge |

TABLE 1-continued

Description of Structural Features.

| Reference Numerals | Description of Structural Features |
|---|---|
| 20 | First housing member of cartridge 10 |
| 20b | First housing member of cartridge 10b |
| 20c | First housing member of cartridge 10c |
| 20d | First housing member of cartridge 10d |
| 20e | First housing member of cartridge 10e |
| 20f | First housing member of cartridge 10f |
| 20g | First housing member of cartridge 10g |
| 30 | Second housing member of cartridge 10 |
| 30b | Second housing member of cartridge 10b |
| 30c | Second housing member of cartridge 10c |
| 30d | Second housing member of cartridge 10d |
| 30e | Second housing member of cartridge 10e |
| 30f | Second housing member of cartridge 10f |
| 30g | Second housing member of cartridge 10g |
| 40 | A sample inlet portion of cartridge 10, which comprises some elements of the cartridge that interact with the cap 50 |
| 40b | A sample inlet portion of cartridge 10b, which comprises some elements of the cartridge that interact with the cap 50b |
| 40c | A sample inlet portion of cartridge 10c, which comprises some elements of the cartridge that interact with the cap 50c |
| 40d | A sample inlet portion of cartridge 10d, which comprises some elements of the cartridge that interact with the cap 50d |
| 40e | A sample inlet portion of cartridge 10e, which comprises some elements of the cartridge that interact with the cap 50e |
| 40f | A sample inlet portion of cartridge 10df which comprises some elements of the cartridge that interact with the cap 50f |
| 40g | A sample inlet portion of cartridge 10g, which comprises some elements of the cartridge that interact with the cap 50g |
| 41 | A sample storage well of an inlet portion 40 of cartridge 10 |
| 41b | A sample storage well of an inlet portion 40b of cartridge 10b |
| 41d | A sample storage well of an inlet portion 40d of cartridge 10d |
| 41e | A sample storage well of an inlet portion 40e of cartridge 10e |
| 41f | A sample storage well of an inlet portion 40f of cartridge 10f |
| 41g | A sample storage well of an inlet portion 40g of cartridge 10g |
| 43 | Top opening (or top portion) of a sample storage well 41 of cartridge 10 |
| 43b | Top opening (or top portion) of a sample storage well 41b of cartridge 10b |
| 43c | Top opening (or top portion) of a sample storage well of cartridge 10c |
| 43d | Top opening (or top portion) of a sample storage well 41d of cartridge 10d |
| 43e | Top opening (or top portion) of a sample storage well 41d of cartridge 10e |
| 43f | Top opening (or top portion) of a sample storage well 41d of cartridge 10f |
| 43g | Top opening (or top portion) of a sample storage well 41d of cartridge 10g |
| 45 | Bottom opening (or bottom portion) of sample storage well 41 of cartridge 10 |
| 45b | Bottom opening (or bottom portion) of sample storage well 41b of cartridge 10b |
| 45d | Bottom opening (or bottom portion) of sample storage well 41d of cartridge 10d |
| 45c | Bottom opening (or bottom portion) of sample storage well of cartridge 10c |
| 45d | Bottom opening (or bottom portion) of sample storage well of cartridge 10d |
| 45e | Bottom opening (or bottom portion) of sample storage well 41e of cartridge 10e |
| 45f | Bottom opening (or bottom portion) of sample storage well 41f of cartridge 10f |
| 45g | Bottom opening (or bottom portion) of sample storage well 41g of cartridge 10g |
| 46 | Enlarge cavity near the bottom opening 45e of sample storage well 41e of cartridge 10e, for providing means for mitigating blood flow out of the sample storage well 41e, except when the air bladder 340e is squeezed |
| 47 | A sample overflow well of an inlet portion 40 of cartridge 10 |
| 47b | A sample overflow well of an inlet portion 40b of cartridge 10b |
| 47g | A sample overflow well of an inlet portion 40g of cartridge 10g |
| 48c | Groove disposed at the underside and at the sweeping portion of the cap 50c of cartridge 10c, for storing excess sample |
| 48d | Groove disposed at the underside and at the sweeping portion of the cap 50d, for storing excess sample |
| 49 | A sliding surface of inlet portion 40 of cartridge 10, surrounding sample storage well 41 |
| 49b | A sliding surface of inlet portion 40b of cartridge 10b, surrounding sample storage well 41b |
| 49c | A sliding surface of inlet portion 40c of cartridge 10c, surrounding sample storage well 41c |
| 49d | A sliding surface of inlet portion 40d of cartridge 10d, surrounding sample storage well 41d |
| 49e | A flat surface of inlet portion 40e surrounding top opening 43e of a sample storage well 41e and the air bladder exit port 344e of cartridge 10e |
| 49f | A flat surface of inlet portion 40f surrounding the sample storage well and the air bladder exit port of cartridge 10f |
| 49g | A flat surface of inlet portion 40g surrounding the sample storage well and the air bladder exit port of cartridge 10g |
| 50 | A cap for closing inlet portion 40 of cartridge 10 |
| 50b | A cap for closing inlet portion 40b of cartridge 10b |
| 50c | A cap for closing inlet portion 40c of cartridge 10c |
| 50d | A cap for closing inlet portion 40d of cartridge 10d |
| 50e | A cap for closing inlet portion 40e of cartridge 10e |
| 50f | A cap for closing inlet portion 40f of cartridge 10f |
| 50g | A cap for closing inlet portion 40g of cartridge 10g |
| 51 | Top side of cap 50 of cartridge 10 |
| 51b | Top side of cap 50b of cartridge 10b |
| 51e | Top side of cap 50e of cartridge 10e |
| 51f | Top side of cap 50f of cartridge 10f |
| 51g | Top side of cap 50g of cartridge 10g |
| 52 | Underside of cap 50 of cartridge 10 |
| 52b | Underside of cap 50b of cartridge 10b |
| 52e | Underside of cap 50e of cartridge 10e |
| 52f | Underside of cap 50f of cartridge 10f |
| 53 | A sweeping portion of cap 50 of cartridge 10 |
| 53b | A sweeping portion of cap 50b of cartridge 10b |
| 53c | A sweeping portion of cap 50c of cartridge 10c |
| 54 | A trailing portion of cap 50 of cartridge 10 |
| 54b | A trailing portion of cap 50b of cartridge 10b |
| 54c | A trailing portion of cap 50c of cartridge 10c |
| 55 | Cap recess in the underside of cap 50 of cartridge 10 |
| 55b | Cap recess in the underside of cap 50b of cartridge 10b |
| 55c | Cap recess in the underside of cap 50c of cartridge 10c |
| 55d | Cap recess in the underside of cap 50d of cartridge 10d |
| 55e | Channel in body of cartridge 10e for facilitating formation of a closed passage for connecting the air bladder exit port 344e to the sample storage well 41e |
| 55f | Cap recess in the underside 52f of cap 50f of cartridge 10f for facilitating formation of a closed passage for connecting the air bladder exit port 344f to the sample storage well 41f |
| 55g | Cap recess in the underside of cap 50g of cartridge 10g for facilitating formation of a closed passage for connecting the air bladder exit port 344g to the sample storage well 41g |
| 57 | A cap sealing ring/washer (referred to as a gasket or seal in some embodiments) in cap 50 of cartridge 10 |
| 57c | A cap sealing gasket in cap 50c of cartridge 10c |
| 57d | A cap sealing gasket in cap 50d of cartridge 10d |
| 57e | A cap sealing gasket in the body of cartridge 10e |
| 57f | A cap sealing gasket in cap 50f of cartridge 10f |
| 57g | A cap sealing gasket in cap 50g of cartridge 10g |
| 58 | A sweeping cap edge disposed at the sweeping portion 53 of cap 50 for skimming off excess sample |
| 58b | A sweeping cap edge disposed at the sweeping portion 53b of cap 50b for skimming off excess sample |
| 58c | A sweeping cap edge disposed at the sweeping portion 53c of cap 50c for skimming off excess sample |
| 58d | A sweeping cap edge disposed at the sweeping portion of cap 50d for skimming off excess sample |
| 59 | A cap handle for facilitating rotation of cap 50 |
| 60 | A pin for hingedly (or pivotally) attaching the cap 50 to the sample inlet portion 40 and allowing the cap to swing with the cap sealing ring/washer 57 frictionally engaged with the surface 49 (see FIG. 2A) of inlet portion 40. |

TABLE 1-continued

Description of Structural Features.

| Reference Numerals | Description of Structural Features |
|---|---|
| | Note: The term pivot is used to describe the pin or shaft 62c used with latch 70c. The attachment mechanism illustrated in FIG. 6F is optionally the same for the two hinged attachments. |
| 60b | A pin in cap 50b for hingedly attaching the cap to the sample inlet portion 40b and allowing the cap to swing with the non-recessed portion of the underside of the cap frictionally engaged with the surface 49b of inlet portion 40b |
| 60c | A pin in cap 50c for hingedly attaching the cap to the sample inlet portion 40c and allowing the cap to swing with the gasket 57c frictionally engaged with the surface 49c of inlet portion 40c |
| 60d | A pin in cap 50d for hingedly attaching the cap to the sample inlet portion 40d and allowing the cap to swing with the gasket 57d frictionally engaged with the surface 49d of inlet portion 40d |
| 60e ' and 60e " | Hinges for hingedly attaching cap 50e to the body of cartridge 10e |
| 60f ' and 60f " | Hinges for hingedly attaching cap 50f to the body of cartridge 10f |
| 60g | Pin for hingedly attaching cap 50g to body of cartridge 10g |
| 61 | A pin hole in first housing member for receiving pin 60 |
| 61b | A pin hole for receiving pin 60b |
| 61c | A pin hole for receiving pin 60c |
| 61e ' and 61e " | Holes for anchoring hinges 60e ' and 60e " for hingedly attaching cap 50e to body of cartridge 10e |
| 61f ' and 61f " | Holes for anchoring hinges 60f ' and 60f " for hingedly attaching cap 50f to body of cartridge 10f |
| 61g | A pin hole for receiving pin 60g for hingedly attaching cap 50g to body of cartridge 10g |
| 62c | Pivot of latch 70c |
| 63 | Bottom of pin hole 61 |
| 63b | Bottom of pin hole 61b |
| 63c | Bottom of pin hole 61c |
| 64c | Hole for receiving pivot 62c of latch 70c of cartridge 10c |
| 65b | Snap fit lip in pin 60b for locking pin 60b in pinhole 61b |
| 66c | Bottom of pivot hole 64c |
| 67b | Snap fit lip in pinhole 61b for locking pin 60b in pinhole 61b |
| 70 | Cap latch near inlet portion 40 |
| 70b | Cap latch near inlet portion 40b |
| 70c | Cap latch near inlet portion 40c |
| 70g | Cap latch near inlet portion 40g |
| 71 | Pin hole in cap 50 for receiving pin 60 |
| 72 | Cap stop for keeping cartridge 10d in either an unsealed configuration or a sealed configuration |
| 73 | Cap latch recess in cap latch 70 of cartridge 10 |
| 73b | Cap latch recess in cap latch 70b of cartridge 10b |
| 73g | Cap latch recess in cap latch 70g of cartridge 10g, for engaging cap 50g |
| 74e | Cap 50e latch catch for engaging cap latch 75e |
| 74f | Cap 50f latch catch for engaging cap latch 75f |
| 75e | Cap 50e latch |
| 75f | Cap 50f latch |
| 81 | A sample storage conduit entrance of a cartridge 10 |
| 81b | A sample storage conduit entrance of a cartridge 10b |
| 81c | A sample storage conduit entrance of a cartridge 10c |
| 82 | Hydrophobic insert disposed at the entrance of sample storage conduit 83f for providing means for mitigating blood flow out of the sample storage well, except when the air bladder is squeezed |
| 83 | A sample storage conduit of a cartridge 10 (see FIG. 1G) |
| 83b | A sample storage conduit of a cartridge 10b (see FIG. 5G) |
| 83c | A sample storage conduit of a cartridge 10c (see FIG. 11B) |
| 83d | A sample storage conduit of a cartridge 10c (see FIG. 12D) |
| 83e | A sample storage conduit of a cartridge 10e |
| 83f | A sample storage conduit of a cartridge 10f |
| 83g | A sample storage conduit of a cartridge 10g |
| 84c | Junction of sample storage conduit 83c and capillary break 87c of cartridge 10c (see FIG. 11B) |
| 85 | A sample storage conduit groove of a cartridge 10 |
| 85b | A sample storage conduit groove of a cartridge 10b |
| 85c | A sample storage conduit groove of a cartridge 10c (see FIG. 9H) |
| 86e | Blood shunt for bypassing optical chamber 211e, and providing fluid connection between sample storage well 41e and biosensor conduit 337e |
| 86f | Blood shunt for bypassing optical chamber 211f, and providing fluid connection between sample storage well 41f and biosensor conduit 337f |
| 86g | Blood shunt for bypassing optical chamber 211g, and providing fluid connection between sample storage well 41g and biosensor conduit 337g |
| 87' | Portion of a capillary break in a first housing member of cartridge 10 |
| 87" | Portion of a capillary break in a second housing member of cartridge 10 |
| 87 | A capillary break of a cartridge, comprising portions 87', 87", and a gasket cut-out 115 aligned with portions 87' and 87" |
| 87b' | Portion of a capillary break in a first housing member of cartridge 10b |
| 87b" | Portion of a capillary break in a second housing member of cartridge 10b |
| 87b | A capillary break of a cartridge, comprising portions 87b', 87b", and a gasket cut-out 115b aligned with portions 87b' and 87b" |
| 87c | A capillary break of cartridge 10c (see FIG. 11E) |
| 87c" | Portion of a capillary break 87 in a second housing member 30c of cartridge 10c |
| 88 | A mixing chamber entrance groove of cartridge 10b (see FIG. 5B) |
| 89 | A mixing chamber of a cartridge 10b (see FIG. 5G) |
| 89c | A mixing chamber of a cartridge 10c |
| 89c' | Portion of mixing chamber 89c in a first housing member 20c of cartridge 10c |
| 89c" | Portion of mixing chamber 89c in a second housing member 30c of cartridge 10c |
| 91b | A post capillary break conduit for providing fluid communication between the capillary break 87b and the mixing chamber 89 (see FIG. 5G) |
| 91c | A post capillary break conduit for providing fluid communication between the capillary break 87c and the reagent chamber 209c (see FIG. 11B) |
| 92c | Junction of capillary break 87c and post capillary break conduit 91c (see FIG. 11E) |
| 100 | Double-sided sticky gasket of cartridge 10 |
| 100b | Double-sided sticky gasket of cartridge 10b |
| 100c | Double-sided sticky gasket of cartridge 10c |
| 100e | Double-sided sticky gasket of cartridge 10e |
| 100f | Double-sided sticky gasket of cartridge 10f |
| 100g | Double-sided sticky gasket of cartridge 10g |
| 101 | Gasket cut-out 101 positioned to provide fluid connection between the bottom of a sample storage well and a sample storage conduit entrance 81 of cartridge 10 |
| 101b | Gasket cut-out 101b positioned to provide fluid connection between a bottom of a sample storage well and a sample storage conduit entrance of cartridge 10b |
| 101c | Gasket cut-out 101c positioned to provide fluid connection between a bottom of a sample storage well and a sample storage conduit entrance of cartridge 10c |
| 103 | Gasket cut-out 103 positioned to provide fluid connection between an air bladder window and an air bladder cavity |
| 103b | Gasket cut-out 103b positioned to provide fluid connection between air bladder 340b and air bladder duct 343b |
| 105 | Gasket cut-out 105 positioned to provide fluid connection between an air bladder and an air bladder exit port 344 |
| 105b | Gasket cut-out 105 positioned to provide fluid connection between an air bladder duct 343b and an air bladder exit port 344b |
| 107 | Gasket cut-out 107 is an extension of cut out 103, positioned to provide fluid connection between air bladder 340 (see FIG. 3A) and air bladder exit port 344b |
| 109 | Gasket cut-out 109 position to align with pin hole 61 |
| 109b | Gasket cut-out 109b position to align with pin hole 61b |
| 109c | Gasket cut-out 109c position to align with pin hole 61c |
| 115 | Gasket cut-out 115 position to align with capillary break 87 |
| 115b | Gasket cut-out 115b position to align with capillary break 87b |
| 115c | Gasket cut-out 115c position to align with capillary break 87c of cartridge 10c |

TABLE 1-continued

Description of Structural Features.

| Reference Numerals | Description of Structural Features |
|---|---|
| 117 | Gasket cut-out 117 positioned to provide fluid connection between an optical chamber inlet conduit 217 (see FIG. 1G) and an optical chamber overflow conduit 227, and positioned to align with optical windows 213 and 215; in cartridge 10, gasket cut-out 117 defines an optical chamber 211 (see FIG. 1H). |
| 117c | Gasket cut-out 117c positioned to provide fluid connection between an optical chamber inlet conduit 217c and an optical chamber overflow conduit 227c, and positioned to align with optical windows 213c and 215c |
| 117e | Gasket cut-out positioned to align at least partly with at least one of optical windows 213e and 215e |
| 117f | Gasket cut-out positioned to align at least partly with at least one of optical windows 213f and 215f |
| 117g | Gasket cut-out positioned to align at least partly with at least one of optical windows 213g and 215g |
| 119 | Gasket cut-out 119 positioned to provide fluid connection between the optical chamber overflow conduit 227 and a waste receptacle 231 of cartridge 10 (see FIG. 1H) |
| 119b | Gasket cut-out 119b positioned to provide fluid connection between the distal end of the biosensor conduit 337 and a waste receptacle cavity 231b of cartridge 10b |
| 121 | Gasket cut-out 121 positioned to align with a portion of the biosensor conduit groove 335 and the active area 323 of the biosensor array 330 of cartridge 10b |
| 121e | Gasket cut-out positioned to align with active area of the biosensor array 330 of cartridge 10e |
| 121f | Gasket cut-out positioned to align with active area of the biosensor array 330 of cartridge 10f |
| 121g | Gasket cut-out positioned to align with active area of the biosensor array 330 of cartridge 10g |
| 123 | Gasket cut-out 123 positioned to align with a portion of the inlet of the mixing chamber 89 of cartridge 10b (see FIG. 5G) |
| 125 | Gasket cut-out 125 positioned to align with a portion of the outlet of the mixing chamber 89 of cartridge 10b (see FIG. 5G) |
| 127 | Gasket cut-out 127 positioned to align with the reagent chamber 209c of cartridge 10c (see FIG. 11B) |
| 129 | Gasket cut-out 129 positioned to align with the mixing chamber 89c of cartridge 10c (see FIG. 11B) |
| 133 | Gasket cut-out 133 position to align with latch pivot hole 64c of cartridge 10c |
| 207e | Optical chamber entrance in cartridge 10e |
| 207f | Optical chamber entrance in cartridge 10f |
| 207g | Optical chamber entrance in cartridge 10g |
| 209c | A reagent chamber of cartridge 10c (see FIG. 11B) |
| 210c | Conduit for fluidly connecting reagent chamber 209c and mixing chamber 89c (see FIG. 11B) |
| 211 | An optical chamber in cartridge 10 for receiving sample mixed with reagent, and positioned to align with at least a portion of an optical window (see FIG. 1H) |
| 211c | An optical chamber in cartridge 10c for receiving sample mixed with reagent, and positioned to align with at least a portion of an optical window (see FIG. 11C) |
| 211e | An optical chamber in cartridge 10e |
| 211f | An optical chamber in cartridge 10f |
| 211g | An optical chamber in cartridge 10g |
| 212e | Optical chamber exit in cartridge 10e |
| 212f | Optical chamber exit in cartridge 10f |
| 212g | Optical chamber exit in cartridge 10g |
| 213 | A first optical window of cartridge 10 |
| 213c | A first optical window of cartridge 10c |
| 213e | A first optical window of cartridge 10e |
| 213f | A first optical window of cartridge 10f |
| 213g | A first optical window of cartridge 10g |
| 215 | A second optical window of cartridge 10 |
| 215c | A second optical window of cartridge 10c |
| 215e | A second optical window of cartridge 10e |
| 215f | A second optical window of cartridge 10f |
| 215g | A second optical window of cartridge 10g |
| 217 | Detection chamber Inlet conduit joining capillary break 87 to detection (optical) chamber 211 |
| 217b | Detection chamber Inlet conduit joining mixing chamber 89 to detection chamber (biosensor conduit 337) |
| 217c | Detection chamber Inlet conduit joining mixing chamber 89c and detection (optical) chamber 211c of cartridge 10c |
| 219 | Optical chamber inlet conduit groove of optical chamber inlet conduit 217 of cartridge 10 |
| 226c | Overflow conduit groove of overflow conduit of optical chamber 211c of cartridge 10c |
| 227 | Overflow conduit of optical chamber 211 of cartridge 10 |
| 227c | Overflow conduit of optical chamber 211c of cartridge 10c |
| 227e | Overflow conduit of biosensor chamber 337e of cartridge 10e |
| 227f | Overflow conduit of biosensor chamber 337f of cartridge 10f |
| 227g | Overflow conduit of biosensor chamber 337g of cartridge 10g |
| 229 | Overflow conduit groove of optical chamber 211 of cartridge 10 |
| 231 | A waste receptacle cavity of cartridge 10 |
| 231b | A waste receptacle cavity of cartridge 10b |
| 231e | A waste receptacle cavity of cartridge 10e |
| 231f | A waste receptacle cavity of cartridge 10f |
| 231g | A waste receptacle cavity of cartridge 10g |
| 233 | A waste receptacle vent of cartridge 10 |
| 233b | A waste receptacle vent of a cartridge of cartridge 10b |
| 233c | A vent for the optical chamber overflow conduit 227c of cartridge 10c |
| 233e | A waste receptacle vent of a cartridge of cartridge 10e |
| 233f | A waste receptacle vent of a cartridge of cartridge 10f |
| 233g | A waste receptacle vent of a cartridge of cartridge 10g |
| 237c | Crown of cap knob of cap 50c of cartridge 10c |
| 239c | Neck of cap knob of cap 50c of cartridge 10c |
| 241c | Notch in cap 50c for mating with pivot 62c of latch 70c, when cartridge 10c is in a sealed configuration |
| 321 | Biosensor substrate for printing elements of the biosensors and for facilitating thermal contact with an analyzer heating element (see FIG. 5A) |
| 323 | Active area of a biosensor array 330 of cartridge 10b |
| 325 | Biosensor electrical contact of biosensors (see FIG. 5E) |
| 327 | A biosensor receptacle for arranging one or more biosensors in a cartridge in the form of a cut-out ledge in the second housing member 30b, and for exposing the underside of the biosensor(s) to facilitate heating (see FIG. 5A) |
| 330 | A biosensor array of cartridges 10b, 10e, 10f and 10g, comprising one or more biosensors |
| 333 | Proximal end of a biosensor conduit groove of cartridge 10b |
| 335 | Distal end of a biosensor conduit groove of cartridge 10b |
| 336e | Biosensor chamber entrance, defining a location close to the proximal end of the biosensor chamber but outside the biosensor chamber of cartridge 10e |
| 336f | Biosensor chamber entrance, defining a location close to the proximal end of the biosensor chamber but outside the biosensor chamber of cartridge 10f |
| 336g | Biosensor chamber entrance, defining a location close to the proximal end of the biosensor chamber but outside the biosensor chamber of cartridge 10g |
| 337 | A biosensor conduit of cartridge 10b (see FIG. 5G) |
| 337e | A biosensor conduit or chamber of cartridge 10e |
| 337f | A biosensor conduit or chamber of cartridge 10f |
| 337g | A biosensor conduit or chamber of cartridge 10g |
| 338e | Biosensor chamber exit, defining a location close to the distal end of the biosensor chamber but outside the biosensor chamber of cartridge 10e |
| 338f | Biosensor chamber exit, defining a location close to the distal end of the biosensor chamber but outside the biosensor chamber of cartridge 10f |
| 338g | Biosensor chamber exit, defining a location close to the distal end of the biosensor chamber but outside the biosensor chamber of cartridge 10g338e |
| 340 | An air bladder of cartridge 10 |
| 340b | An air bladder of cartridge 10b |
| 340e | An air bladder of cartridge 10e |
| 340f | An air bladder of cartridge 10f |
| 340g | An air bladder of cartridge 10g |
| 341 | An air bladder window of an air bladder 340 |
| 341b | An air bladder window of an air bladder 340b |
| 341c | An air bladder window of an air bladder 340c |
| 341e | An air bladder window of an air bladder 340e |
| 341f | An air bladder window of an air bladder 340f |
| 341g | An air bladder window of an air bladder 340g |

TABLE 1-continued

Description of Structural Features.

| Reference Numerals | Description of Structural Features |
|---|---|
| 342 | A groove in member 30b for defining air bladder duct 343b |
| 343b | An air bladder duct for providing fluid connection between an air bladder 340b and an air bladder exit port 344b |
| 344 | An air bladder exit port of a sample inlet portion 40 of cartridge 10 |
| 344b | An air bladder exit port of a sample inlet portion 40b of cartridge 10b |
| 344c | An air bladder exit port of a sample inlet portion 40c of cartridge 10c |
| 344e | An air bladder exit port of a sample inlet portion 40e of cartridge 10e |
| 344f | An air bladder exit port of a sample inlet portion 40f of cartridge 10f |
| 344g | An air bladder exit port of a sample inlet portion 40g of cartridge 10g |
| 345 | Flexible member of a cartridge for covering air bladder window 341 of cartridge 10 for facilitating operation of the air bladder 340 |
| 345b | Flexible member of a cartridge for covering air bladder window 341b of cartridge 10b for facilitating operation of the air bladder 340b |
| 345c | Flexible member of a cartridge for covering air bladder window 341c of cartridge 10c for facilitating operation of the air bladder 340c |
| 345e | Flexible member of air bladder 340e |
| 345f | Flexible member of air bladder 340f |
| 345g | Flexible member of air bladder 340g |
| 346c | Air bladder duct for providing fluid connection between an air bladder 340c and an air bladder exit port 344c (see FIG. 11E) |
| 346e | Air bladder duct for providing fluid connection between an air bladder 340e and an air bladder exit port 344e |
| 346f | Air bladder duct for providing fluid connection between an air bladder 340f and an air bladder exit port 344f |
| 346g | Air bladder duct for providing fluid connection between an air bladder 340g and an air bladder exit port 344g |
| 347 | Recess for nesting flexible member 345, disposed at the surface of first housing member 20 of cartridge 10 |
| 347b | Recess for nesting flexible member 345b, disposed at the surface of first housing member 20b of cartridge 10b |
| 351c | Bottom cover for covering sample storage conduit 83c of cartridge 10c |

Shown in FIG. 1A is an exploded view of an example of a disposable cartridge 10 for measuring a property of a sample, the cartridge having a rapid sample metering system. From top to bottom, the components are described. Pin 60 is used to hingedly (pivotally) attach cap 50 to the cartridge, via pin hole 61 shown in the first housing member 20; the bottom of the pin hole 61 is shown as 63 in the second housing member 30. Flexible member 345 nests in a recess 347 in the first housing member 20 and is used to seal off the air bladder window 341. An optional cap, sealing ring, or washer 57, may be attached to the underside of the cap 50. In some embodiments, the sealing ring/washer is referred to as a gasket, which may be made from several different material known to a person skilled in the art. PTFE (Polytetrafluoroethylene, also known as Teflon®) is a good example of gasket material. An advantage of PTFE in this application is that it has a very low surface energy (also described as a hydrophobic material) and can pass easily over sliding surface 49 of inlet portion 40, without dragging the blood sample as the seal 57 moves along the surface of inlet portion 40.

Also shown in the first housing member 20 is the first optical window 213, an air bladder exit port 344, the top portion 43 of a sample storage well 41 (see FIG. 1G), a cap latch 70, and the sample inlet portion 40. Sample inlet portion 40 comprises sample storage well 43, air bladder exit port 344, pin hole 61, and sliding surface 49 that surrounds the top portion of the sample storage well 43 and the air bladder exit port 344. Elements 40, 344, 43, 70 of cartridge 10 interact with the cap 50 as described in more detail below. Some embodiments of the cartridge described herein provide a good seal between the cap 50 and the sample inlet portion 40, without a cap latch 70, depending on the robustness of the hinged attachment of the cap. For example the fourth embodiment (cartridge 10d; see FIGS. 12A-12D) is an example of a cartridge without a cap latch. An advantage to having a robust hinged, or pivotal, attachment and no cap latch is the greater space provided at the sample storage well 41, for accommodating the heel of a baby or a large adult finger. The provision of space at the sample storage well 41 is further described below, with reference to the fifth, sixth and seventh embodiments of the invention.

Still referring to FIG. 1A, there is shown a double-sided sticky gasket 100, comprising several gasket cut-outs, including:
cut-out 101, positioned to provide fluid connection between the bottom of a sample storage well and a sample storage conduit entrance 81 of cartridge 10;
cut-out 109 position to align with pin hole 61;
cut-outs 105, 107 and 103 are positioned to provide fluid connection between an air bladder cavity 340 (FIG. 3A) and air bladder exit port 344;
cut-out 115 position to align with capillary break 87;
cut-out 117 positioned to provide fluid connection between an optical chamber inlet conduit 217 (see FIG. 1G) and an optical chamber overflow conduit 227 (FIG. 1H), and positioned to align with optical windows 213 and 215 (FIG. 1H); in cartridge 10;
cut-out 117 defines an optical chamber 211 (see FIG. 1H);
cut-out 119 positioned to provide fluid connection between the optical chamber overflow conduit 227 (FIG. 1H) and a waste receptacle 231 of cartridge 10.

Below gasket 100 is the second housing member 30, showing the following elements: a sample storage conduit entrance 81; a sample storage conduit groove 85 that defines the sample storage conduit 83 (FIG. 1G); the second portion 87″ of capillary break 87 (see FIG. 1F); and a waste receptacle cavity 231.

The assembled cartridge body, comprising the first housing member 20, the sticky gasket 100, and the second housing member 30 may be made of a clear polymeric material, a clear plastic, a material that is transparent to a wavelength of electromagnetic radiation used to interrogate the sample, or a combination thereof.

Shown in FIG. 1B (view in conjunction with FIG. 2A) is a bottom view of the first housing member 20 of the cartridge shown in FIG. 1A showing the optical inlet conduit groove 219 that defines the optical chamber inlet conduit 217 when housing member 20 is attached to sticky gasket 100. Optical chamber inlet conduit 217 joins in fluid communication, the capillary break 87 with the first optical window 213. Overflow conduit groove 229 defines the overflow conduit 227 (when housing member 20 is attached to sticky gasket 100) that joins the first optical window 213 with the waste receptacle cavity 231 in the assemble cartridge. Also shown in FIG. 1B is a portion of the cartridge defining a bottom opening 45 of sample storage well 41, pin hole 61 and air bladder exit port 344. Shown in FIG. 10 is the bottom view of the first housing member 20 shown in FIG. 1B, overlaid by, and in alignment with, gasket 100 shown in FIG. 1A. Shown in FIG. 1D is a top view of the second housing member 30 of the cartridge shown in FIG. 1A. Shown in FIG. 1E is a top view of the second housing member 30 shown in FIG. 1D, overlaid by, and in alignment with, the gasket 100 shown in FIG. 1A.

Shown in FIG. 1F is a top view of the cartridge 10 shown in FIG. 1A, with the cap 50 in a fully closed position. Illustrated in FIG. 1G is an enlarged cross-sectional view through the cartridge shown in FIG. 1F along line G-G, showing the sample storage well 41, the sample storage conduit entrance 81, the sample storage conduit 83, the sections 87' and 87" of the capillary break 87 (see hidden view in FIG. 1F), and Inlet conduit 217 of optical chamber 211 (see FIG. 1H). Cap handle 59 is also indicated. Shown in FIG. 1H is a second enlarged cross-sectional view through the cartridge shown in FIG. 1F along line H-H, showing, an optical chamber 211 (defined by cut-out 117 of the double-sided sticky gasket 100), a first optical window 213, a second optical window 215, an optical chamber overflow conduit 227, a waste receptacle 231 and its vent 233. The optical chamber 211 is a non-limiting example of a detection chamber. Shown in FIG. 1J is a third cross-sectional view through the cartridge shown in FIG. 1F along line J-J, showing the sample storage conduit entrance 81, mating with the bottom opening 45 of the sample storage well 41. This mating aspect is better illustrated in FIG. 5H, regarding cartridge 10b. In some embodiments, the bottom opening 45 and the sample storage conduit entrance 81 coincide and are not shown as two separate structures.

The fifth, sixth and seventh embodiments of the disposable cartridge provide additional space at the cartridge inlet, in order to accommodate larger fingers and a baby's heel, when these body parts are used to provide the blood sample. Furthermore, the fifth, sixth and seventh embodiments described herein, permit the option to choose from a larger selection of materials, for example plastics, for manufacturing the cartridges.

Embodiments one to four require blood storage conduits that possess sufficient wetting ability (or wettability; or hydrophilicity) to draw the blood sample by capillary action, up to an enlarged section referred to as a capillary break, which stops blood flow by capillary action (i.e. the capillary action created in the enlarged section is not sufficient to draw the blood into the section). Wettability studies usually involve the measurement of contact angles, which indicates the degree of wetting when a solid and liquid interact.

For example, Table 2 lists contact angles, the angles between the plastic surface and the surface of a water drop on the plastic surface. The smaller the contact angle, the more wettable is the plastic. By way of illustration, a common example of a non-wettable or hydrophobic surface is Teflon (also known as Polytetrafluoroethylene [PTFE]), which has a contact angle of 109.2 (see Table 2). It is well known that water "beads" on a Teflon surface, accounting for the large contact angle; it is also well known that water "spreads" over a clean glass surface accounting for a small contact angle.

Table 2 provides a selection of plastics for manufacturing the cartridges, with compromises between wetting ability and optical clarity, which must be considered regarding cartridge functionality and cartridge manufacture. Other types of polymers can be blended to enhance or decrease the wettability of the blended polymer. A commonly used blended polymer is PETG, which is used to make plastic capillary tubes for collecting capillary blood. PETG has mostly replaced glass as an alternative to glass for safety concerns, for making capillary tubes used to collect capillary blood from babies. The manufacturer does not provide details of the PETG composition. PETG is a blend of PET (polyethylene terephthalate) and PEG (polyethylene glycol).

PET has a contact angle of 72.5, and base on the inventor's experience, PET does not provide sufficient capillary action to draw blood into a disposable cartridge. While the contact angle of commercial PETG is not available, it is possible that other additives e.g., polystyrene, may be added to provide the required wettability (Kolahchi, A. R., AIP Conference Proceedings 1664, 030001, 2015). Other treatments, for example, plasma surface treatment and alteration of surface roughness can also be used to modify surface wettability.

TABLE 2

| Polymer Names and Acronyms Commonly Used | Contact Angle |
| --- | --- |
| Polyvinyl alcohol (PVOH) | 51 |
| Polyvinyl acetate (PVA) | 60.6 |
| Nylon 6 (polycaprolactum, aramid 6) | 62.6 |
| Polyethylene oxide (PEO, PEG, polyethylene glycol) | 63 |
| Nylon 6,6 | 68.3 |
| Nylon 7,7 | 70 |
| Polysulfone (PSU) | 70.5 |
| Polymethyl methacrylate (PMMA, acrylic, plexiglas) | 70.9 |
| Nylon 12 | 72.4 |
| Polyethylene terephthalate (PET) | 72.5 |
| Epoxies | 76.3 |
| Polyoxymethylene (POM, polyacetal, polymethylene oxide) | 76.8 |
| Polyvinylidene chloride (PVDC, Saran) | 80 |
| Polyphenylene sulfide (PPS) | 80.3 |
| Acrylonitrile butadiene styrene (ABS) | 80.9 |
| Nylon 11 | 82 |
| Polycarbonate (PC) | 82 |
| Polyvinyl fluoride (PVF) | 84.5 |
| Polyvinyl chloride (PVC) | 85.6 |
| Nylon 8,8 | 86 |
| Nylon 9,9 | 86 |
| Polystyrene (PS) | 87.4 |
| Polyvinylidene fluoride (PVDF) | 89 |
| Poly n-butyl methacrylate (PnBMA) | 91 |
| Polytrifluoroethylene | 92 |
| Nylon 10,10 | 94 |
| Polybutadiene | 96 |
| Polyethylene (PE) | 96 |
| Polychlorotrifluoroethylene (PCTFE) | 99.3 |
| Polypropylene (PP) | 102.1 |
| Polydimethylsiloxane (PDMS) | 107.2 |
| Poly t-butyl methacrylate (PtBMA) | 108.1 |
| Fluorinated ethylene propylene (FEP) | 108.5 |
| Hexatriacontane | 108.5 |
| Paraffin | 108.9 |
| Polytetrafluoroethylene (PTFE) | 109.2 |
| Poly(hexafluoropropylene) | 112 |
| Polyisobutylene (PIB, butyl rubber) | 112.1 |

(obtained from DIVERSIFIED Enterprises, 101 Mulberry St., Suite 2, Claremont, NH 03743 U.S.A.)

The disposable cartridge described herein may comprise an optical chamber, which is preferably made of transparent plastic. Some very transparent plastics, for example Polymethyl methacrylate (PMMA, plexiglass) and PET, can be injection molded, but may not be sufficiently wettable for the purpose of drawing blood by capillary action. In the fifth to seventh embodiments of the cartridge, the cartridge can function without relying on capillary action to draw the blood into the optical chambers of the cartridges. When capillary action is not relied upon, the positive air pressure from an air bladder is used to push the blood into the optical chamber, in a regulated manner. Other similar embodiments use a combination of capillary action and positive air pressure from an air bladder, to respectively draw the blood into the optical chamber and push the blood out of the optical chamber, in a regulated manner. The different features described herein, for example the use of an air bladder, therefore provides more options for manufacturing the cartridges.

Figure 2B:
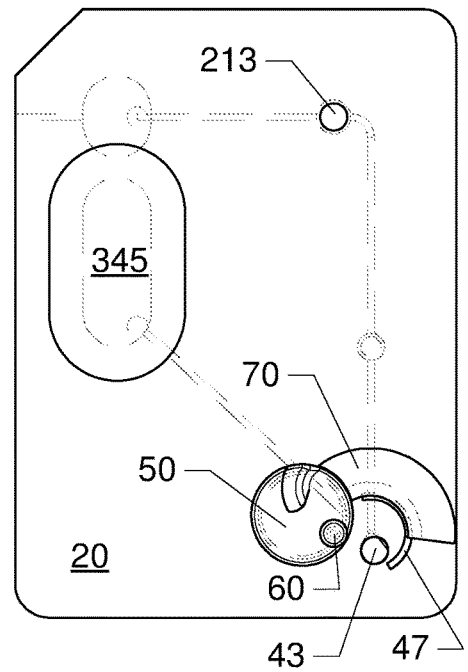
FIG. 2B is a top view of the cartridge 10 shown collectively in FIGS. 1A-1J, with the cap 50 in a fully open position.

Shown in FIG. 2A is a top view of the cartridge 10 shown collectively in FIGS. 1A-1J, with the cap 50 and pin 60 removed to indicate the arrangement of components 61 (pin hole for receiving pin 60), 344 (air bladder exit port of sample inlet portion 40), 43 (top opening of sample storage well 41) and 47 (which may be considered as an element of the sample overflow well of sample inlet portion 40; cartridge 10c, for example, does not include sample overflow well 47). Shown in FIG. 2B is a top view of the cartridge 10 shown collectively in FIGS. 1A-1J, with the cap 50 in a position for an unsealed configuration of the cartridge. In the unsealed configuration the cap 70 may rest against cap latch 70 as shown in FIG. 2A, and the cap latch may act as a cap stop to define the unsealed configuration.

Figure 2C:
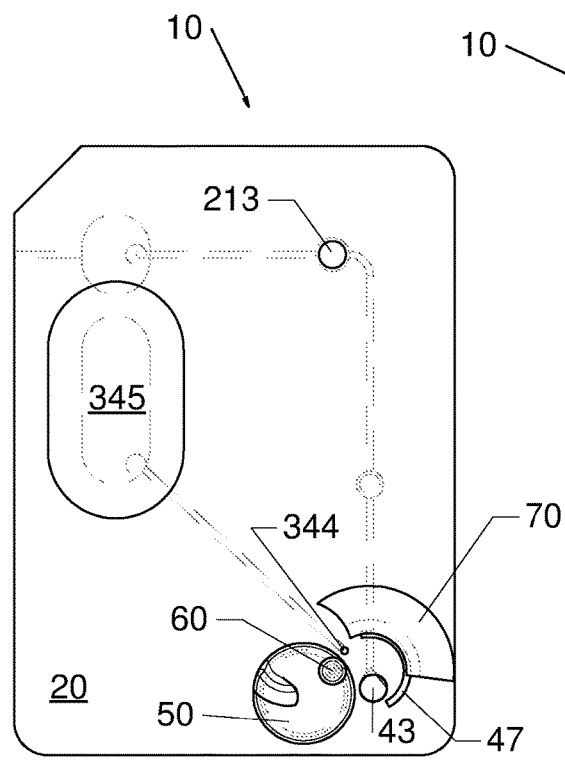
FIG. 2C is a top view of the cartridge 10 shown collectively in FIGS. 1A-1J, with the cap 50 in a partly open position.
Figure 2D:
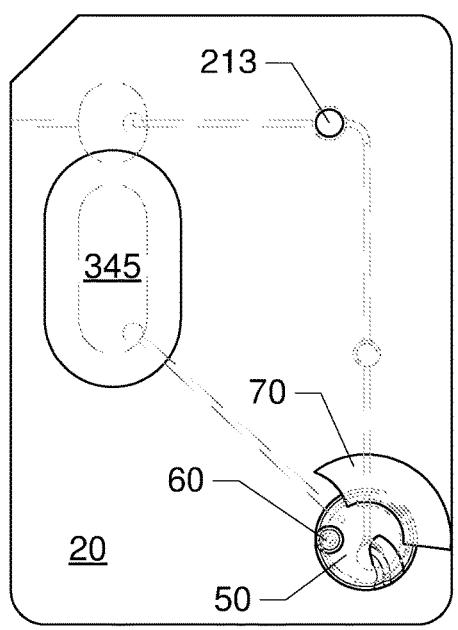
FIG. 2D is a top view of the cartridge 10 shown collectively in FIGS. 1A-1J, with the cap 50 in a fully closed position

Shown in FIG. 2C is a top view of the cartridge 10 shown collectively in FIGS. 1A-1J, with the cap 50 in a position for a partly open configuration of the cartridge. Shown in FIG. 2D is a top view of the cartridge 10 shown collectively in FIGS. 1A-1J, with the cap 50 in a position for a sealed configuration of the cartridge. FIGS. 2B-2D illustrate how, by moving the position of cap 50, the cartridge is adjustable between an unsealed and a sealed configuration. In the sealed configuration shown in FIG. 2D, the cap 50 is engaged with cap latch 70, and the cap latch is acting as a cap stop to define the sealed configuration.

Referring to FIGS. 3A-3D are perspective views of the cartridge 10 shown in FIGS. 2A & 2D, providing more details of the sample inlet portion 40 and its association with the cap 50. Shown in FIG. 3A is a top perspective view of the cartridge 10 shown in FIG. 2A, with air bladder 340 open. Shown in FIG. 3B is a detailed view of detail B of the cartridge shown in FIG. 3A, and indicates the arrangement of components 344, 61, 43, 47, and the cap latch recess 73 of cap latch 70. Shown in FIG. 3C is a top perspective view of the cartridge 10 with cap 50 positioned over sample inlet portion 40 so that the cartridge is in a sealed configuration. Shown in FIG. 3D is a detailed view of detail D of the cartridge shown in FIG. 3C. An outer periphery of cap 50 is shown to be engaged with cap latch recess 73 of cap latch 70. In this example, the cap latch recess 73 is operating as a latch to retain cap 50 in a closed position where the cartridge is in a sealed configuration. Also shown in FIG. 3D is cap handle 59, that is used to move cap 50 pivotally about pin 60

Figure 4A:
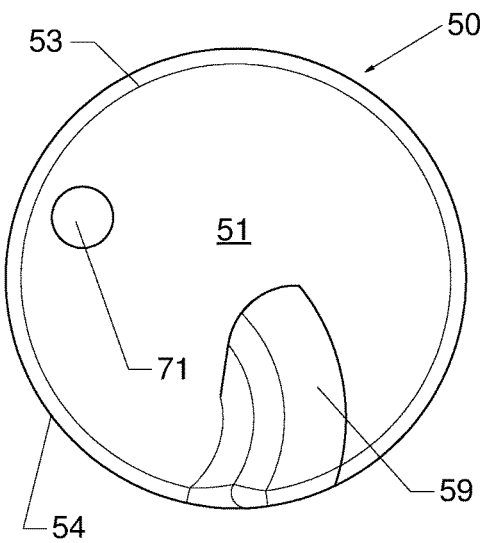
FIG. 4A is a top view of the cap 50 shown in FIGS. 2B-2D.
Figure 4B:
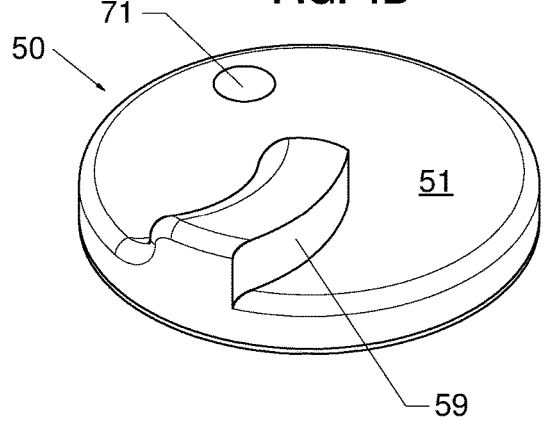
FIG. 4B is a perspective top view of the cap 50 shown in FIG. 4A.
Figure 4C:
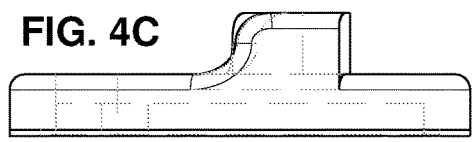
FIG. 4C is a front view of the cap 50 shown in FIG. 4A.
Figure 4D:
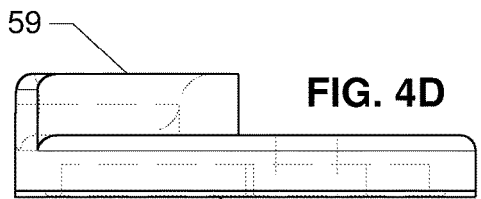
FIG. 4D is a right side view of the cap 50 shown in FIG. 4A.
Figure 4E:
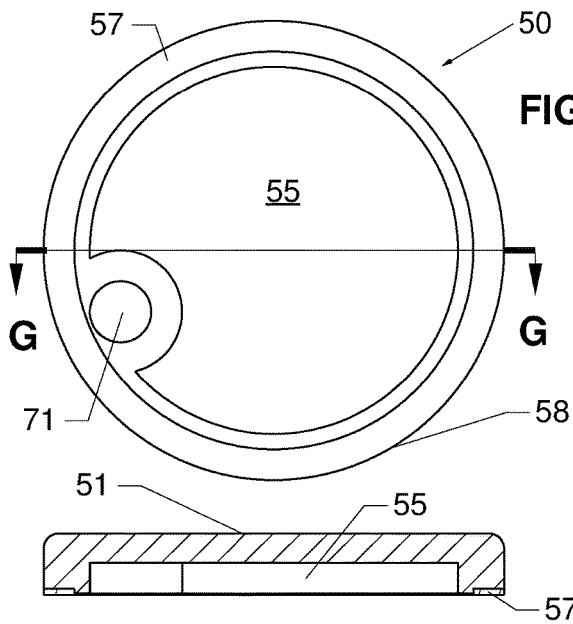
FIG. 4E is a bottom view of the cap 50 shown in FIG. 4A.
Figure 4F:
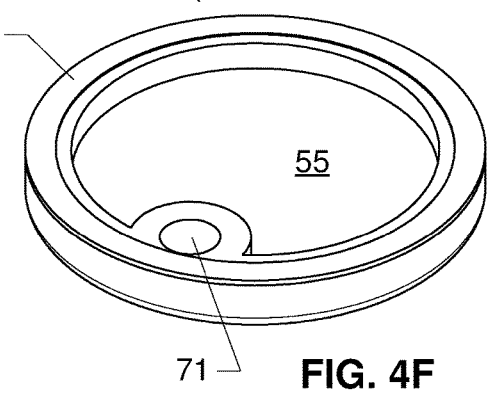
FIG. 4F is a perspective bottom view of the cap 50 shown in FIG. 4E.
Figure 4G:
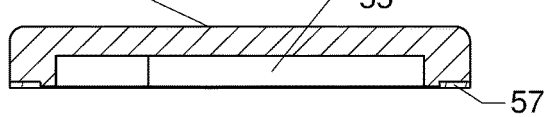
FIG. 4G is a cross-sectional view through the cap 50 shown in FIG. 4E along line G-G.

The details of the cap 50 are illustrated in FIGS. 4A-4G. Shown in FIG. 4A is a top view of the cap 50 shown in FIG. 3D, showing pin hole 71 in cap 50 for receiving pin 60, and the top side 51 of the cap 50, and a cap handle 59 for facilitating rotation of cap 50. Also shown are a sweeping portion 53 of cap 50 and trailing portion 54 of cap 50, in the context of a counterclockwise rotation of the cap 50 about the pin 60, when the cartridge is adjusted from an unsealed configuration (see FIG. 2B) to a sealed configuration (see FIG. 2D). Shown in FIG. 4B is a top perspective view of the cap 50 shown in FIG. 4A. Shown in FIG. 4C is a front view of the cap 50 shown in FIG. 4A. Shown in FIG. 4D is a right side view of the cap 50 shown in FIG. 4A, indicating the underside 52 of cap 50. Shown in FIG. 4E is a bottom view of the cap 50 shown in FIG. 4A, showing a sweeping cap edge 58 disposed at the sweeping portion 53 of cap 50 for skimming off excess sample, and the cap recess 55. A flat surface surrounds the cap recess 55, the flat surface may comprise, for example, a sealing ring 57. In this example, the sweeping cap edge 58 is the edge of the cap sealing ring 57. Shown in FIG. 4F is a bottom perspective view of the cap 50 shown in FIG. 4E. Shown in FIG. 4G is a cross-sectional view through the cap 50 shown in FIG. 4E along line G-G, showing the top side 51 of cap 50, the cap recess 55, and the cap sealing ring 57.

Shown in FIG. 5A is an exploded view of the disposable cartridge 10b for measuring a property of a sample, the cartridge having a rapid sample metering system, according to a second embodiment of the cartridge. This embodiment is similar to the first embodiment of the cartridge 10, and illustrated collectively in FIG. 1A to FIG. 4G, and accordingly, elements common to them share common reference numerals. For some elements, the letter "b" is appended to the end of the reference numerals, in order to indicate that the elements are part of the second embodiment of the cartridge. A first difference between the first (10; FIGS. 1A to 4G) and second (10b) embodiments of the cartridge is that the shape of the cap 50 is circular and the shape of cap 50b is elliptical. It should be understood that these are examples of preferred embodiments, and the shape is not limited to being circular or elliptical. Cartridge 10g (FIGS. 18 and 19) provides a different, irregular, cap shape. Another non-limiting example is an oval shape that is not elliptical. An advantage of an ellipse, having a major radius and a minor radius, is that it is equivalent to a circle having a radius equal to the major radius of the ellipse, in the context of space between the latch 70b and the pin hole 61b (see FIGS. 5A and 6A), whereby the pin hole 61b is located at one end of the major axis of the ellipse. The larger space, illustrated in FIG. 6B (compare with illustration in FIG. 2B), is useful for accommodating larger fingers, if blood is obtained from a finger prick. Cartridges 10e, 10f and 10g (FIGS. 14 to 19) provide even more space. A second difference, between the first (10; FIGS. 1A to 4G) and second (10b) embodiments of the cartridge, is that the pin 60b is an integral part of the cap 50b, as illustrated collectively in FIGS. 8A-8G. A third difference is that cartridge 10b comprises a mixing chamber 89, for mixing sample and one or more reagent. A fourth difference is that the detection system in the first embodiment of the cartridge is optical or spectrophotometric, whereas the detection system in the second embodiment is electrochemical or biosensors. A person of ordinary skill will appreciate that other embodiments of the cartridge can have either, both of the aforementioned detection systems, or some other detection system. The fifth, sixth and seventh embodiments of cartridges are examples of cartridges having two different detection systems. Other minor differences between the various disposable cartridges described herein will become obvious by following the reference numerals and the corresponding description of structural features provided in Table 1.

Shown in FIG. 5B is a bottom view of the first housing member 20b of the cartridge shown in FIG. 5A. Shown in FIG. 5C is the bottom view of the first housing member 20b shown in FIG. 5B, overlaid by and in alignment with the gasket 100b shown in FIG. 5A. Shown in FIG. 5D is a top view of the second housing member 30b of the cartridge shown in FIG. 5A. Shown in FIG. 5E is the top view of the second housing member 30b shown in FIG. 5D, overlaid by and in alignment with the gasket 100b shown in FIG. 5A.

Figure 5F:
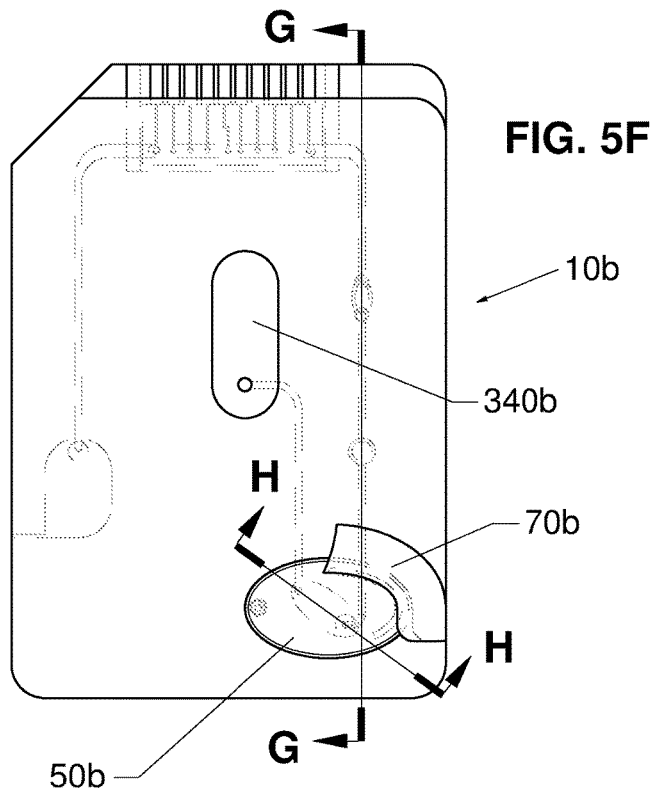
FIG. 5F is a top view of the cartridge 10b shown in FIG. 5A, with the cap 50b in a fully closed position, and air bladder 340b open.
Figure 5H:
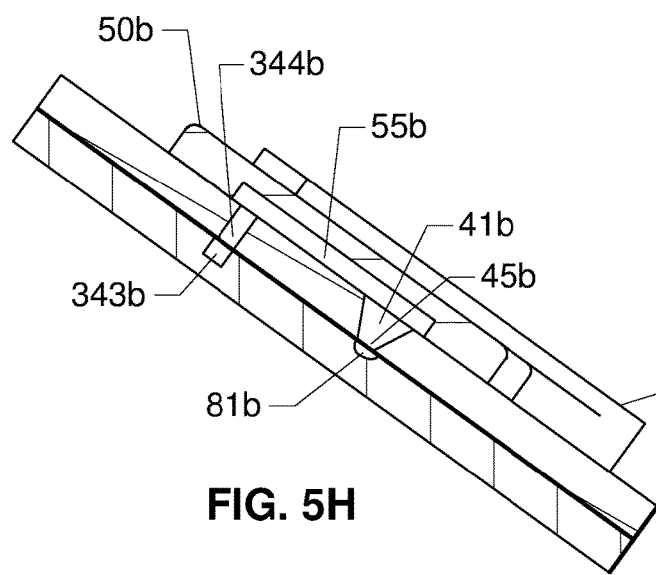
FIG. 5H is an enlarged second cross-sectional view through the cartridge 10b shown in FIG. 5F along line H-H.
Figure 5G:
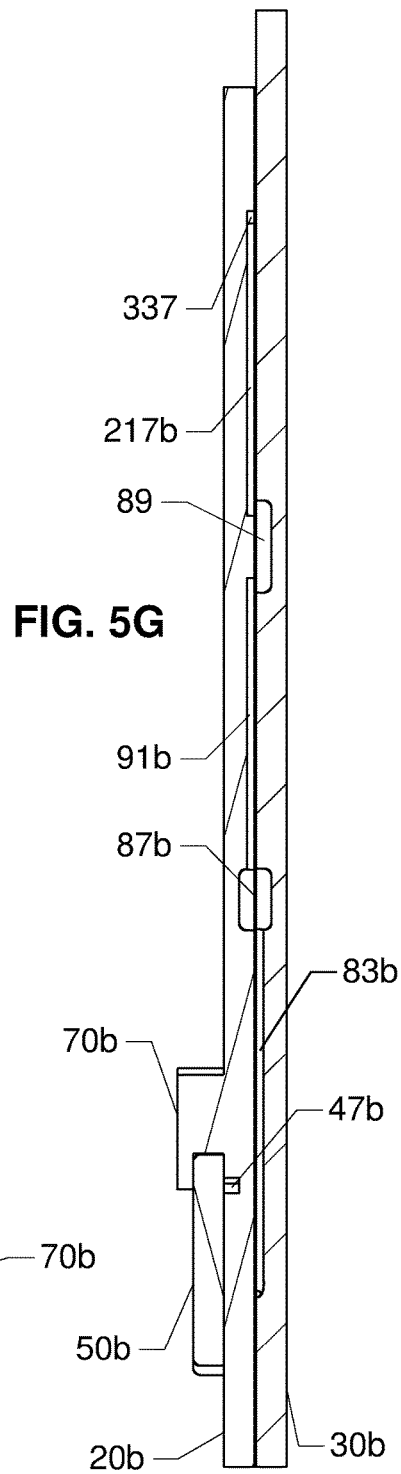
FIG. 5G is an enlarged first cross-sectional view through the cartridge 10b shown in FIG. 5F along line G-G.

Shown in FIG. 5F is a top view of the cartridge 10b shown in FIG. 5A, with the cartridge in a sealed configuration, and with the air bladder laminate hidden, in order to view the air bladder 340b. Shown in FIG. 5G is an enlarged first cross-sectional view through the cartridge 10b shown in FIG. 5F along line G-G. Shown in FIG. 5H is an enlarged second cross-sectional view through the cartridge 10b shown in FIG. 5F along line H-H, illustrating the fluid connection between the air bladder duct 343b and the sample well 41b, via the air bladder exit port 344b, and the cap recess 55b. The arrangement of the bottom 45b of the sample storage well 41b with the sample storage conduit entrance 81b, is also illustrated.

Figure 6A:
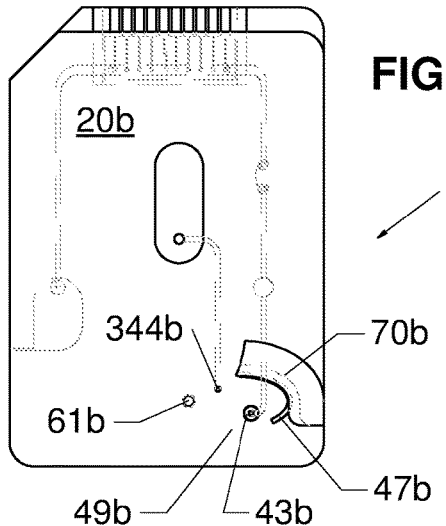
FIG. 6A is a top view of the cartridge 10b shown collectively in FIGS. 5A-5H, with the cap 50b removed
Figure 6B:
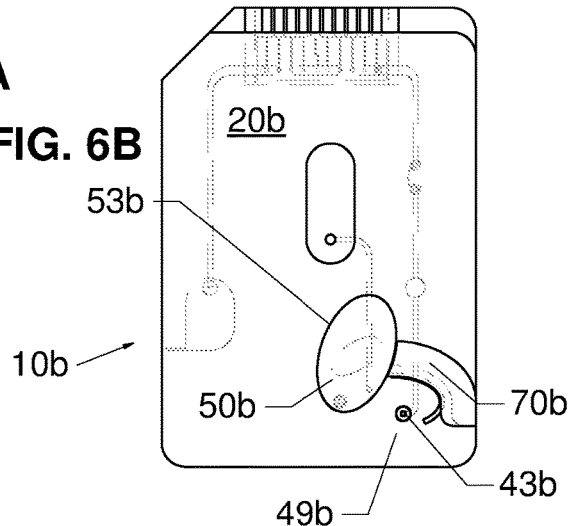
FIG. 6B is a top view of the cartridge 10b shown collectively in FIGS. 5A-5H, with the cap 50b in a fully open position.
Figure 6C:
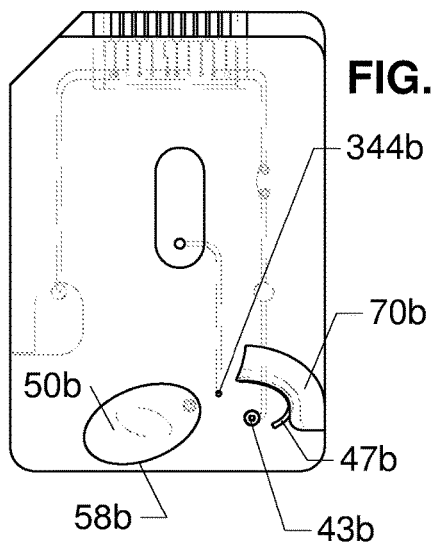
FIG. 6C is a top view of the cartridge 10b shown collectively in FIGS. 5A-5H, with the cap 50b in a partly open position.
Figure 6D:
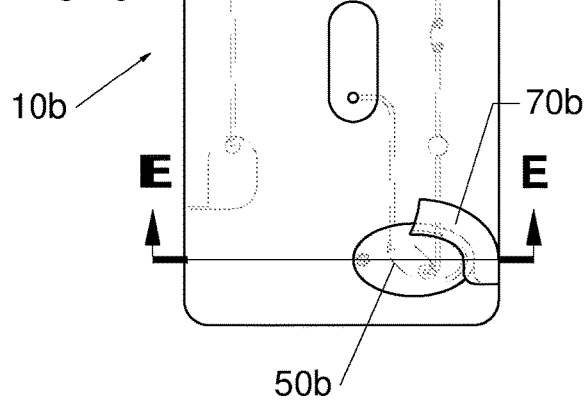
FIG. 6D is a top view of the cartridge 10b shown collectively in FIGS. 5A-5H, with the cap 50b in a fully closed position.
Figure 6F:
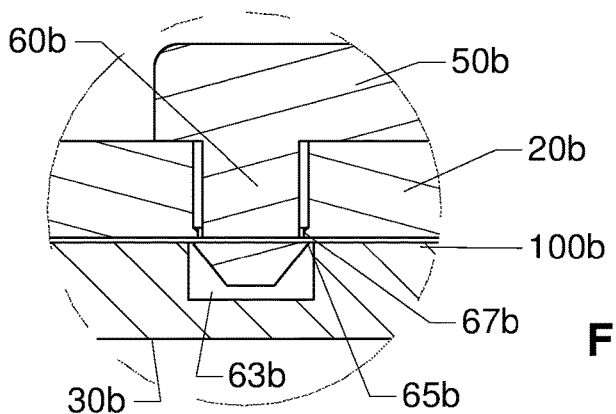
FIG. 6F is a detailed view of detail F of cartridge 10b shown in FIG. 6E, showing a snap-fit mechanism for attaching the pin 60b of cap 50b in the cartridge.
Figure 6E:
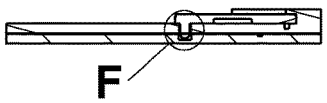
FIG. 6E is a cross-sectional view of cartridge 10b shown in FIG. 6D along line E-E.

Shown in FIG. 6A is a top view of the cartridge 10b shown collectively in FIGS. 5A-5H, with the cap 50b hidden. Shown in FIG. 6B is a top view of the cartridge 10b shown collectively in FIGS. 5A-5H, with the cartridge in an unsealed configuration. Shown in FIG. 6C is a top view of the cartridge 10b shown in FIG. 6B, with the cap 50b in a partially open position. Shown in FIG. 6D is a top view of the cartridge 10b shown collectively in FIGS. 6B-6C, with the cartridge in a sealed configuration. Shown in FIG. 6E is a cross-sectional view of cartridge 10b shown in FIG. 6D along line E-E. Shown in FIG. 6F is a detailed view of detail F of cartridge 10b shown in FIG. 6E, showing a snap-fit mechanism for engaging the cap 50b in the cartridge 10b shown collectively in FIGS. 6B-6D. Description of the structural features is provided in Table 1.

Shown in FIG. 7A is a perspective view of the cartridge 10b shown in FIG. 6A. Shown in FIG. 7B is a detailed view of detail B of the cartridge shown in FIG. 7A, showing details of the sample inlet portion 40b. Shown in FIG. 7C is a perspective view of the cartridge 10b shown in FIG. 6D. Shown in FIG. 7D is a detailed view of detail D of the cartridge shown in FIG. 7C. Description of the structural features is provided in Table 1.

Shown in FIG. 8A is a top view of the cap 50b shown in FIGS. 7C-7D, showing a sweeping portion 53b of cap 50b and trailing portion 54b of cap 50b, in the context of counterclockwise rotation of the cap 50b about the pin 60b, when the cartridge is adjusted from an unsealed configuration (see FIG. 6B) to a sealed configuration (see FIG. 6D). Shown in FIG. 8B is a perspective view of the cap 50b shown in FIG. 8A. Shown in FIG. 8C is a front view of the cap 50b shown in FIG. 8A, showing the top side 51b, the underside 52b, the pin 60b and a snap fit lip 65b for locking pin 60b in pinhole 61b. Shown in FIG. 8D is a right side view of the cap 50b shown in FIG. 8A. Also shown in FIG. 8E is a bottom view of the cap 50b shown in FIG. 8A, showing a sweeping cap edge 58b disposed at the sweeping portion 53b of cap 50 for skimming off excess sample, and the cap recess 55b. In this embodiment of cap 50b, there is no gasket and the cap is made of suitable material that can provide a sealed configuration of the cartridge, making gaskets optional. In some embodiments, for example cartridge 10e, the gasket 57e is installed in the first housing member 20e of the cartridge 10e. Shown in FIG. 8F is a perspective view of the cap 50b shown in FIG. 8E. Shown in FIG. 8G is a cross-sectional view through the cap 50b shown in FIG. 8E along line G-G, showing the cap recess 55b and the pin snap fit lip 65b. The means provided for hingedly attaching the cap are examples only, and other means for hingedly attaching the cap to the body of the cartridge are considered to be within the scope of the invention. The first, second, third, fourth and seventh embodiments are examples of cartridges having a cap hingedly attached to the cartridge body, whereby the cap swings in a horizontal plane (i.e., the plane defined by the flat surface surrounding the sample storage well and the air bladder exit port); the fifth and sixth embodiments are examples of cartridges having a cap hingedly attached to the cartridge body, whereby the cap swings in a vertical plane (i.e., the plane orthogonal to the plane defined by the flat surface surrounding the sample storage well and the air bladder exit port).

Overview of Cartridge (Cartridge 10b Described as a Non-Limiting Example)

Measurement of any property of a liquid sample, for example glucose concentration or prothrombin time, can be considered as non-limiting examples for illustrating the use of the cartridge. In this illustration, cartridge 10b will be used as a non-limiting example (see FIGS. 5A to 8G). In general terms, the present disclosure provides a disposable cartridge for metering a sample for measuring a property of the sample, the cartridge comprising:

1) a housing comprising a first housing member 20b and a second housing member 30b, bonded together by a double-sided sticky gasket 100b;

2) a cap 50b having a top side 51b, an underside 52b, a sweeping cap edge 58b for skimming off excess sample, and a cap recess 55b in the underside of the cap for creating a closed air passage illustrated in FIG. 5H;

3) a pin 60b for hingedly, or pivotally, attaching the cap 50b to an inlet portion 40b of the cartridge via pin hole 61b. The sample inlet portion 40b, comprises elements of the cartridge that interact with the cap 50b and may comprise:

a) a top opening 43b of a sample storage well 41b for receiving the sample;

b) the sample storage well 41b for storing a portion of the sample;

c) a sliding surface 49b (see FIG. 6A) for frictionally engaging the cap 50b;

d) a hole 61b for receiving the pin 60b for hingedly attaching the cap 50b to the sample inlet portion 40b;

e) a sample overflow well 47b for receiving the excess sample during the period of closing the cap 50b; In some examples of the cartridge, for example, cartridges 10c and 10d, the sample overflow well 47b is optional. For example, with respect to cartridge 10c, the sweeping portion 53c of the cap 50c (see FIG. 10A) comprises a groove 48c (see FIG. 10F) disposed in the underside of the cap in front of the sweeping edge 58c, for holding any excess sample;

f) a cap latch 70b, for facilitating a sealed configuration of the cartridge when an outer periphery of cap 50b is engaged with cap latch recess 73b, and g) an air bladder exit port 344b in fluid communication with an air bladder 340b.

4) the air bladder 340b for providing pressurized air to the air bladder exit port 344b;

5) a capillary break 87b (see FIG. 5G) for stopping sample flow, the flow being facilitated by capillary action;

6) a post capillary break conduit 91b (see FIG. 5G) providing fluid communication between the capillary break 87b and a mixing chamber 89;

7) a detection chamber (a conduit 337 over the active area 323; see FIGS. 5A and 5E) of one or more biosensor of a biosensor array 330; in the case of cartridge 10, the detection chamber is the optical chamber 211 (see FIG. 1H) for generating a signal used to determine or calculate a property of the sample;

8) a waste receptacle cavity 231b for receiving fluid flowing beyond the detection chamber via distal end of biosensor conduit groove 335; and 9) a vent 233b for relieving pressure in the waste receptacle cavity 231b (see FIGS. 5A & 5D).

Another non-limiting example of a sample inlet portion is provided with reference to FIGS. 16A to 17H. In this example, the sample inlet portion (e.g. 40f of cartridge 10f), may comprise elements of the cartridge that interact with cap 50f. It will be appreciated that a sample inlet portion (e.g. 40f) does not define a particular element of a cartridge, and the cartridge embodiments described with reference to FIGS. 16A to 17H do not contain all the elements previously mentioned for the cartridge depicted above with reference to FIGS. 5A to 8G. For the sake of clarity, some drawings (e.g. FIG. 17H) illustrate the inlet portion 40f comprising elements 43f (top opening of a sample storage well 41f of cartridge 10f), 49f (a flat surface of inlet portion 40f surrounding the sample storage well and the air bladder exit port of cartridge 10f), and 344f (an air bladder exit port of a sample inlet portion 40f of cartridge 10f).

The cartridge may be pre-loaded with one or more dry reagents deposited at one or more points before the detection chamber 323 (FIG. 5E; or before the optical window defined by 213/211/215; FIG. 1H; or 213c/211c/215c, FIG. 11C). Cartridge 10b comprises an optional mixing chamber 89, and a post capillary break conduit 91b, which defines the conduit between the capillary break 87b and the mixing chamber 89, illustrated in FIG. 5G. In some cartridge embodiments, the one or more reagent is deposited in the mixing chamber 89. Dry thromboplastin is an example of a reagent, which is used for measuring prothrombin time (PT) usually reported as PT-INR (PT-International Normalized Ratio), and dry celite or kaolin are examples of a reagent used for measuring activated clotting time (ACT).

The cartridge is adjustable between an unsealed configuration and a sealed configuration. In the unsealed configuration illustrated in FIG. 6B, the top opening 43b of sample storage well 41b is configured to receive the sample; and the air bladder exit port 344b (view in conjunction with FIG. 6A) is optionally covered by the cap 50b. In the sealed configuration illustrated in FIGS. 5F and 5H, the cap recess 55b facilitates provision of a closed air passage connecting the air bladder exit port 344b and the sample storage well 41b for transferring pressurized air from the air bladder exit port 344b to the sample storage well 41b. As the cartridge is adjusted from the unsealed configuration to the sealed configuration (an intermediate configuration is illustrated in FIG. 6C), the sweeping cap edge 58b skims off excess sample above the top opening 43b (see FIG. 6C in conjunction with FIG. 5H) of the sample storage well 41b. The volume of sample in the cartridge in the sealed configuration is equivalent to the volume measured from the top opening 43b of the sample storage well 41b to the capillary break 87b (FIG. 5G). The sample storage well 41b also comprises a bottom opening 45b of the sample storage well 41b. In this example, the top 43b is substantially larger than the bottom 45b, as illustrated in FIG. 5H. Having a larger top opening 43b may assist in transferring a drop of blood from a body part, for example a finger; to the sample storage well 41b. In the case of a small infant, a heel is a preferred body part. The size of the smaller bottom opening 45b is preferably similar to the size of the sample storage conduit entrance 81b, for facilitating blood flow by capillary action. In some embodiments, bottom opening 45b and the sample storage conduit entrance 81b coincide, for example as shown in FIG. 5H (for cartridge 10b), and for example FIGS. 17G and 17H (for cartridge 10f; only bottom opening 45f is shown.

Once the cartridge is in the sealed configuration; the cartridge is ready to be inserted into a slot or receptor of an analyzer. The analyzer detection system comprises one or more of, optical; spectrophotometric, fluorescence; chemiluminescence, electrochemical, biosensor, amperometric, potentiometric or conductimetric technology. However, these are just examples and other detection systems are considered to be within the scope of the present invention. These detection systems are known to a person skilled in the art and for the sake of brevity; will not be discussed here.

In the case of spectrophotometric or optical measurement, an embodiment of an analyzer comprises a source of electromagnetic radiation (EMR) and one or more photodetectors for measuring the EMR reflected from the optical chamber or transmitted through the optical chamber. In some embodiments of the analyzer, more than one photodetector are arranged as a linear diode array in a spectrometer, the spectrometer also comprising a transmission or reflection grating for dispersing the reflected EMR or transmitted EMR, into component wavelengths. Therefore, the analyzer optionally provides optical measurement at one or more than one wavelength.

Another feature of the cartridge is the flexible member 345b of the cartridge 10b. This flexible member 345 may be depressed to generate pressurized air for mixing the sample with one or more dry reagent, and for advancing the sample towards the detection chamber in a regulated manner. This is facilitated by the fluid connection between an air bladder exit port 344b and a sample well 41b, via a cap recess 55b, illustrated in FIG. 5H. The flexible member can also be repeatedly depressed and released causing the blood to move forward and backward, in order to dissolve the one or more dry reagent in the blood sample, and provide better mixing of sample and reagent. In other embodiments, for example cartridge 10e, the recess 55e (see FIG. 15G), is in the cartridge body instead of the cap 51e. In each case a closed passage connecting an air bladder and a sample storage well is formed when the cartridge is adjusted from an unsealed to a sealed configuration.

A method for measuring a property of a blood sample comprises some or all of the following steps, not necessarily in the sequence given. One step is providing a cartridge (for example, one shown as 10b) and an analyzer comprising a slot or receptor for receiving a cartridge, the cartridge comprising one or more dry reagent deposited at one or more points before the detection chamber. Cartridge 10b comprises an optional mixing chamber 89, and a post capillary break conduit 91b, which defines the conduit between the capillary break 87b and the mixing chamber 89, illustrated in FIG. 5G. In some cartridge embodiments, the one or more reagent is deposited in the mixing chamber 89. Dry thromboplastin is an example of a reagent, which is used for measuring prothrombin time (PT) usually reported as PT-INR (PT-International Normalized Ratio), and dry celite or kaolin are examples of a reagent used for measuring activated clotting time (ACT).

In another step, the cartridge is placed flat on a table, and the cap 50b is rotated in a clockwise direction until the cap 50b hits the latch 70b, adjusting the cartridge 10b to the unsealed configuration, as illustrated in FIG. 6B. It should be noted that in the fully unsealed configuration, the cap 50b creates maximum opening of the top 43b of the sample storage well 41b, and at the same time, the cap 50b covers the air bladder exit port 344b, thereby mitigating, or modifying, flow of blood into the air bladder exit port 344b.

In another step, a blood sample is allowed to touch the top opening 43b of the sample storage well 41b. The blood is drawn into the sample storage well 41b and into the sample storage conduit 83b, up to the capillary break 87b (see FIG. 5G). Slightly excess blood is applied so that the blood sample bulges above the top opening 43b of the sample storage well 41b. For example, a finger of the patient may be pricked, and after a drop of blood is allowed to develop on the finger, following best practice procedures, a sample of the blood is introduced to the top opening 43b as described above.

In another step, the cap 50*b* is rotated counterclockwise into the recess 73*b* of the cap latch 70*b*, as illustrated in FIG. 6D. Details of the sample inlet portion 40*b* and its association with cap 50*b* are illustrated collectively in FIGS. 7A-7D. During the cap movement, the sweeping cap edge 58*b* skims off excess blood, which is dumped into the sample overflow well 47*b*. The volume of the metered blood is the volume of the sample storage well 41*b* and the volume of the sample storage conduit 83*b*. When the cap 50*b* is fully inserted into cap latch recess 73*b*, the cartridge in the sealed configuration. A person of ordinary skill will appreciate that an overflow well like 47*b* is useful for keeping all the blood in a contained system to avoid blood contamination of the analyzer, but it is not essential for the function of the cartridge or the metering system described herein.

In another step, the cartridge in the sealed configuration is inserted in the slot or receptor of the analyzer (not shown). The steps following cartridge insertion are automatically performed by the analyzer, and comprise depression of the flexible member 345*b*. The flexible member 345*b* can also be repeatedly depressed and released causing the blood to move forward and backward, in order to dissolve the dry one or more reagent in the blood sample. Depression or (repeated depression followed by release) of the flexible member 345*b* may be performed by a small stepper motor mounted on the receptor of the analyzer, but other means may be used that is known by a person skilled in the art. In the case of cartridge 10*b*, having an optional mixing chamber 89, the turbulence created as the blood sample flows into the mixing chamber 89 is sufficient to dissolve the one or more reagent, depending on the nature of the one or more reagent. It is known that some lyophilized reagents in relatively small quantities will dissolve almost immediately after the blood sample makes contact with the lyophilized substance, for example thromboplastin, used for measuring prothrombin time. It is also known that some reagents can be coated on the walls of a conduit, and more mixing is required to dissolve the reagents from the conduit walls.

In the case of cartridge 10, which has an optical detection chamber, another step is to apply a pre-developed calibration algorithm (see for example, U.S. Pat. No. 6,651,015 which is incorporated herein by reference) for hematocrit measurement to the optical measurement of the unclotted or clotted blood at one or more than one wavelength, and using the hematocrit measurement to correct the PT-INR for the patient's hematocrit.

Overview of Cartridges (Cartridges 10*c* and 10*d* as Non-Limiting Examples)

Disposable cartridges 10*c* and 10*d* for measuring a property of a sample, the cartridge having rapid sample metering systems, will now be described (See FIGS. 9A to 13B). The detection system is optical, but other embodiments of similar cartridges use different detection systems.

Shown in FIG. 9A is an exploded view of the disposable cartridge 10*c* for measuring a property of a sample, the cartridge having a rapid sample metering system, according to a third embodiment of the cartridge. This embodiment is similar to cartridge 10*b* and the major differences are as follows: a) The detection system is optical instead of electrochemical; b) The latch 70*c* is a pivotal latch having a pivot 62*c*, instead of a stationary latch 70*b* illustrated collectively in FIGS. 7A to 7D; c) The sample storage conduit 83*c* is disposed at the bottom of the second housing member 30*c*, defined by a groove 85*c* (see FIG. 9H) and a bottom cover 351*c*; and d) The cap 50*c* is designed differently and discussed in greater details later. Other differences will become apparent as the other drawings are described and viewed in conjunction with description of structural features provided in Table 1.

Shown in FIG. 9B is a bottom view of the first housing member 20*c* of the cartridge shown in FIG. 9A. Shown in FIG. 9C is the bottom view of the first housing member 20*c* shown in FIG. 9B, overlaid by and in alignment with the gasket 100*c* shown in FIG. 9A. Shown in FIG. 9D is a top view of the second housing member 30*c* of the cartridge shown in FIG. 9A. Shown in FIG. 9E is the top view of the second housing member 30*c* shown in FIG. 9D, overlaid by and in alignment with the gasket 100*c* shown in FIG. 9A.

Shown in FIG. 9F is a top view of the cartridge 10*c* shown in FIG. 9A, with the cartridge 10*c* in a sealed configuration and latch 70*c* engaged with the cap 50*c*. Shown in FIG. 9G is a front view of the cartridge 10*c* shown in FIG. 9F. Shown in FIG. 9H is a bottom view of the cartridge 10*c* shown in FIG. 9F, with bottom cover 351*c* (see FIG. 9A) removed to expose sample storage conduit entrance 81*c*, the sample storage conduit groove 85*c*, and the junction of sample storage conduit 83*c* and capillary break 87*c* (see FIG. 11B). Shown in FIG. 9J is a perspective view of the cartridge 10*c* shown in FIG. 9F. Shown in FIG. 9K is the perspective view of the cartridge 10*c* shown in FIG. 9J. with the cap 50*c* and latch 70*c* hidden. Shown in FIG. 9L is a top view of the cartridge 10*c* shown in FIG. 9A, with the cartridge in an unsealed configuration. Latch 70*c* is shown swiveled clockwise about 90 degrees from its position shown in FIG. 9F where the cartridge is shown in a sealed configuration.

Figure 10A:
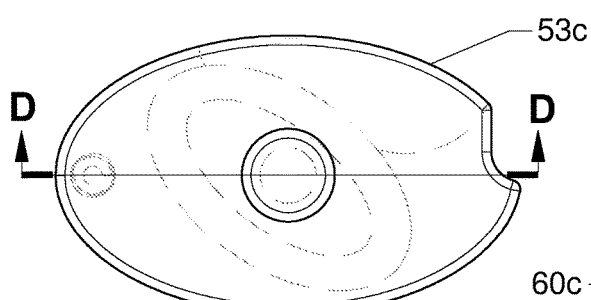
FIG. 10A is a top view of the cap 50c shown in FIGS. 9A, 9F, 9J and 9L.
Figure 10E:
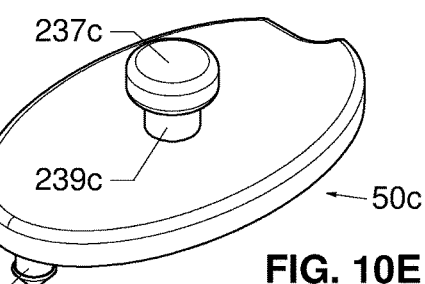
FIG. 10E is a perspective top view of the cap 50c shown in FIG. 10A.
Figure 10B:
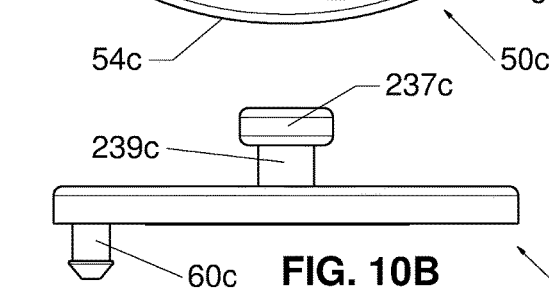
FIG. 10B is a front view of the cap 50c shown in FIG. 10A.

Illustrated collectively in FIGS. 10A-10H are details of the cap 50*c*. Shown in FIG. 10A is a top view of the cap 50*c* shown in FIGS. 9A, 9F, 9J and 9L, showing a sweeping portion 53*c* and a trailing portion 54*c* of cap 50*c*. Shown in FIG. 10B is a front view of the cap 50*c* shown in FIG. 10A, showing a pin 60*c* for hingedly attaching the cap to the sample inlet portion 40*c* and allowing the cap to swing with the gasket 57*c* (installed in cap 50*c*) frictionally engaged with the surface 49*c* of inlet portion 40*c*. Also shown is a crown 237*c* and a neck 239*c* of a cap knob of cap 50*c*, the neck 239*c* used for engaging the latch 70*c* and the crown 237*c* used for handling the cap 50*c*.

Figure 10F:
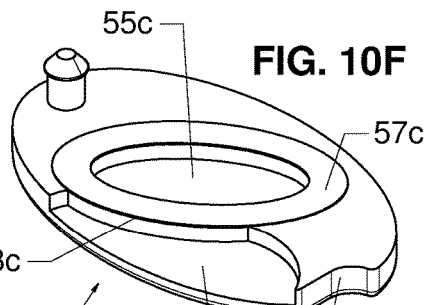
FIG. 10F is a perspective bottom view f the cap 50c shown in FIG. 100.
Figure 10C:
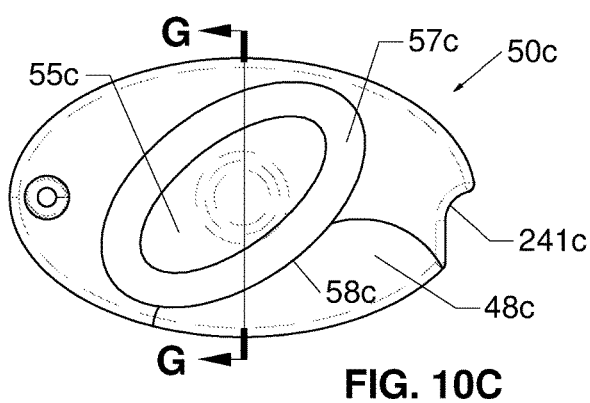
FIG. 10C is a bottom view of the cap 50c shown in FIG. 10A.
Figure 10G:
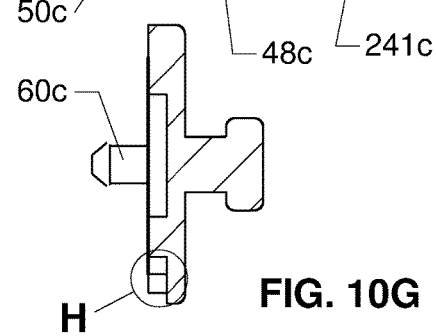
FIG. 10G is a cross-sectional view through the cap 50c shown in FIG. 100 along line G-G.
Figure 10D:
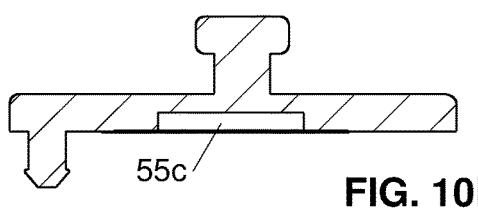
FIG. 10D is a cross-sectional view through the cap 50c shown in FIG. 10A along line D-D.
Figure 10H:
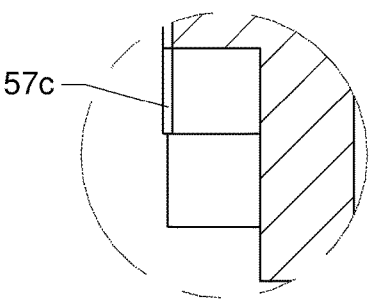
FIG. 10H is a detailed view of detail H of the cap 50c shown in FIG. 10G.

Shown in FIG. 100 is a bottom view of the cap 50*c* shown in FIG. 10A, showing a cap recess 55*c*, the gasket 57*c*, a groove 48*c* disposed at the underside and at the sweeping portion 53*c* of the cap 50*c*, for storing excess sample. Also shown is a sweeping cap edge 58*c* disposed at the sweeping portion 53*c* of cap 50*c* for skimming off excess sample, and a notch 241*c* in cap 50*c* for mating with pivot 62*c* of latch 70*c*, when cartridge 10*c* is in a sealed configuration. Shown in FIG. 10D is a cross-sectional view through the cap 50*c* shown in FIG. 10A along line D-D. Shown in FIG. 10E is a perspective view of the cap 50*c* shown in FIG. 10A. Shown in FIG. 10F is a perspective view of the cap 50*c* shown in FIG. 10C. Shown in FIG. 10G is a cross-sectional view through the cap 50*c* shown in FIG. 10C along line G-G. Shown in FIG. 10H is a detailed view of detail H of the cap 50*c* shown in FIG. 10G, showing the gasket 57*c* slighted elevated above the rest of the underside of the cap for creating the sweeping cap edge 58*c*.

Shown in FIG. 11A is a top view of the cartridge 10*c* (similar to the view shown in FIG. 9F) with the cartridge in a sealed configuration, for illustrating the internal structure. Shown in FIG. 11B is a first enlarged cross-sectional view through the cartridge 10*c* shown in FIG. 11A along line B-B. It should be noted that sufficient clearance between the crown 237*c* of the cap knob and the latch 70*c* is provided, and latch 70*c* is in contact with the cap 50*c*, for the latch 70*c* to apply force on the cap 50c when the cartridge in a sealed configuration. Also shown in FIG. 11B is the separate reagent chamber 209c and mixing chamber 89c. The perspective and top view of the reagent chamber 209c and the portion 89c" of mixing chamber 89c in a second housing member 30c, are shown in FIG. 9A and FIG. 9D respectively. The volume of the mixing chamber is substantially larger than the volume of the reagent chamber, and the two chambers are fluidly connected by a narrow conduit 210c. After the sample fills the reagent chamber 209c containing the dry reagent, the reagent and sample are mixed more thoroughly after the partially mixed sample and reagent are ejected into the larger mixing chamber 89c, by turbulence. Shown in FIG. 11O is a second enlarged cross-sectional view through the cartridge 10c shown in FIG. 11A along line C-C, showing the optical chamber 211c and having an overflow conduit 227c and a vent 233c for relieving pressure and therefore allowing flow. Shown in FIG. 11D is a third enlarged cross-sectional view through the cartridge 10c shown in FIG. 11A along line D-D. Shown in FIG. 11E is a fourth enlarged cross-sectional view through the cartridge 10c shown in FIG. 11A along line E-E. By way of example, latch 70c is engaged with cap 50c in a similar manner as illustrated in FIG. 6F, for the engagement of cap 50b in cartridge 10b.

Figure 12A:
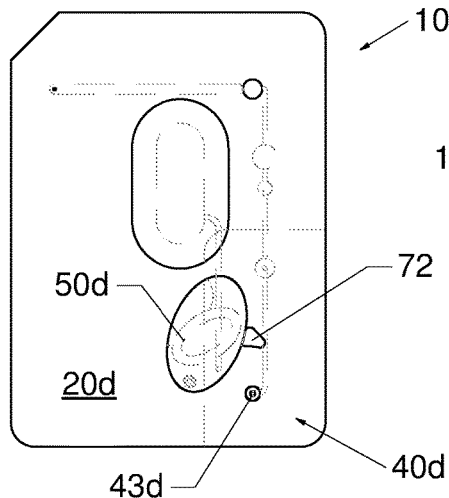
FIG. 12A is top view of the disposable cartridge 10d for measuring a property of a sample, the cartridge having a rapid sample metering system, according to a fourth embodiment of the cartridge, in a fully open position.
Figure 12B:
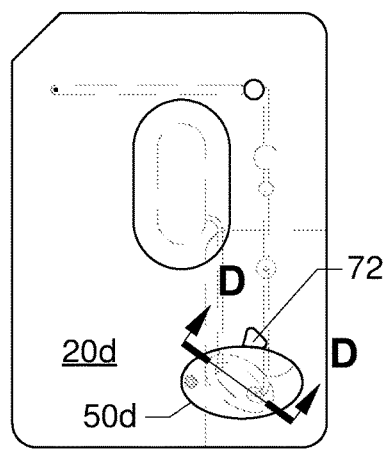
FIG. 12B is top view of the disposable cartridge 10d shown in FIG. 12A, but in a fully closed position.
Figure 12C:
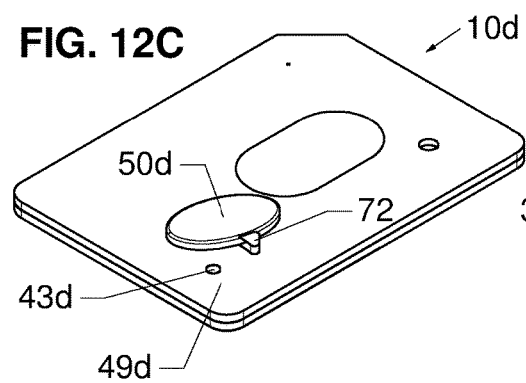
FIG. 12C is perspective top view of the disposable cartridge 10d shown in FIG. 12A (in a fully open position)

Shown in FIG. 12A is top view of the disposable cartridge 10d for measuring a property of a sample, the cartridge having a rapid sample metering system, according to a fourth embodiment of the cartridge, in an unsealed configuration. Cartridge 10d is like cartridge 10c illustrated collectively in FIGS. 9A-9L. The major differences are: a) The cap 50d does not have a knob (239c & 237C) or a notch 241c; b) The cartridge 10c does not have a latch 70c; and c) The cartridge 10d comprises a cap stop for keeping cartridge 10d in either an unsealed configuration or a sealed configuration. Shown in FIG. 12B is top view of the disposable cartridge 10d shown in FIG. 12A, but in a sealed configuration. Shown in FIG. 12C is perspective view of the disposable cartridge 10d shown in FIG. 12A (in an unsealed configuration).

Figure 12D:
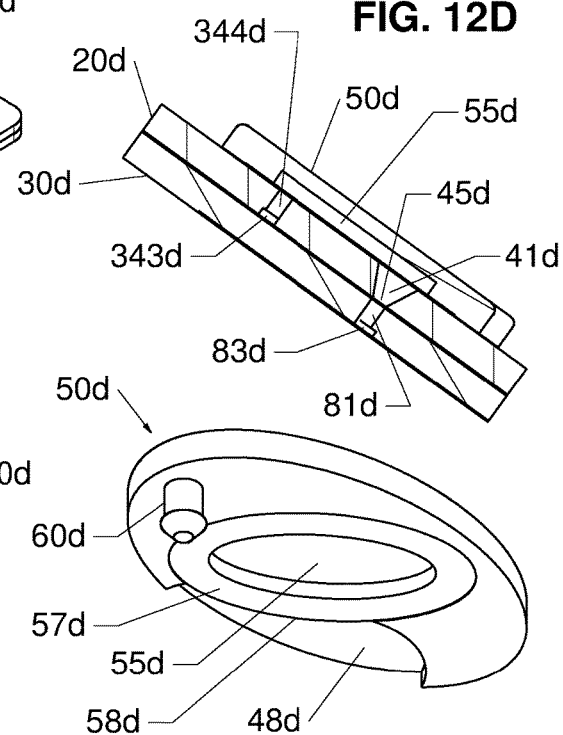
FIG. 12D is an enlarged cross-sectional view through the cartridge 10d shown in FIG. 12B along line D-D.

Shown in FIG. 12D is an enlarged cross-sectional view through the cartridge 10d shown in FIG. 12B along line D-D, showing the cap recess 55d providing a closed air passage connecting the air bladder exit port 344d and the sample storage well 41d for communicating the pressurized air from the air bladder exit port to the sample storage well for urging the sample into the reagent chamber (See 209c in FIG. 11B for cartridge 10c), the mixing chamber (See 89c in FIG. 11B for cartridge 10c), and the optical chamber (See 211c in FIG. 11C for cartridge 10c), in that order.

Figure 13A:
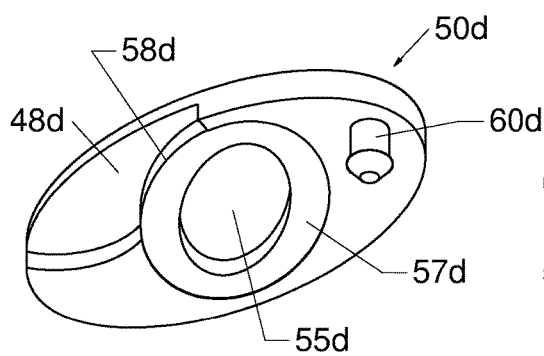
FIG. 13A is a first perspective bottom view of the cap 50d shown in FIG. 12A, showing the underside.
Figure 13B:
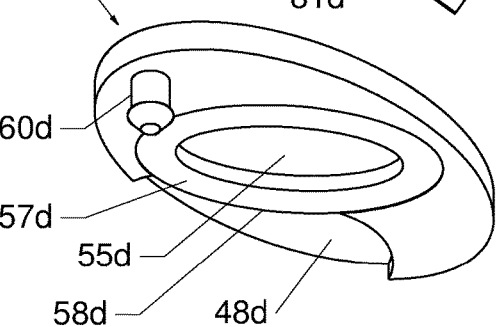
FIG. 13B, is a second perspective bottom view of the cap 50d shown in FIG. 12A, showing the underside.

Shown in FIG. 13A is a first perspective view of the cap 50d shown in FIG. 12A, showing the underside, and shown in FIG. 13B is a second perspective view of the cap 50d shown in FIG. 12A, showing the underside.

Sample Measurement

The following is a brief description of a system for metering a sample and measuring a property of the sample, using one of the cartridges previously described explicitly or implicitly. The system further comprises an analyzer. The analyzer comprises: a) a receptor for receiving the cartridge; b) one or more than one processor for controlling the analyzer; c) means for activating the air bladder; and d) a detector for receiving the signal from the detection chamber and sending the signal to the one or more than one processor for transforming the signal into the property of the sample.

The following is a description of a method for measuring a property of a blood sample, using one of the cartridges previously described explicitly or implicitly. The method comprises: a) providing the cartridge in an unsealed configuration; b) providing an analyzer comprising: 1) a receptor for receiving the cartridge; 2) one or more than one processor for controlling the analyzer; 3) means for activating the air bladder; and 4) a detector for receiving the signal from the detection chamber and sending the signal to the one or more than one processor for transforming the signal into the property of the sample; c) obtaining a blood sample by pricking a body part and depositing the blood sample into the sample storage well, or depositing blood from a syringe into the sample storage well; d) rotating the cartridge cap about the pin and skimming off excess blood; e) arranging the cartridge in a sealed configuration, wherein the cap recess facilitates provision of a closed air passage connecting the air bladder exit port and the sample storage well for communicating pressurized air from the air bladder exit port to the sample storage well for urging the blood towards the detection chamber; f) inserting the sealed cartridge into the analyzer receptor; g) activating the air bladder for providing the pressurized air; h) dissolving the one or more than one reagent into the blood; i) urging the mixture of blood and the one or more than one reagent into the detection chamber; and j) measuring the property of the blood sample.

Some methods for measuring a property of a blood sample, for example prothrombin time (or activated clotting time), further comprise: a) providing a cartridge further comprising an optical chamber; b) providing an analyzer further comprising a source of electromagnetic radiation and a detector for collecting electromagnetic radiation transmitted through the optical chamber or reflected from the optical chamber; c) applying a pre-determined calibration algorithm to the collected electromagnetic radiation to measure hematocrit of the blood sample to produce a hematocrit measurement; and d) using the hematocrit measurement to correct the property of the blood sample, for example prothrombin time (or activated clotting time), for the actual plasma volume in the blood sample.

Overview of Cartridges (Cartridges 10e, 10f and 10g as Non Limiting Examples)

Described next are the fifth, sixth and seventh embodiments of a disposable cartridge (see FIGS. 14A to 19H). These embodiments provide more space at the cartridge inlet and free from obstruction, in order to accommodate larger fingers and a baby's heel, when these body parts are used to provide the blood sample. Another advantage of the fifth, sixth and seventh embodiments is the option to choose from a larger selection of plastics for manufacturing the cartridges. As previously mentioned, an aspect of the present invention is an optical chamber, which is preferably made of transparent plastic and is easily manufactured by for example, injection molding. Some very transparent plastics, for example Polymethyl methacrylate (PMMA, plexiglass) and PET, are advantageous in terms of optical clarity and can be injection molded but may not be sufficiently wettable for the purpose of drawing blood into the optical chamber by capillary action. The fifth, sixth and seventh embodiments of a cartridge as illustrated, can optionally function without relying on capillary action to draw the blood into the optical chambers of the cartridges. Also described is another system for hingedly connecting caps 50e and 50f to the bodies of cartridges 10e and 10f respectively, in which like the previous embodiments, a closed passage is provided for connecting the air bladder exit port to the sample storage well for communicating the pressurized air from the air bladder exit port to the sample storage well. When the air bladder is squeezed, metered blood is urged from the sample storage well, and the volume of blood urged is determined by the extent to which the air bladder is squeezed. Although the cartridges provide a combination of an optical chamber and a biosensor chamber, some embodiments comprise a cap hinged like 50e or 50f, and one of an optical chamber and a biosensor chamber comprising one or more biosensors.

Shown in FIG. 14A is an exploded top view of the disposable cartridge 10e, with cap 50e in an open configuration, for measuring a property of a sample, according to a fifth embodiment of the cartridge. The underside 52e of the cap 50e is shown as a flat surface having no recess, unlike cap 50b of cartridge 10b, which has a recess 55b (see FIGS. 5H, 8F & 8G). Instead of a recess in the cap, channel 55e in the cartridge body is used to facilitate formation of a closed passage for connecting the air bladder exit port 344e to the sample storage well 41e (see FIGS. 15G and 15H). Also, the gasket 57e is installed in the first housing member 20e (see FIG. 15B), unlike gasket 57c, which is installed in the cap 50c of cartridge 10c (see FIGS. 100 and 10H). Another difference in cartridge 10e is the system used for hingedly connecting the cap 50e to the body of cartridge 10e.

Shown in FIG. 14B is a bottom view of the first housing member 20e of the cartridge shown in FIG. 14A. Shown in FIG. 140 is the bottom view of the first housing member 20e of the cartridge shown in FIG. 14B, overlaid by and in alignment with the gasket 100e shown in FIG. 14A. Shown in FIG. 14D is a top view of the second housing member 30e of the cartridge shown in FIG. 14A. Shown in FIG. 14E is the top view of the second housing member 30e shown in FIG. 14D, overlaid by and in alignment with the gasket 100e shown in FIG. 14A.

Shown in FIGS. 15A and 15B are perspective top views of the cartridge 10e in a closed and an open configuration, respectively, facilitated by hinges 60e' and 60e". Shown in FIG. 15C is a top view of the cartridge 10e in a closed configuration. Shown in FIG. 15D is a first cross-sectional view through the cartridge 10e shown in FIG. 15C along line D-D. Shown in FIG. 15E is a detailed view of detail E of the cartridge shown in FIG. 15D. Depending on the wetting ability (discussed previously in the context of contact angles, provided in Table 2) of the sample storage conduit 83e (FIGS. 15E and 15H), enlarge cavity 46 near the bottom opening 45e of sample storage well 41e of cartridge 10e provides an optional example of a means for mitigating (or modifying) blood flow out of the sample storage well 41e, except when the air bladder 340e (FIG. 15H) is squeezed. In other examples, enlarged cavity 46 may be disposed around either optical chamber entrance 207e or optical chamber exit 212e (see FIG. 15H). The enlarged cavity disposed at the optical chamber entrance may prevent blood from flowing into the optical chamber, except when the air bladder is squeezed. In some embodiments that have a sample storage conduit 83e with sufficient wetting ability, the enlarged cavity 46 may be disposed near the exit of the optical chamber 211e, and blood flow by capillary action is allowed to proceed into the optical chamber 211e and stop at the enlarged cavity, so that no blood enters the biosensor chamber. In embodiments where the enlarged cavity 46 is disposed near the exit of the optical chamber 211e (described in U.S. Pat. No. 9,470,673 and patent application PCT/CA20171050379, which are incorporated herein by reference), the cartridges also comprise a biosensor chamber (e.g., 337e in FIG. 15H), and the cartridge optionally comprises biosensor calibration means (described in U.S. Pat. No. 9,470,673, patent application PCT/CA2017/050379 and U.S. Pat. No. 5,096,669, which are incorporated herein by reference). In embodiments having biosensor calibration means, blood is only allowed to enter the biosensor chamber 337e (see FIG. 15H) after the biosensors are calibrated, therefore the blood must be metered up to a safe distance from the biosensor chamber. Some embodiments may comprise an enlarge cavity disposed at a point between the optical chamber exit 212e and the biosensor entrance 336e (see FIG. 15H), depending on the location of the calibration fluid entry point, whereby the calibration fluid may come from a calibration fluid pouch installed in the cartridge as described in U.S. Pat. No. 9,470,673, patent application PCT/CA2017/050379, or the calibration fluid may come from a fluid pack installed in the analyzer as described in U.S. Pat. No. 9,901,928 to Lin et al. Other know means for calibrating biosensors that require calibration, are considered to be within the scope of the present invention. If calibration fluid comes from a fluid pack installed in the analyzer, the cartridge may comprise an inlet port for receiving the calibration fluid, for example without any limitations, inlet ports described in U.S. Pat. No. 9,901,928 to Lin et al. After calibration of the biosensors, pressurized air from the air bladder 340e is used to regulate the flow of blood out of the optical chamber and into the biosensor chamber 337e, the blood displacing the calibration fluid in the biosensor chamber and forcing the calibration fluid out into the waste receptacle 231e (see FIG. 15H). Preferably, the blood must travel to a point between the exit of the biosensor chamber 337e and the waste chamber 231e to ensure that all the sensors in the biosensor chamber 337e are covered with blood. Although calibration means are not illustrated in any of the cartridge embodiments, optional calibration means are considered to be within the scope of the present invention. Requirement of biosensor calibration depends on the property of the blood sample measured, and the accuracy goal of the property measurement. Examples of blood properties are electrolytes, blood gases and pH measured in the biosensor chamber, and CO-oximetry measured in the optical chamber.

Shown in FIG. 15F is a cross-sectional view through the cartridge 10e shown in FIG. 15C along line F-F. Shown in FIG. 15G is a detailed view of detail G of the cartridge shown in FIG. 15F. Channel 55e in the cartridge body is used to facilitate formation of a closed passage for connecting the air bladder exit port 344e to the sample storage well 41e (see FIG. 15G), instead of a recess 55f in a similar cap 50f in cartridge 10f (see FIG. 17G). A cap hinge 60e" and latch 75e are also shown in FIG. 15G. In cartridge 10e, two hinges (60e' and 60e") are shown by way of example only, and other hinged configurations may also be used as would be known to one of skill in the art. The latch 75e is designed to engage with cap latch catch 74e (see FIGS. 15B and 15H), in a snap-fit manner.

Shown in FIG. 15H is a top view of the cartridge 10e, with the cap removed for better viewing of structural details. For illustrative purposes, holes 61e and 61e are shown, and these holes are for anchoring hinges 60e' and 60e" for hingedly attaching cap 50e to the body of cartridge 10e. However, in some embodiments, cap 50e may be an integral part of the cartridge. Other known designs in the hinges and latching system are consider to be within the scope of the present invention.

Also shown in FIG. 15H is a blood shunt 86e for bypassing optical chamber 211e, and providing fluid connection between sample storage well 41e and biosensor conduit 337e. In this embodiment, by way of example, the depth of the optical chamber 211e is optionally equivalent to the thickness of gasket 100e. The outline of the blood shunt 86e and the optical chamber 211e is defined as gasket cut-out 117e (see in FIG. 14A), positioned to align at least partly with at least one of optical windows 213e and 215e (located in first housing member 20e and second housing member 30e, respectively; see FIG. 15E). As an example, the thickness of the gasket 100e may be about 0.1 millimeter, and instead of forcing the blood through the optical chamber 211e (located in the gasket layer 100e) to get to the biosensor chamber 337e, it is preferred to have a bypass route of larger cross-sectional area. Shown in FIG. 15E, viewed in conjunction with FIG. 15H, is shunt 86e which circumvents the optical chamber 211e. This circumvention is preferred: 1) to mitigate lysis of the red blood cells (i.e., hemolysis) if the red blood cells are forced through a narrow opening like the opening defined the cross-section of the optical chamber 211e; and 2) to ensure that any obstruction in the optical chamber, for example due to clotting of blood, will not prevent the blood from flowing from the sample storage well 41e to the biosensor chamber 337e.

Shown in FIG. 16A is an exploded top view of the disposable cartridge 10f in an open configuration, for measuring a property of a sample, according to a sixth embodiment of the cartridge. Shown in FIG. 16B is a bottom view of the first housing member 20f of the cartridge shown in FIG. 16A. Shown in FIG. 16C is the bottom view of the first housing member 20f of the cartridge shown in FIG. 16B, overlaid by and in alignment with the gasket 100f shown in FIG. 16A. Shown in FIG. 16D is a top view of the second housing member 30f of the cartridge shown in FIG. 16A. Shown in FIG. 16E is the top view of the second housing member 30f shown in FIG. 16D, overlaid by and in alignment with the gasket 100f shown in FIG. 16A. Shown in FIGS. 17A and 17B are perspective top views of the cartridge 10f in a closed and an open configuration respectively, facilitated by hinges 60f′ and 60f″, showing the cap recess 55f (within the underside of cap 52f) and the sealing gasket 57f in FIG. 17B. The cap recess 55f and the sealing gasket 57f are two differences between cartridges 10e and 10f.

Shown in FIG. 17C is a top view of the cartridge 10f in a closed configuration. Shown in FIG. 17D is a first cross-sectional view through the cartridge 10f shown in FIG. 170 along line D-D. Shown in FIG. 17E is a detailed view of detail E of the cartridge shown in FIG. 17D. Shown in FIG. 17F is a second cross-sectional view through the cartridge 10e shown in FIG. 17C along line F-F. Shown in FIG. 17G is a detailed view of detail G of the cartridge shown in FIG. 17F.

A third difference between cartridges 10e and 10f is that the sample storage well 41f is cylindrical in shape instead of the conical-like sample storage well 41e (see FIG. 15G). However, any shape of the sample storage well is considered to be within the scope of the present invention. A fourth difference is that the bottom opening (bottom portion) 45f of sample storage well 41f coincides with an entrance to the sample storage conduit 83f, with bottom opening 45f disposed at the bottom side of the storage well 41f (see FIG. 17G). An advantage of the cylindrical shape over a conical-like shape is an increased sample storage well capacity, for cartridges having the same thickness of the first housing members (20f and 20e). Although the top opening 43f of a sample storage well 41f is illustrated as circular, non-circular opening is optional. A larger top opening also provides additional sample well storage capacity. In POCT, small sample size is highly desirable, but a larger sample size is preferred for measurement of blood properties like blood gases, in particular partial pressure of oxygen ($pO_2$), for the following reason: since air contains 21% oxygen, the error in $pO_2$ measurement caused by inclusion of an air bubble in the sample is directly proportional to the size of the air bubble and inversely proportional to the sample size.

Another reason why a top opening, or top portion, of a sample storage well is preferred to be larger relative to the bottom opening is that it is easier to deposit a pin prick drop of blood accumulated on the skin of a body part, or blood from a syringe, into the sample well when the area of the top opening of the well is sufficiently large. Therefore, a preferred area of a sample well top opening (e.g. 43f, FIG. 17H) for any of the embodiments described herein, is in the range of about 10 mm$^2$ (square millimeters) to about 150 mm$^2$, or any amount there between, and a preferred area of a sample well bottom opening (e.g. 45f) for any of the embodiments described herein is in the range of about 0.01 mm$^2$ to about 10 mm$^2$, or any amount there between. A more preferable area of a sample well top opening (e.g. 43f) for any of the embodiments described herein is in the range of about 15 mm$^2$ to about 100 mm$^2$, or any amount there between, and a more preferable area of a sample well bottom opening (e.g. 45f) for any embodiment described herein is in the range of about 0.05 mm$^2$ to about 5 mm$^2$, or any amount there between.

Figure 17H:
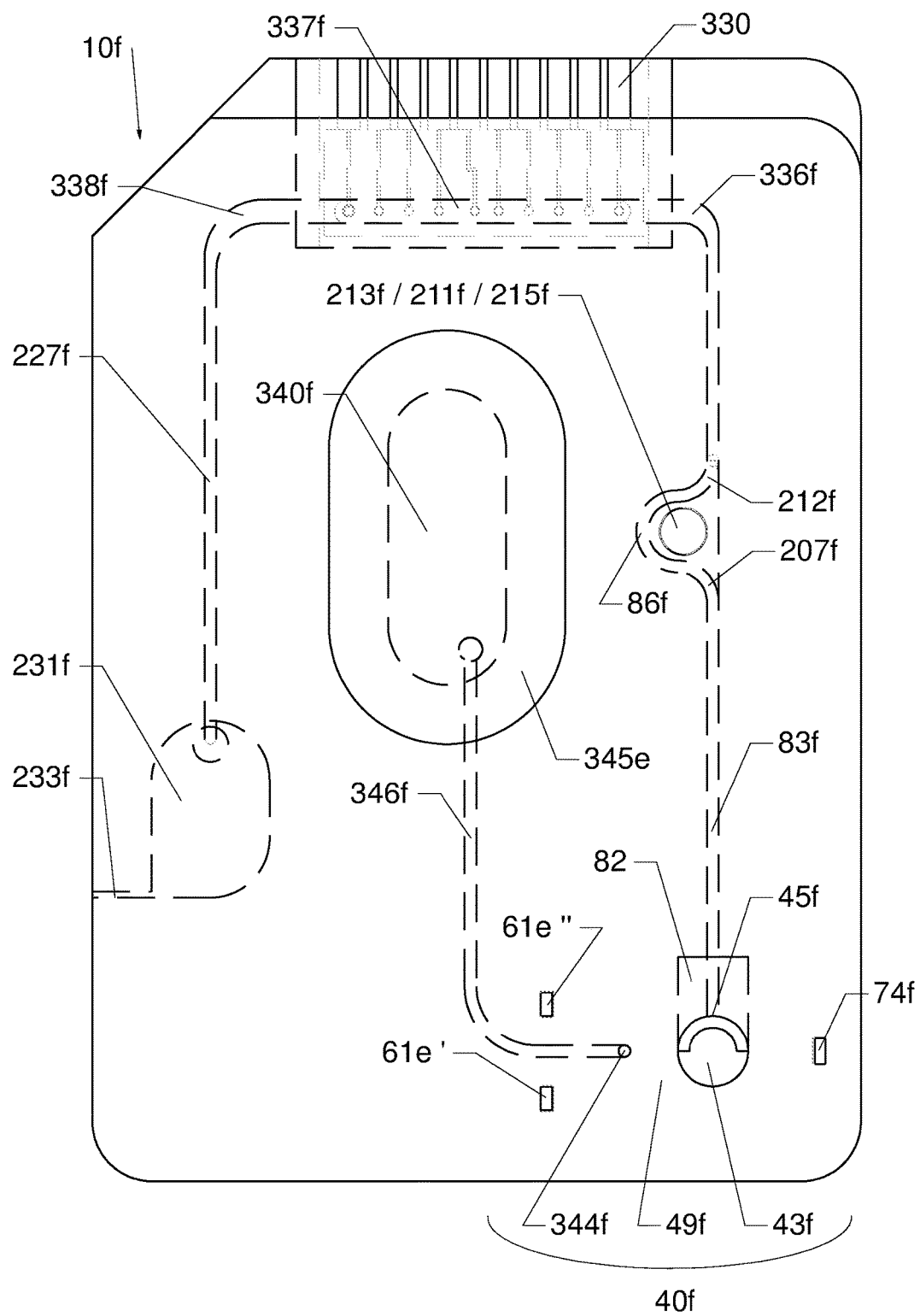
FIG. 17H is a top view of the cartridge 10*f*, with the cap hidden.

Shown in FIG. 17H is a top view of the cartridge 10f, with the cap removed. Another means for mitigating (or modifying) blood flow out of the sample storage well is to make all or part of the sample storage conduit less wettable. Alternatively, as illustrated in FIG. 17H, a hydrophobic insert 82 is disposed near the entrance of sample storage conduit 83f for providing means for mitigating blood flow out of the sample storage well, except when the air bladder is squeezed. Other structural features that provide means for mitigating blood flow out of the sample storage well, except when the air bladder is squeezed, are considered to be within the scope of the present invention. Therefore, depending on the plastic used to manufacture the cartridge, hydrophobic insert 82 in cartridge 10f and the enlarged cavity 46 in cartridge 10e are optional. Also, the stringency of the requirement to mitigate blood flow from the sample storage well (e.g. 41f) into the sample storage conduit (e.g. 83f) depends on the property of the blood measured. For example, a blood property measurement that requires a fixed amount a reagent (e.g., PT-INR) has a more stringent requirement to mitigate blood flow from the sample storage well (e.g. 41f) into the sample storage conduit (e.g. 83f) than a property that does require a reagent (e.g., CO-oximetry). In other words, the metering requirement for PT-INR is more stringent than the metering requirement for CO-oximetry.

Figure 18A:
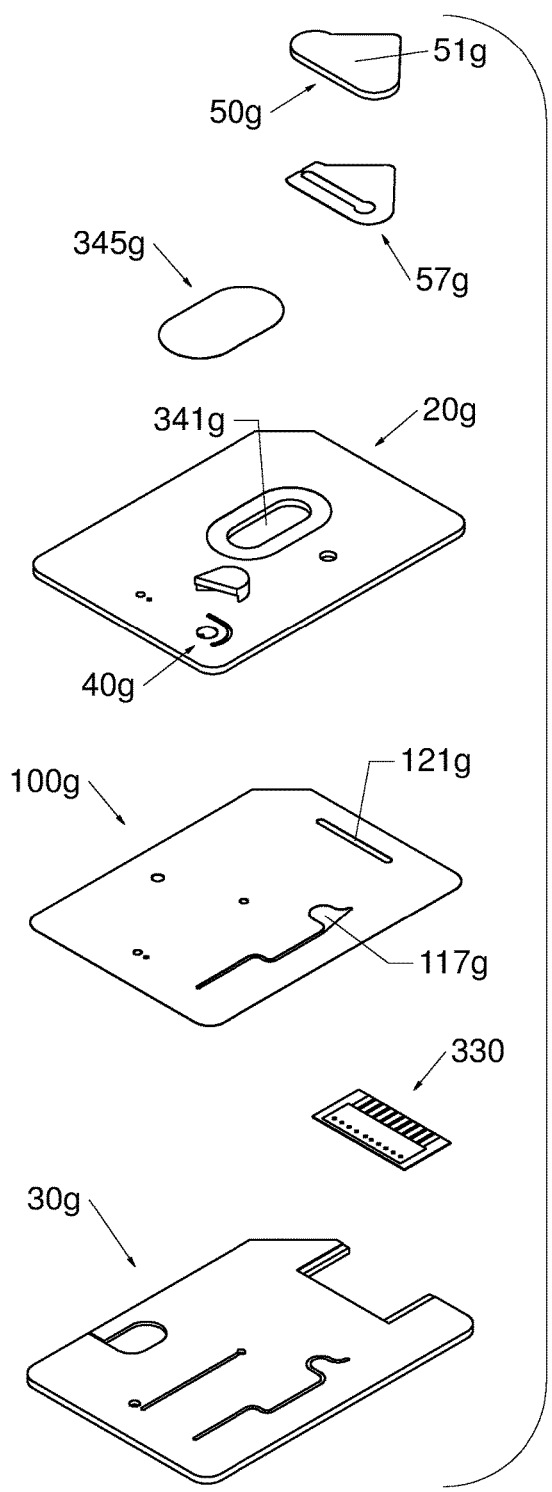
FIG. 18A is an exploded top view of the disposable cartridge 10*g* in an open configuration, for measuring a property of a sample, according to a seventh embodiment of the cartridge.

Shown in FIG. 18A is an exploded top view of the disposable cartridge 10g in an open configuration, for measuring a property of a sample, according to a seventh embodiment of the cartridge. Cartridge 10g comprises both an optical chamber 211g (see FIG. 19E) and a biosensor chamber 337g (see FIG. 19H).

An additional feature of cartridge 10g is the ability to accommodate larger fingers and a baby's heel, when these body parts are used to provide the blood sample. Also, the top opening 43g of the sample storage well 41g can be made relatively large, making the sample storage well 41g more accessible for delivery of a pin prick drop of blood, or delivered of blood from a syringe.

Figure 18B:
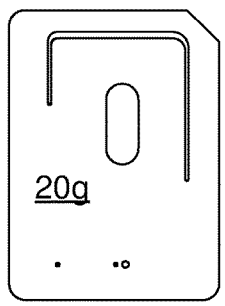
FIG. 18B is a bottom view of the first housing member 20*g* of the cartridge shown in FIG. 18A.
Figure 18C:
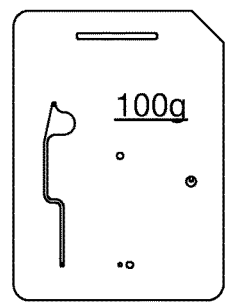
FIG. 18C is the bottom view of the first housing member 20*g* of the cartridge shown in FIG. 18*6*, overlaid by and in alignment with the gasket 100*g* shown in FIG. 18A.
Figure 18D:
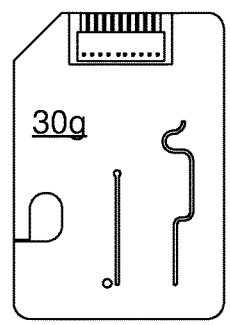
FIG. 18D is a top view of the second housing member 30*g* of the cartridge shown in FIG. 18A.
Figure 18E:
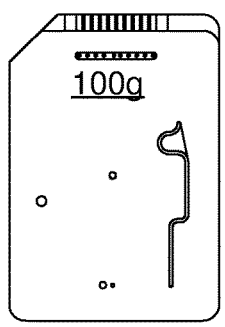
FIG. 18E is the top view of the second housing member 30*g* shown in FIG. 18D, overlaid by and in alignment with the gasket 100*g* shown in FIG. 18A.

Shown in FIG. 18B is a bottom view of the first housing member 20g of the cartridge shown in FIG. 18A. Shown in FIG. 18C is the bottom view of the first housing member 20g of the cartridge shown in FIG. 18B, overlaid by and in alignment with the gasket 100g shown in FIG. 18A. Shown in FIG. 18D is a top view of the second housing member 30g of the cartridge shown in FIG. 18A. Shown in FIG. 18E is the top view of the second housing member 30g shown in FIG. 18D, overlaid by and in alignment with the gasket 100g shown in FIG. 18A.

Figure 19H:
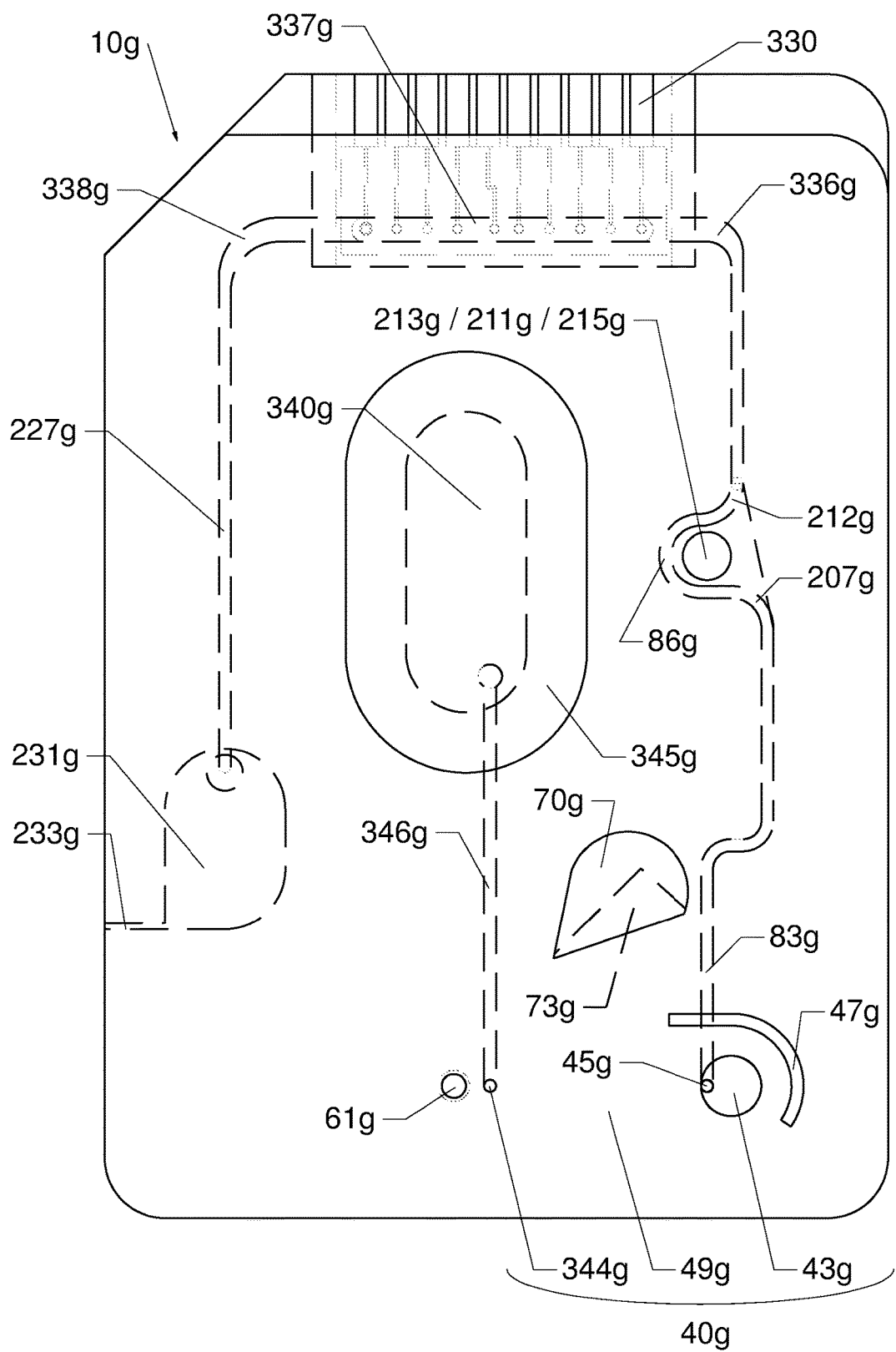
FIG. 19H is a top view of the cartridge 10*g*, with the cap hidden.

Shown in FIG. 19A is a perspective top view of the cartridge 10g in a closed configuration. Shown in FIG. 19B is a perspective top view of the cartridge 10g in an open configuration. Shown in FIG. 19C is a top view of the cartridge 10g in a closed configuration. Shown in FIG. 19D is a first cross-sectional view through the cartridge 10g shown in FIG. 19C along line D-D. Shown in FIG. 19E is a detailed view of detail E of the cartridge shown in FIG. 19D. Shown in FIG. 19F is a second cross-sectional view through the cartridge 10g shown in FIG. 19C along line F-F. Shown in FIG. 19G is a detailed view of detail G of the cartridge shown in FIG. 19F. Shown in FIG. 19H is a top view of the cartridge 10g, with the cap removed.

It will be appreciated that although cartridges 10e, 10f and 10g are describe having both an optical chamber and a biosensor chamber, a cartridge may comprise either one or more optical chamber, or one or more biosensor chamber. It will also be appreciated that an optical chamber and a biosensor chamber are non-limiting examples of detection chambers.

Sample Measurement

The following is a description of a method for measuring one or more properties of a blood sample, using one of the cartridges previously described explicitly or implicitly. The method comprises: a) providing the cartridge in an unsealed configuration; b) providing an analyzer comprising: 1) a receptor for receiving the cartridge; 2) one or more than one processor for controlling the analyzer; 3) means for activating the air bladder; and 4) one or more detectors for receiving the one or more signals from the one or more detection chambers and sending the one or more signals to the one or more than one processor for transforming the one or more signals into the one or more properties of the sample; c) obtaining a blood sample by pricking a body part and depositing the blood sample into the sample storage well, or depositing blood from a syringe into the sample storage well; d) rotating the cartridge cap about the hinge for adjusting the cartridge from an unsealed configuration to a sealed configuration, wherein a recess in either the cap or the cartridge body facilitates provision of a closed air passage connecting the air bladder exit port and the sample storage well for communicating pressurized air from the air bladder exit port to the sample storage well for urging the blood towards the detection chamber; e) inserting the sealed cartridge into the analyzer receptor; g) activating the air bladder for providing the pressurized air; h) urging the blood or a mixture of the blood and one or more reagents into the detection chamber; and j) measuring the one or more properties of the blood sample.

Some methods for measuring a property of a blood sample, for example prothrombin time (or activated clotting time), may further comprise dissolving the one or more than one reagent into the blood; prior to urging the mixture of blood and the one or more reagents into the detection chamber.

Other methods for measuring a property of a blood sample, for example prothrombin time (or activated clotting time), may further comprise: a) providing a cartridge in an unsealed configuration, further comprising an optical chamber; b) providing an analyzer further comprising a source of electromagnetic radiation and a detector for collecting electromagnetic radiation transmitted through the blood in the optical chamber or reflected from the blood in the optical chamber; c) applying a pre-determined calibration algorithm to the collected electromagnetic radiation to measure hematocrit of the blood sample to produce a hematocrit measurement; and d) using the hematocrit measurement to correct the property of the blood sample, for example prothrombin time (or activated clotting time), for the actual plasma volume in the blood sample.

Sample Measurement (Using Cartridges 10e, 10f and 10g as Non-Limiting Examples)

The following is a description of a method for measuring a plurality of properties of a blood sample, using one of cartridges 10e, 10f or 10g previously described explicitly or implicitly. The method comprises: a) providing the cartridge; b) providing an analyzer comprising: 1) a receptor for receiving the cartridge; 2) one or more than one processor for controlling the analyzer; 3) means for activating the air bladder; 4) a source of electromagnetic radiation for interrogating the blood in the optical chamber; and 5) one or more detectors for receiving the signals from the optical chamber and the biosensor chamber and sending the signals to the one or more than one processor for transforming the signals into the plurality of properties of the sample; c) obtaining a blood sample by pricking a body part and depositing the blood sample into the sample storage well, or depositing blood from a syringe into the sample storage well; d) rotating the cartridge cap about the hinge and arranging the cartridge in a sealed configuration, wherein the cap recess or the channel in the cartridge body facilitates provision of a closed air passage connecting the air bladder exit port and the sample storage well for communicating pressurized air from the air bladder exit port to the sample storage well for urging the blood towards the detection chamber; f) inserting the sealed cartridge into the analyzer receptor; g) activating the air bladder for providing the pressurized air; h) urging the blood into the optical chamber and stopping the leading edge of the blood between the optical chamber exit and the biosensor chamber entrance, if biosensor calibration is required, or urging the blood into the optical chamber and subsequently into the biosensor chamber and stopping the leading edge of the blood between the biosensor chamber exit and the cartridge vent, if biosensor calibration is not required, wherein if the leading edge of the blood is stopped between the optical chamber exit and the biosensor chamber entrance, the method further comprises calibrating the one or more biosensors prior to urging the blood into the biosensor chamber and stopping the leading edge of the blood between the biosensor chamber exit and the cartridge vent; and j) measuring the plurality of properties of the blood sample.

While the above description provides example embodiments, it will be appreciated that the present invention is susceptible to modification and change without departing from the fair meaning and scope of the accompanying claims. Accordingly, what has been described is merely illustrative of the application of aspects of embodiments of the invention. Numerous modifications and variations of the present invention are possible in light of the above teachings. It is therefore to be understood that within the scope of the appended claims, the invention may be practiced otherwise than as specifically described herein. Furthermore, the discussed combination of features might not be absolutely necessary for the inventive solution.

I claim:

1. A disposable cartridge comprising:
a cartridge body comprising an upper surface and a lower surface;

a sample inlet portion located on the upper surface, the sample inlet portion comprising:
a sample storage well for storing at least a portion of a sample, the sample storage well comprising a top portion for receiving a blood sample and a bottom portion for releasing at least some the blood sample into a sample storage conduit, wherein the top area is substantially larger than the bottom area;
an air bladder exit port located on the upper surface,
a flat surface of the cartridge body located on the upper surface, the flat surface of the cartridge body surrounding the top portion and the air bladder exit port;
the sample storage conduit for transferring at least some of the blood from the sample storage well to an optical chamber;
the optical chamber for generating signals during sample interrogation, the signals used to calculate one or more properties of the blood sample;
an air bladder for providing pressurized air, the air bladder operatively connected with the air bladder exit port;
a vent in operative communication with the optical chamber, the vent for relieving pressure in the optical chamber;
a cap hingedly connected to the cartridge body via a hinge, the cap having a top side and an underside, wherein at least a portion of the underside comprises a cap flat surface;
wherein, the disposable cartridge is adjustable between an unsealed configuration and a sealed configuration by rotating the cap about the hinge;
in the unsealed configuration the sample storage well is configured to receive the blood sample; and
in the sealed configuration a portion of the flat surface of the cartridge body mates with a portion of the cap flat surface to form a closed air passage operatively connecting the air bladder exit port to the sample storage well so that pressurized air from the air bladder exit port is transferable to the sample storage well, and when the air bladder is squeezed blood is urged from the sample storage well towards the optical chamber, and
wherein the closed air passage is facilitated by a groove set into the upper surface of the cartridge body, a recess set into the underside of the cap, or a combination thereof.

2. The disposable cartridge of claim 1, wherein the top area is in a range of about 10 square millimeters to about 150 square millimeters, and the bottom area is in a range of about 0.01 square millimeters to about 10 square millimeters.

3. The disposable cartridge of claim 1, wherein the top area is in a range of about 15 square millimeters to about 100 square millimeters, and the bottom area is in a range of about 0.05 square millimeters to about 5 square millimeters.

4. The disposable cartridge of claim 1, further comprising means for mitigating blood flow out of the sample storage well, except when the air bladder is squeezed.

5. The disposable cartridge of claim 1, wherein the closed passage comprises the recess set into the underside of the cap.

6. The disposable cartridge of claim 1, wherein the closed passage comprises a groove set into the upper surface of the cartridge body.

7. The disposable cartridge of claim 1 further comprising a biosensor chamber disposed between an exit of the optical chamber and the vent, the biosensor chamber comprising one or more biosensors for generating signals used to calculate one or more properties of the blood sample.

8. The disposable cartridge according to claim 1, further comprising at least one reagent in the sample storage conduit.

9. The disposable cartridge according to claim 1, further comprising a mixing chamber disposed in the sample storage conduit.

10. The disposable cartridge of claim 1, wherein the flat surface of the cartridge body comprises a gasket that surrounds the top portion and the air bladder exit port.

11. The disposable cartridge of claim 1, wherein the cap flat surface comprises a gasket.

12. The disposable cartridge of claim 1, wherein the cap rotates about the hinge in a plane perpendicular to a plane defined by the upper surface.

13. The disposable cartridge of claim 1, wherein the cap rotates about the hinge in a plane parallel to a plane defined by the upper surface.

14. The disposable cartridge of claim 13, wherein the cap comprises a sweeping edge for skimming off any excess of the sample from the sample inlet portion when the cartridge is adjusted from the unsealed configuration to the sealed configuration.

15. The disposable cartridge according to claim 14, further comprising a groove disposed at the underside of the cap in front of the sweeping edge of the cap, for holding excess sample.

16. The disposable cartridge according to claim 13, wherein the sample inlet portion further comprises a sample overflow well for receiving excess sample.

17. The disposable cartridge according to claim 1, further comprising means for securing the cap when the cartridge is in the sealed configuration.

18. The disposable cartridge according to claim 8, wherein the at least one reagent is selected from dry thromboplastin, celite, and kaolin.

19. A method for measuring one or more properties of a blood sample in a disposable cartridge, comprising:
i) providing the disposable cartridge of claim 1 in an unsealed configuration, and depositing the blood sample into the sample storage well;
ii) adjusting the cartridge from the unsealed configuration to the sealed configuration;
iii) providing an analyzer comprising:
a receptor for receiving the cartridge;
one or more than one processor for controlling the analyzer;
means for squeezing the air bladder;
a source of electromagnetic radiation for interrogating the blood in the optical chamber; and
one or more detectors for receiving the signals generated from the blood in the optical chamber;
iv) inserting the disposable cartridge in the sealed configuration; into the receptor of the analyzer;
v) squeezing the air bladder to provide pressurized air to the closed air passage, for urging blood out of the sample storage well and stopping a leading edge of the blood at a position between the optical chamber exit and the vent; and
vi) sending the signals generated from the blood in the optical chamber to the one or more than one processor for transforming the signals into the one or more properties of the blood sample.

20. A method for measuring a plurality of properties of a blood sample in a disposable cartridge comprising:
i) providing the disposable cartridge of claim 1 in an unsealed configuration, and depositing the blood sample into the sample storage well, the disposable cartridge further comprising a biosensor chamber for generating signals from the blood sample, the biosensor chamber disposed between an optical chamber exit and the vent, a biosensor chamber exit, operatively connected to the biosensor chamber;

ii) adjusting the cartridge from the unsealed configuration to the sealed configuration;

iii) providing an analyzer comprising:
- a receptor for receiving the cartridge;
- one or more than one processor for controlling the analyzer;
- means for squeezing the air bladder;
- a source of electromagnetic radiation for interrogating the blood in the optical chamber; and
- a plurality of detectors for receiving the signals generated from the blood in the biosensor chamber;

iv) inserting the disposable cartridge in the sealed configuration, into the receptor of the analyzer; and if biosensor calibration is required,
- v-1a) squeezing the air bladder to provide pressurized air to the closed air passage, for urging the blood out of the sample storage well into an optical chamber, and stopping a leading edge of the blood at a position between an optical chamber exit and the biosensor chamber entrance, and
- v-1b) calibrating the one or more biosensors prior to urging the blood into the biosensor chamber, and
- v-1c) stopping the leading edge of the blood at a position between the biosensor chamber exit and the cartridge vent;

or if biosensor calibration is not required,
- v-2) urging the blood into the optical chamber and the biosensor chamber and stopping a leading edge of the blood at a position between the biosensor chamber exit and the cartridge vent;

vi) sending the signals generated from the blood in the optical chamber and the blood in the biosensor chamber to the one or more than one processor for transforming the signals into the plurality of properties of the blood sample.

* * * * *